United States Patent [19]
Lansbury, Jr. et al.

[11] Patent Number: 6,054,114
[45] Date of Patent: Apr. 25, 2000

[54] ORGANOMETALLIC LIGANDS FOR THE LOCALIZATION AND QUANTIFICATION OF AMYLOID IN VIVO AND IN VITRO

[75] Inventors: Peter T. Lansbury, Jr., Brookline, Mass.; Hogyu Han; Cheon-Gyu Cho, both of Seoul, Rep. of Korea; Weiguo Zhen, Waltham, Mass.; James D. Harper, Cambridge, Mass.; Alan Davison, West Roxbury, Mass.

[73] Assignee: Massachusetts Institute of Technology, Cambridge, Mass.

[21] Appl. No.: 08/852,825

[22] Filed: May 7, 1997

Related U.S. Application Data

[60] Provisional application No. 06/016,599, May 8, 1996, and provisional application No. 60/038,999, Feb. 25, 1997.

[51] Int. Cl.[7] .......................... A61K 51/00; A61K 49/00; C07F 13/00
[52] U.S. Cl. ........................ 424/1.11; 424/9.1; 534/10; 534/12; 534/14; 534/883; 556/45
[58] Field of Search ................................ 534/10, 12, 14, 534/670, 671, 883; 424/1.11, 1.37, 9.1; 556/45

[56] References Cited

U.S. PATENT DOCUMENTS

| | | | |
|---|---|---|---|
| 4,933,156 | 6/1990 | Quay et al. | 424/1.1 |
| 5,268,164 | 12/1993 | Kozarich et al. | 424/9 |

FOREIGN PATENT DOCUMENTS

| | | |
|---|---|---|
| WO91/16355 | 10/1991 | WIPO . |
| WO93/04194 | 3/1993 | WIPO . |
| WO95/20979 | 8/1995 | WIPO . |
| WO96/34853 | 11/1996 | WIPO . |

OTHER PUBLICATIONS

Saito et al., Vector–mediated delivery of [125]I–labeled β–amyloid peptide Aβ$^{1-40}$ through blood–brain barrier and binding to Alzheimer disease amyloid of the Aβ$^{1-40}$/vector complex, PNAS USA 92: 10227–10231 (1995).

Pollack et al., Sulfonated dyes attenuate the toxic effects of β–amyloid in a structure–specific fashion, Neuroscience Letters 197:211–214 (1995).

Klunk et al., Chrysamine–G binding to Alzheimer and control brain: Autopsy study of a new amyloid probe, Neurobiology of Aging 16(4):541–548 (1995).

Park, L.Y. Ph.D. Thesis, Massachusetts Institute of Technology, Cambridge, MA, pp. 94–98, 170–173, (1992).

Caughey and Raymond, Sulfated Polyanion Inhibition of Scrapie–Associated PrP Accumulation in Cultured Cells. J. of Virology, 67(2):643–650 (1993).

Lorenzo and Yankner, β–amyloid neurotoxicity requires fibril formation and is inhibited by Congo red, Proc. Natl. Acad. Sci. USA 91:12243–12247 (1994).

Award and Aly, Synthesis and Antimicrobial Activity of Some New 3–Azo(p–substituted benzene–sulphonamido–)–bipyridyls and their Chelates, Synth. React. Inorg. Met.–Org. Chem. 21(3):375–383 (1991).

Calogero et al., An Approach to the Design of Non–Mutagenic Azo Dyes:2. Potential Replacements for the Benzidine Moiety of Some Mutagenic Azo Dyestuffs, Dyes Pigm. 8:431–447 (1987).

Han et al., Technetium Complexes for the Quantitation of Brain Amyloid, J. Am. Chem. Soc. 118: 4506–4507 (1996).

Madras et al., Technepine: A High–Affinity $^{99m}$Technetium Probe to Label the Dopamine Transporter in Brain by SPECT Imaging, Synapse 22:239–246 (1996).

Klunk et al., Development of Small Molecule Probes for the Beta–Amyloid Protein of Alzheimer's Disease, Neurobiology of Aging 15(6):691–698 (1994).

Maggio et al., Reversible in vitro growth of Alzheimer disease β–amyloid plaques by deposition of labeled amyloid peptide, Proc. Natl. Acad. Sci. USA 89:5462–5466 (1992).

Ashburn et al., Amyloid Probes Based on Congo Red Distinguish Between Fibrils Comprising Different Peptides, Chem. and Biol. 3(5):351–358 (1996).

Straub et al., Chemical Pathways of Degradation of the Bradykinin Analog, RMP–7, Pharmaceutical Research 12(2), 305–308 (1995).

Walker et al., Labeling of β–Amyloid in Vivo, Abstract #98, Third International Conference on Alzheimer's Disease, pp. S23–S24 (1992).

Abrams et al., Synthesis and Characterization of Hexakis (alkyl isocyanide) and Hexakis (aryl isocyanide) Complexes of Technetium (I), Inorg. Chem. 22:2798–2800 (1983).

Juhasz and Biemann, Mass spectrometric molecular–weight determination of highly acidic compounds of biological significance via their complexes with basic polypeptides, PNAS USA 91:4333–4337 (1994).

Klunk et al., Quantitative Evaluation of Congo Red Binding to Amyloid–like Proteins with a Beta–pleated Sheet Conformation, J. Histochem. Cytochem. 37:1273–1281 (1989).

Knorpp et al., Radiosulfur ($S^{35}$) Labeled Congo Red Dye, J. Nucl. Med. 1:23–20 (1960).

Neuwelt, Implications of the Blood–Brain Barrier and Its Manipulation, vol. I, Plenum Press, NY (1989), pp. 332–338 and 358–364.

(List continued on next page.)

*Primary Examiner*—Keith D. MacMillan
*Assistant Examiner*—P. Ponnaluri
*Attorney, Agent, or Firm*—Ernest V. Linek; Banner & Witcoff

[57] ABSTRACT

Novel organometallic compounds for binding amyloid are described. Methods using such compounds for determining by imaging the localization or quantification of amyloid fibrils in a mammal, for diagnosing the degree of progression of Alzheimer's disease in a mammal, for monitoring the response to a therapy in a mammal having Alzheimer's disease, for identifying an agent useful for treating Alzheimer's disease, for treating Alzheimer's disease, and for detecting the presence of the infectious form of the prion protein, are also described.

2 Claims, No Drawings

OTHER PUBLICATIONS

Neuwelt, Implications of the Blood–Brain Barrier and Its Manipulation, vol. II, Plenum Press, NY (1989). pp. 29–33, 41–51, 207–213 and 257–258.

O'Connell et al., Technetium (I) Isocyanide Complexes with Bidentate Aromatic Amine Ligands: Structural Characterization of $[Tc(CNtBu)_4(bpy)]PT_6$, Complex with "Tc(III) Character", Inorg. Chem 29:3539–47 (1990).

Photaki et al., On Cysteine and Cystine Peptides, Part V. S–Trityl– and S–Diphenyl–methyl–cysteine and –cysteine Peptides, J. Chem. Soc. (c) 2683–2687 (1970).

Tubis et al., The Preparation and Use of Radioiodinated Congo Red in Detecting Amyloidosis, J. Am. Pharmaceutical Assn 49:422–425 (1960).

ORGANOMETALLIC LIGANDS FOR THE LOCALIZATION AND QUANTIFICATION OF AMYLOID IN VIVO AND IN VITRO

This application claims the benefit of U.S. Provisional Application No. 60/016,599 filed May 8, 1996, and U.S. Provisional Application No. 60/038,999 filed Feb. 25, 1997.

The U.S. Government has a paid-up license in this invention and the right in limited circumstances to require the patent owner to license others on reasonable terms as provided for by the terms of Grant No. AG08470 awarded by the National Institutes of Health, National Institute on Aging.

FIELD OF THE INVENTION

The present invention relates to novel organometallic ligands which interact with amyloid fibrils, anti methods for using such ligands for diagnosing, treating and monitoring therapies for Alzheimer's and other diseases.

BACKGROUND OF THE INVENTION

Alzheimer's disease is the most prevalent form of senile dementia. Epidemiological studies suggest that 25–50% of all people in their 80's have Alzheimer's disease. Generally, the first symptom of Alzheimer's disease is memory loss, followed by a decline in reasoning ability and reduced use of speech. Behavioral disorders are also often present. The deterioration appears to be irreversible, and eventually leads to death. There is no effective treatment currently available.

Alzheimer's disease was originally described, and is still diagnosed, based on the presence in the postmortem brain of pertinacious deposits, known as amyloid plaques, which stain with the dye Congo Red. Amyloid plaques contain a core comprising ordered fibrillar protein aggregates. In Alzheimer's disease, the predominant brain amyloid proteins are β1-42 and its C-terminally truncated relative β1-40.

Determination of amyloid load is typically accomplished by counting Congo Red stained amyloid plaques per microscopic field in brain tissue sections of subjects during autopsies. There is a need for probes which allow localization and quantification of amyloid deposits and which can be used in live persons so as to non-invasively diagnose the presence of Alzheimer's disease and/or monitor the efficacy of different treatments for Alzheimer's disease.

There is also a need for such probes for certain other neurodegenerative diseases which affect various mammals, e.g., the prion diseases, e.g., scrapie, bovine spongiform encephalopathy ("mad cow disease"), and Creutzfeldt-Jacob disease.

SUMMARY OF THE INVENTION

It is an object of the invention to provide compounds which can be used in vivo for detecting amyloid.

It is yet another object of the invention to provide a safe, effective and easy method for detecting the localization and/or quantification of amyloid fibrils in the body.

It is yet another object of the invention to non-invasively measure amyloid deposits in the body by imaging techniques.

It is yet another object of the invention to use Congo Red or Chrysamine G analogs to carry metals to in vivo amyloid plaque for the purpose of imaging.

It is yet another object of the invention to use organometallic compounds which can cross the blood brain barrier to localize and/or quantify amyloid fibrils in the brain.

It is yet another object of the invention to establish the time course of amyloid deposition in the brain of a patient and compare it to the appearance of Alzheimer's disease symptoms in the patient.

It is yet another object of the invention to non-invasively diagnose the presence and/or degree of progression of Alzheimer's disease in a patient.

It is yet another object of the invention to non-invasively monitor treatments for Alzheimer's disease in a patient.

It is yet another object of the invention to treat Alzheimer's disease in a patient with compounds which bind to amyloid fibrils and thereby inhibit their aggregation into amyloid plaques.

It is yet another object of the invention to localize and/or quantify amyloid deposits in the body during autopsies.

It is yet another object of the invention to identify compounds which are useful for treating a disease associated with accumulation of aggregated amyloid.

Still another object of the invention is to provide compounds which can be used for detecting prion protein.

According to the invention amyloid binding compounds are provided. The compounds are of the formula:

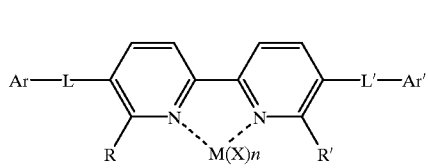

(I)

and pharmaceutically acceptable salts thereof, wherein

R and $R^1$ are H, $N_2H_x$ (x is 0, 1, 2, 3 or 4), $CH_2OH$, $CH_2NH_2$, $CH_2SH$, $o\text{-}C_6H_4CH_2COOH$, $CH_2NHCH_2CH_2SH$, $CH_2P(CH_3)_2$, or $CH_2PCH_2P(CH_3)_2$, and can be the same or different from each other, and if R or $R^1$ is not H it can additionally bind or not bind to M, and if R or $R^1$ is H it cannot bind to M;

M is $^{99m}Tc$, $^{111}In$, $^{90}Y$, $^{99}Tc$, $^{186}Re$, Cd, Zn, Co, Cu, Fe, Ni, or oxo forms of these metals;

X is Cl, I, Br, F, $P(R^2)_3$ ($R^2$ is $C_{1-6}$ hydrocarbon), $P(Ar^2)_3$ ($Ar^2$ is aryl or substituted aryl), $R^3NC$ ($R^3$ is $C_{1-6}$ hydrocarbon), $Ar^3NC$ ($Ar^3$ is aryl or substituted aryl), $SR^4$ ($R^4$ is $CH_2CH_2SH$ or $C_{1-6}$ hydrocarbon), or $P(R^5)_2$ $R^6$ ($R^5$ is $C_{1-6}$ hydrocarbon; $R^6$ is $C_{1-6}$ hydrocarbon or $CH_2CH_2P(CH_3)_2$, and each X can be the same or different from each other;

n is the number 1, 2, 3 or 4;

L and L' are —N=N—, —CONH—, —NHCO—, —HN—NH—, or —C=C—, and can be the same or different from each other; and Ar and Ar' are

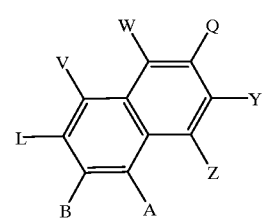

-continued

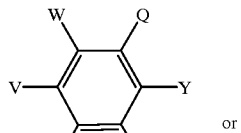

or

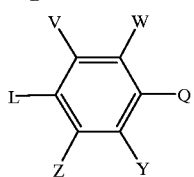

and can be the same or different from each other, where each of V, W, Q, Y, Z, A and B is OH, COOH, H, $R^5$ ($R^5$ is $C_{1-6}$ hydrocarbon), $CO_2R^6$ ($R^6$ is $C_{1-6}$ hydrocarbon), $CONH_2$, CN, $NH_2$, $CH_2NH_2$ or $SO_3$ and can be the same or different from each other.

Another aspect of the invention is an amyloid binding compound of the formula:

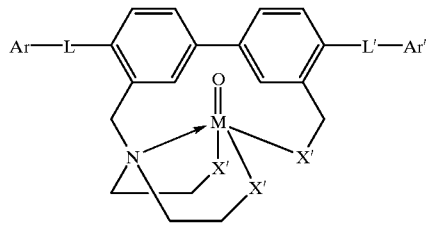

(II)

and pharmaceutically acceptable salts thereof, wherein

M is $^{99m}Tc$, $^{111}In$, $^{90}Y$, $^{99}Tc$ or $^{186}Re$;

X' is S, NH or O;

L and L' are —N=N—, —CONH—, —NHCO—, —HN—NH—, or —C=C—, and can be the same or different from each other; and Ar and Ar' are

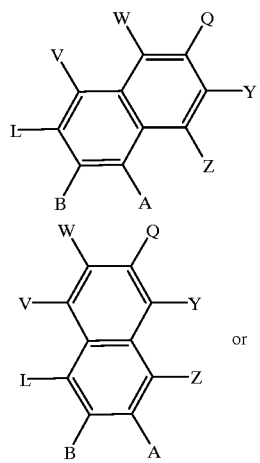

or

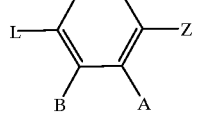

-continued

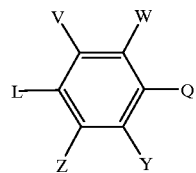

and can be the same or different from each other, where each of V, W, Q, Y, Z, A and B is OH, COOH, H, $R^5$ ($R^5$ is $C_{1-6}$ hydrocarbon), $CO_2R^6$ ($R^6$ is $C_{1-6}$ hydrocarbon), $CONH_2$, CN, $NH_2$, $CH_2NH_2$ or $SO_3$ and can be the same or different from each other.

Another aspect of the invention is an amyloid binding compound of the formula:

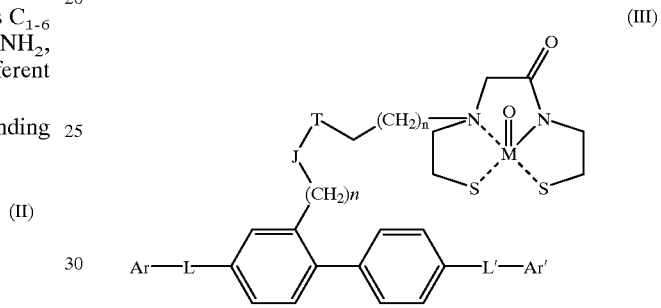

(III)

and pharmaceutically acceptable salts thereof, wherein

J is NH, O or S;

T is CO or $CH_2$;

n is the number 1, 2, 3, 4, 5 or 6;

M is $^{99m}TC$, $^{111}In$, $^{90}Y$, $^{99}Tc$ or $^{186}Re$;

L and L' are —N=N—, —CONH—, —NHCO—, —HN—NH—, or —C=C—, and can be the same or different from each other; and Ar and Ar' are

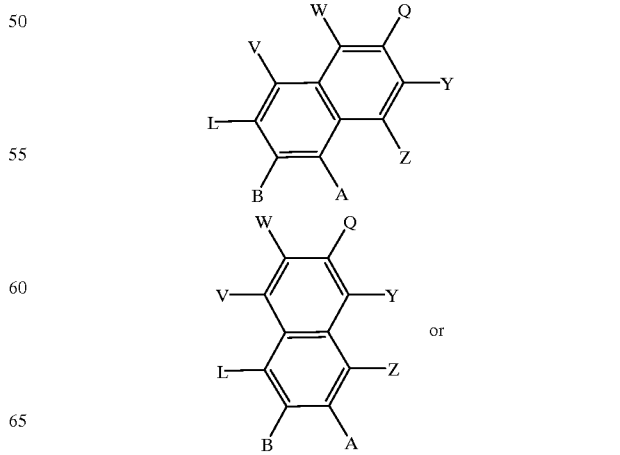

or

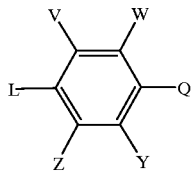

and can be the same or different from each other, where each of V, W, Q, Y, Z, A and B is OH, COOH, H, $R^5$ ($R^5$ is $C_{1-6}$ hydrocarbon), $CO_2R^6$ ($R^6$ is $C_{1-6}$ hydrocarbon), $CONH_2$, CN, $NH_2$, $CH_2NH_2$ or $SO_3$ and can be the same or different from each other.

Another aspect of the invention is an amyloed binding compound of the formula:

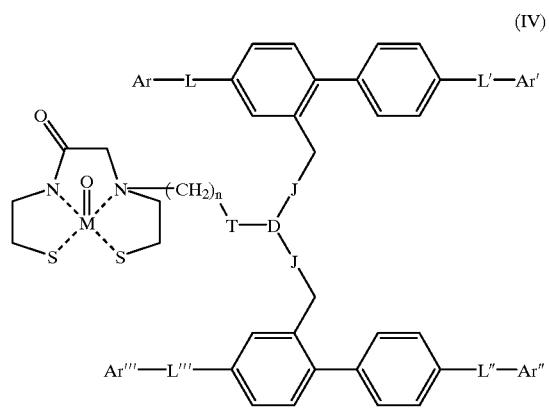

(IV)

and pharmaceutically acceptable salts thereof,
wherein
J is NH or S;
T is CO or $CH_2$;
n is the number 1, 2, 3, 4, 5 or 6;
M is $^{99m}Tc$, $^{111}In$, $^{90}Y$, $^{99}Tc$ or $^{186}Re$;
L, L', L" and L'" are —N=N—, —CONH—, —NHCO—, —HN—NH—, or —C≡C—, and can be the same or different from each other;
Ar, Ar', Ar" and Ar'" are

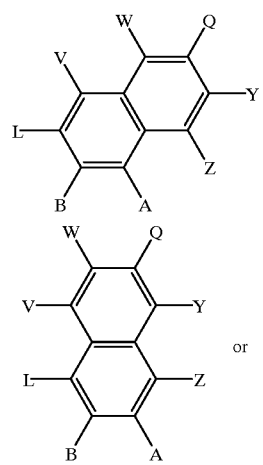

or

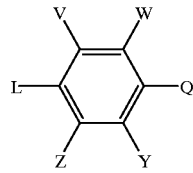

and can be the same or different from each other, where each of V, W, Q, Y, Z, A and B is OH, COOH, H, $R^5$ ($R^5$ is $C_{1-6}$ hydrocarbon), $CO_2R^6$ ($R^6$ is $C_{1-6}$ hydrocarbon), $CONH_2$, CN, $NH_2$, $CH_2NH_2$ or $SO_3$ and can be the same or different from each other; and when J is NH and T is CO, then D is a trifunctional linker with two carboxyl groups and one amine group,
when J is NH and T is $CH_2$, then D is $COCH_2(CH_2S)CH_2CO$,
when J is S and T is CO, then D is $CH_2CH(CH_2NH)CH_2$, and
when J is S and T is $CH_2$, then D is $CH_2CH(CH_2S)CH_2$.

Another aspect of the invention is an amyloid binding compound of the formula:

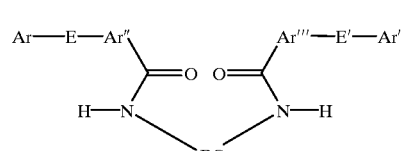

(V)

and pharmaceutically acceptable salts thereof,
wherein
BG is any dicarbonyl or dithiocarbonyl moiety;
E and E' are

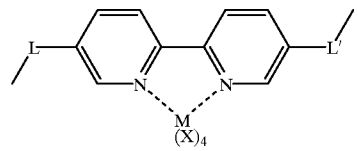

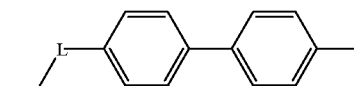

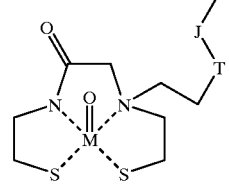

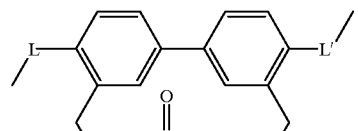

or

-continued

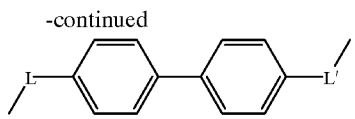

and can be the same or different from each other,
wherein

M is $^{99m}Tc$, $^{111}In$, $^{90}Y$, $^{99}Tc$ or $^{186}Re$;

L and L' are —N=N—, —CONH—, —NHCO—, —HN—NH—, or —C=C—, and can be the same or different from each other;

J is NH or S;

T is CO or $CH_2$;

X is Cl, I, Br, F, $P(R^2)_3$ ($R^2$ is $C_{1-6}$ hydrocarbon), $P(Ar^2)_3$ ($Ar^2$ is aryl or substituted aryl), $R^3NC$ ($R^3$ is $C_{1-6}$ hydrocarbon), $Ar^3NC$ ($Ar^3$ is aryl or substituted aryl), $SR^4$ ($R^4$ is $CH_2CH_2SH$ or $C_{1-6}$ hydrocarbon), or $P(R^5)_2R^6$ ($R^5$ is $C_{1-6}$ hydrocarbon; $t^6$ is $C_{1-6}$ hydrocarbon or $CH_2CH_2P(CH_3)_2$, and each X can be the same or different from each other;

Ar and Ar' are

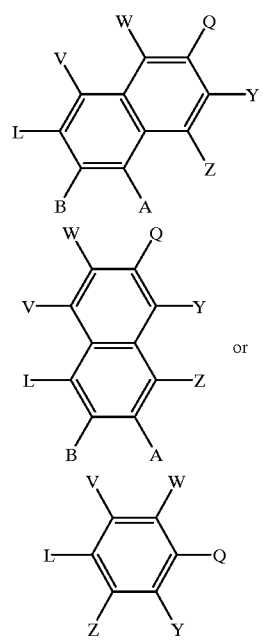

and can be the same or different from each other, where each of V, W, Q, Y, Z, A and B is OH, COOH, H, $R^5$ ($R^5$ is $C_{1-6}$ hydrocarbon), $CO_2R^6$ ($R^6$ is $C_{1-6}$ hydrocarbon), $CONH_2$, CN, $NH_2$, $CH_2NH_2$ or $SO_3$ and can be the same or different from each other, and Ar'' and Ar''' are

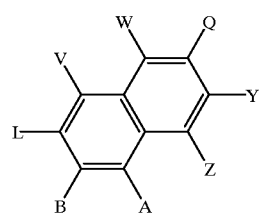

-continued

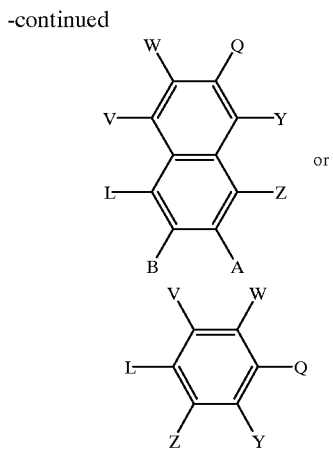

and can be the same or different from each other, where one of V, W, Q, Y, Z, A and B is COOH and each of the others is OH, COOH, H, $R^5$ ($R^5$ is $C_{1-6}$ hydrocarbon), $CO_2R^6$ ($R^6$ is $C_{1-6}$ hydrocarbon), $CONH_2$, CN, $NH_2$, $CH_2NH_2$ or $SO_3$ and can be the same or different from each other.

Another aspect of the invention is an amyloid binding compound of the formula:

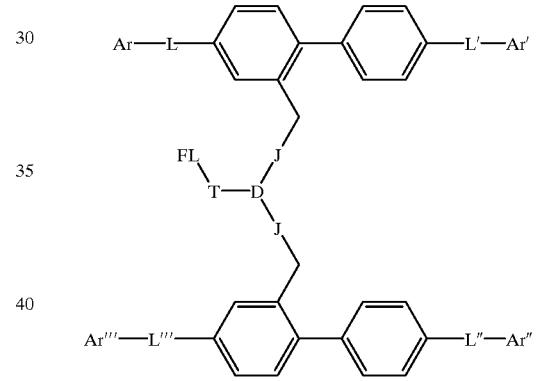

(IX)

and pharmaceutically acceptable salts thereof,
wherein

J is NH or S;

T is CO or $CO_2$;

FL is fluorescein, rhodamine, coumarin or any other fluorescent moiety;

L and L' are —N=N—, —CONH—, —NHCO—, —HN—NH—, or —C=C—, and can be the same or different from each other; and Ar and Ar' are

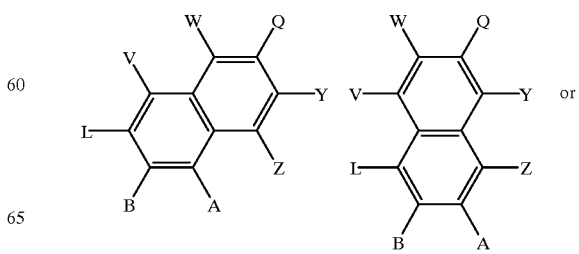

-continued

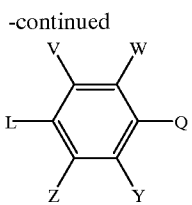

and can be the same or different from each other, where each of V, W, Q, Y, Z, A and B is OH, COOH, H, $R^5$ ($R^5$ is $C_{1-6}$ hydrocarbon), $CO_2R^6$ ($R^6$ is $C_{1-6}$ hydrocarbon), $CONH_2$, CN, $NH_2$, $CH_2NH_2$ or $SO_3$ and can be the same or different from each other.

Another aspect of the invention is an amyloid binding compound of the formula:

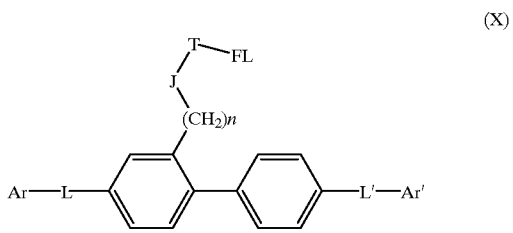

(X)

and pharmaceutically acceptable salts thereof,
wherein
J is NH or S;
T is CO or $CO_2$;
FL is fluorescein, rhodamine, coumarin or any other fluorescent moiety;
L and L' are —N=N—, —CONH—, —NHCO—, —HN—NH—, or —C=C—, and can be the same or different from each other; and
Ar and Ar' are

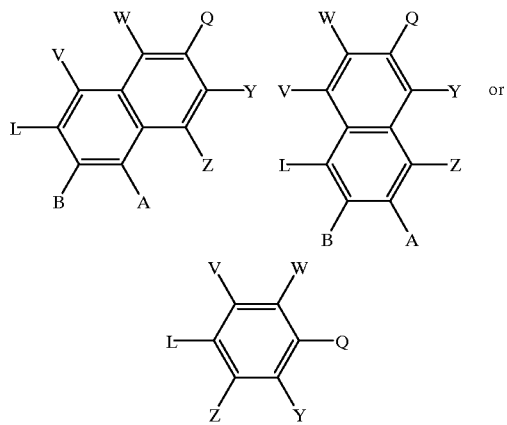

and can be the same or different from each other, where each of V, W, Q, Y, Z, A and B is OH, COOH, H, $R^5$ ($R^5$ is $C_{1-6}$ hydrocarbon), $CO_2R^6$ ($R^6$ is $C_{1-6}$ hydrocarbon), $CONH_2$, CN, $NH_2$, $CH_2NH_2$ or $SO_3$ and can be the same or different from each other.

Another aspect of the invention is a method for diagnosing the degree of progression of Alzheimer's disease in a mammal. A first mammal having Alzheimer's disease and having brain amyloid fibrils, e.g., protofibrils, type-1 fibrils, type-2 fibrils, neuritic plaque, diffuse amyloid or combinations thereof, is provided. A labeled ligand, e.g., an organometallic ligand, where the label is, e.g., technetium-99m, indium-111, yttrium-90, rhenium-186 or technetium-99, capable of interacting with the amyloid fibrils is also provided. Preferred labeled ligands are compounds of formula I, II, III, IV, V, or pharmaceutically acceptable salts thereof. The labeled ligand is administered to the mammal under conditions which allow the labeled ligand to interact with the amyloid fibrils in the brain so as to result in labeled amyloid fibrils. The localization or quantification of the labeled amyloid fibrils in the mammal is determined by imaging, e.g., radioimaging, magnetic resonance imaging or single photon emission computed tomographic imaging, so as to diagnose the degree of progression of the Alzheimer's disease. In certain embodiments, the localization or quantification of the labeled amyloid fibrils is compared to a standard.

Another aspect of the invention is a method for monitoring the response to a therapy in a mammal having Alzheimer's disease. A mammal having Alzheimer's disease and having brain amyloid fibrils is provided. The mammal is treated with a therapy for Alzheimer's disease. The response of the mammal to the treating step is monitored by determining whether the therapy alters the localization or quantification of the amyloid fibrils in the mammals. In certain embodiments, the determining step comprises providing a labeled ligand, e.g., a compound of formula I, II, III, IV, V, or pharmaceutically acceptable salts thereof, capable of interacting with the amyloid fibrils. The labeled ligand is administered to the mammal under conditions which allow the labeled ligand to interact with the amyloid fibrils in the brain so as to result in labeled amyloid fibrils. The localization or quantification of the labeled amyloid fibrils in the mammal is determined by imaging.

Another aspect of the invention is a method for evaluating the ability of an agent to alter the localization or quantification of brain amyloid fibrils in a mammal. A mammal having brain amyloid fibrils is provided. An agent is provided. The agent is administered to the mammal and it is determined whether the agent alters the localization or quantification of the brain amyloid fibrils in the mammal.

Another aspect of the invention is a method for identifying an agent useful for treating a mammal having a disease associated with aggregated amyloid. A mammal having such a disease and having amyloid fibrils is provided. An agent is provided and administered to the mammal. It is determined if the agent alters the localization or quantification of the amyloid fibrils in the mammal. An alteration in the localization or quantification which results in a localization or quantification more similar to that of a mammal which does not have the disease is correlated with the agent being useful for treating the mammal having the disease. The invention also includes the agent obtainable by this method.

Another aspect of the invention is a method for determining the localization or quantification of amyloid fibrils in a mammal. A mammal having amyloid fibrils, e.g, in the brain, pancreas, vasculature, spleen, liver, kidneys, adrenals, lymph nodes, muscle, cardiovascular system, skin, or any combination thereof, is provided. An organometallic ligand capable of interacting with the amyloid fibrils is provided, e.g., a compound of formula I, II, III, IV, V, or pharmaceutically acceptable salts thereof. The organometallic ligand is administered to the mammal under conditions which allow the organometallic ligand to interact with the amyloid fibrils so as to result in organometallic ligand-amyloid fibril complexes. The localization or quantification of the complexes is determined in the mammal, e.g., by imaging. In certain embodiments, the administering and determining steps are repeated after a time interval so as to establish a time course for the localization or quantification of the complexes in the mammal. In other embodiments, the mammal is deceased, and the administering step is, e.g., to the postmortem brain or a portion thereof.

Another aspect of the invention is a method for treating Alzheimer's disease in a mammal. A mammal having Alzheimer's disease is provided. The mammal has non-aggregated amyloid proteins or aggregated amyloid proteins, or combinations thereof. An organometallic ligand capable of interacting with the non-aggregated amyloid proteins, or with the aggregated amyloid proteins, or with both of the amyloid proteins, is provided, e.g., a compound of formula I, II, III., IV, V, or pharmaceutically acceptable salts thereof. A therapeutically effective amount of the organometallic ligand is administered to the mammal under conditions which allow the organometallic ligand to interact with the non-aggregated amyloid proteins so as to inhibit aggregation of the amyloid proteins, or with the aggregated amyloid proteins, or with both of the amyloid proteins, such that treatment of the Alzheimer's disease occurs.

Another aspect of the invention is a pharmaceutical composition for treating Alzheimer's disease in a mammal comprising a therapeutically effective amount of an organometallic ligand, e.g., a compound of formula I, II, III, IV, V, or pharmaceutically acceptable salts thereof, the ligand being able to interact with amyloid proteins in a mammal in need of treatment for Alzheimer's disease, and a pharmaceutically acceptable carrier.

Another aspect of the invention is a method for determining the localization or quantification of amyloid fibrils in a deceased mammal. A deceased mammal or a portion thereof having amyloid fibrils is provided. An organometallic ligand, e.g., a compound of formula I, II, III, IV, V, or pharmaceutically acceptable salts thereof, capable of interacting with the amyloid fibrils is provided. The organometallic ligand is administered to the mammal or portion thereof under conditions which allow the organometallic ligand to interact with the amyloid fibrils so as to result in organometallic ligand-amyloid fibril complexes. The localization or quantification of the complexes in the mammal or portion thereof is determined, e.g., by autoradiography, SPECT or PET imaging.

Another aspect of the invention is a method for detecting the presence of aggregated prion protein in a mammal. A mammal is provided. Bodily fluid or tissue, e.g., lymph, blood or urine, obtained from the mammal is provided. A labeled ligand capable of interacting with aggregated prion protein is provided, e.g., a compound of formula I, II I III, IV, V, or pharmaceutically acceptable salts thereof. The bodily fluid or tissue is contacted in vitro with the labeled ligand under conditions which allow the labeled ligand to interact with the aggregated prion protein if the aggregated prion protein is present in the bodily fluid or tissue, so as to result in labeled aggregated prion protein. The presence or absence of the labeled aggregated prion protein in the bodily fluid or tissue is determined. In certain embodiments, the mammal has a prion disease, e.g., scrapie, bovine spongiform encephalopathy or Creutzfeldt-Jacob disease.

Another aspect of the invention is a method for detecting the presence of aggregated prion protein in a mammal. A mammal is provided. A labeled ligand capable of interacting with aggregated prion protein is provided, e.g., a compound of formula I, II, III, IV, V, or pharmaceutically acceptabLe salts thereof. The labeled ligand is administered to the mammal under conditions which allow the labeled ligand to interact with the aggregated prion protein if the aggregated prion protein is present in the mammal, so as to result in labeled aggregated prion protein. The presence or absence of the labeled aggregated prion protein is determined in the mammal by imaging.

Another aspect of the invention is a method for determining the presence of aggregated intracellular $\beta$-amyloid. Cells having $\beta$-amyloid are provided. A fluorescent ligand capable of interacting with aggregated $\beta$-amyloid, e.g., a compound of formula IX or X, is provided. The cells are contacted with the fluorescent ligand under conditions which allow the fluorescent ligand to interact with aggregated $\beta$-amyloid if it is present so as to result in fluorescent-labeled aggregated $\beta$-amyloid. The presence or absence of a fluorescent signal is determined. The presence of a fluorescent signal indicates the presence of aggregated intracellular $\beta$-amyloid.

Another aspect of the invention is a method for identifying an agent useful for treating a mammal for a disease characterized by aggregated intracellular $\beta$-amyloid. Cells having $\beta$-amyloid are provided. An agent is provided. A fluorescent ligand capable of interacting with $\beta$-amyloid fibrils, e.g., a compound of formula IX or X, is provided. The cells are contacted with the agent to form a mixture under conditions which allow aggregation of the $\beta$-amyloid if the agent was not present. The mixture is contacted with the fluorescent ligand under conditions which allow the fluorescent ligand to interact with $\beta$-amyloid fibrils if they are present so as to result in fluorescent-labeled $\beta$-amyloid fibrils. It is determined if the agent inhibits aggregation of the $\beta$-amyloid. The presence of a fluorescent signal indicates the presence of $\beta$-amyloid fibrils and therefore minimal or no inhibition by the agent. The absence of a fluorescent signal indicates the absence of $\beta$-amyloid fibrils and therefore inhibition by the agent. This inhibition is correlated with the agent being useful for treating a mammal for a disease characterized by aggregated intracellular $\beta$-amyloid.

Another aspect of the invention is a method for identifying a labeled ligand which selectively binds to one type of $\beta$-amyloid fibril. A labeled compound is provided, e.g., a compound of formula I, II, III, IV, V, or pharmaceutically acceptable salts thereof. First $\beta$amyloid fibrils are provided, and second $\beta$-amyloid are provided. The labeled compound is contaced with the first $\beta$-amyloid fibrils under conditions which allow the labeled ligand to interact with the first $\beta$-amyloid fibrils. It is determined if the labeled compound binds to the first $\beta$-amyloid fibrils. If the labeled compound does not bind to the first $\beta$-amyloid fibrils, then the labeled compound is contacted with the second $\beta$-amyloid fibrils under conditions which allow the labeled compound to interact with the second $\beta$-amyloid fibrils. It is determined if the labeled compound binds to the second $\beta$-amyloid fibrils, binding being correlated with a labeled ligand which selectively binds to the second $\beta$-amyloid fibrils as compared to the first $\beta$-amyloid fibrils. The invention also includes the labeled ligand obtainable from this method.

Another aspect of the invention is a method for identifying a labeled ligand which binds to one or more amyloid proteins, e.g., $\beta$-amyloid, Islet amyloid polypeptide, Ig light chain, transthyretin, lysosome, or $\beta$-$_2$-microglobulin, using, e.g., a labeled compound of formula I, II, III, IV, V, or pharmaceutically acceptable salts thereof. The invention also includes the labeled ligand obtainable from this method.

The above and other objects, features and advantages of the present invention will be better understood from the following specification.

DETAILED DESCRIPTION

This invention provides an amyloid binding compound of the formula:

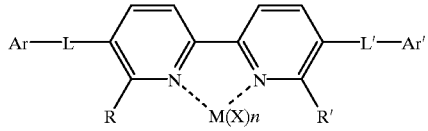

(I)

and pharmaceutically acceptable salts thereof, wherein

R and $R^1$ are H, $N_2H_x$ (x is 0, 1, 2, 3 or 4), $CH_2OH$, $CH_2NH_2$, $CH_2SH$, $o\text{-}C_6H_4CH_2COOH$, $CH_2NHCH_2CH_2SH$, $CH_2P(CH_3)_2$, or $CH_2PCH_2CH_2P(CH_3)_2$, and can be the same or different from each other, and if R or $R^1$ is not H it can additionally bind or not bind to M, and if R or $R^1$ is H it cannot bind to M;

M is $^{99m}Tc$, $^{111}In$, $^{90}Y$, $^{99}Tc$, $^{186}Re$, Cd, Zn, Co, Cu, Fe, Ni, or oxo forms of these metals;

X is Cl, I, Br, F, $P(R^2)_3$ ($R^2$ is $C_{1-6}$ hydrocarbon), $P(Ar^2)_3$ ($Ar^2$ is aryl or substituted aryl), $R^3NC$ ($R^3$ is $C_{1-6}$ hydrocarbon), $Ar^3NC$ ($Ar^3$ is aryl or substituted aryl), $SR^4$ ($R^4$ is $CH_2CH_2SH$ or $C_{1-6}$ hydrocarbon), or $P(R^5)_2R^6$ ($R^5$ is $C_{1-6}$ hydrocarbon; $R^6$ is $C_{1-6}$ hydrocarbon or $CH_2CH_2P(CH_3)_2$, and each X can be the same or different from each other;

n is the number 1, 2, 3 or 4;

L and L' are —N=N—, —CONH—, —NHCO—, —HN—NH—, or —C=C—, and can be the same or different from each other; and Ar and Ar' are

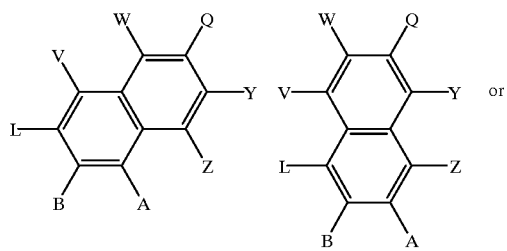

or

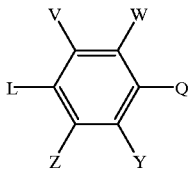

and can be the same or different from each other, where each of V, W, Q, Y, Z, A and B is OH, COOH, H, $R^5$ ($R^5$ is $C_{1-6}$ hydrocarbon), $CO_2R^6$ ($R^6$ is $C_{1-6}$ hydrocarbon), $CONH_2$, CN, $NH_2$, $CH_2NH_2$ or $SO_3$ and can be the same or different from each other.

These compounds are referred to herein as BIPY compounds. The metals, M, can be radioactive, e.g., $^{99m}Tc$, $^{111}In$, $^{90}Y$, $^{99}Tc$ or $^{186}Re$, or non-radioactive, e.g., Cd, Zn, Co, Cu, Fe or Ni. Preferably, the radioactive metal is $^{99m}Tc$. The oxo forms of the metals, e.g., Re=O or Tc=O, are preferred. The oxo forms are generally more stable and are charge neutral.

In certain embodiments, if the R or $R^1$ groups are any group except H, each or both can, but do not have to, additionally bind to M. See, e.g., compounds 15, 28, 35, 45, 54 and 66.

When the X moiety is $P(R^2)_3$, the $R^2$ can be any $C_{1-6}$ hydrocarbon, e.g., alkyl or substituted alkyl group, e.g., methyl or ethyl or t-butyl or, e.g., any aryl or substituted aryl group, e.g, phenyl, paramethoxyphenyl or naphthyl. When the X moiety is $P(Ar^2)_3$, the $Ar^2$ can be any aryl or substituted aryl group, e.g., phenyl, paramethoxyphenyl or naphthyl. When the X moiety is an isonitrile, $R^3NC$, the $R^3$ can be any $C_{1-6}$ hydrocarbon, e.g., alkyl or substituted alkyl group, e.g., methyl, ethyl, or t-butyl, or, e.g., any aryl or substituted aryl group, e.g., phenyl, paramethoxyphenyl or naphthyl. When the X moiety is $Ar^3NC$, the $Ar^3$ can be any aryl or substituted aryl group, e.g., phenyl, paramethoxyphenyl or naphthyl. When the X moiety is $SR^4$, the $R^4$ can be any $C_{1-6}$ hydrocarbon, e.g., alkyl or substituted alkyl group, e.g., methyl, ethyl, or t-butyl, or, e.g., any aryl or substituted aryl group, e.g., phenyl, paramethoxyphenyl or naphthyl, or the $R^4$ can be $CH_2CH_2SH$. When the X moiety is $P(R^5)_2R^6$, the $R^5$ can be any $C_{1-6}$ hydrocarbon, e.g., alkyl or substituted alkyl group, e.g., methyl, ethyl or t-butyl, or, e.g., any aryl or substituted aryl group, e.g., phenyl, paramethoxyphenyl or naphthyl, and $R^6$ can be $CH_2CH_2P(CH_3)_2$ or any $C_{1-6}$ hydrocarbon, e.g., alkyl or substituted alkyl group, e.g., methyl, ethyl or t-butyl, or, e.g., any aryl or substituted aryl group, e.g., phenyl, paramethoxyphenyl or naphthyl. An is the number of X moieties present, which is the number required to satisfy the valence requirements of the metal, and can be 1, 2, 3 or 4.

Preferred compounds of formula I have the formulas:

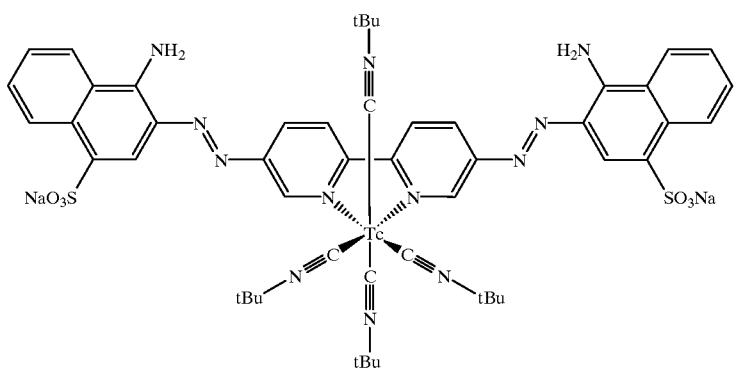

3

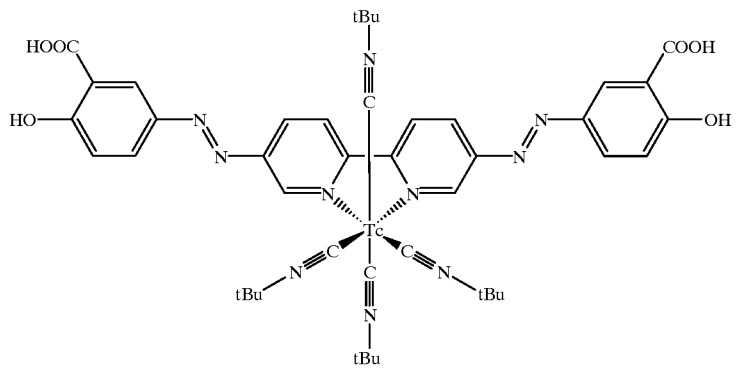
Other preferred compounds of formula I have the formulas:
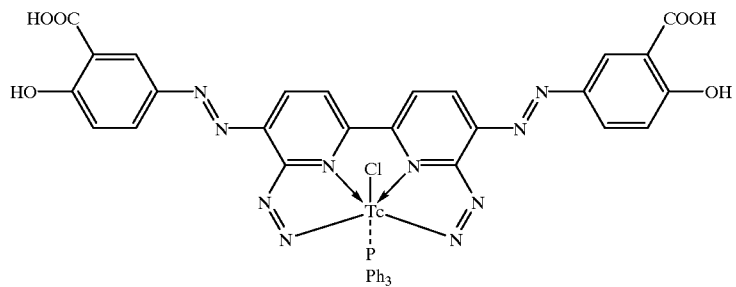
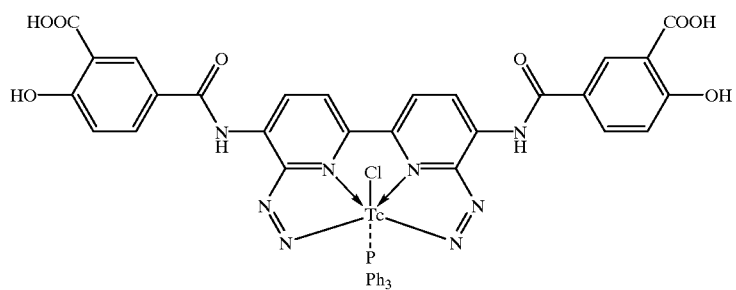
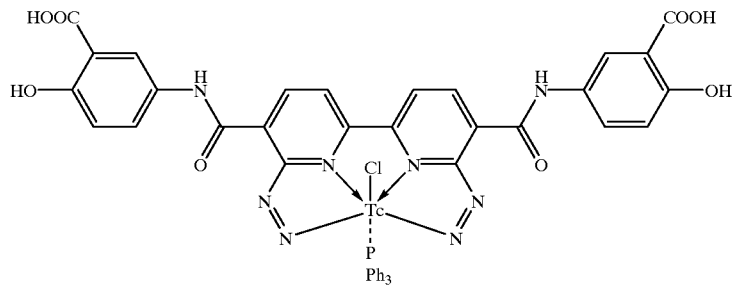

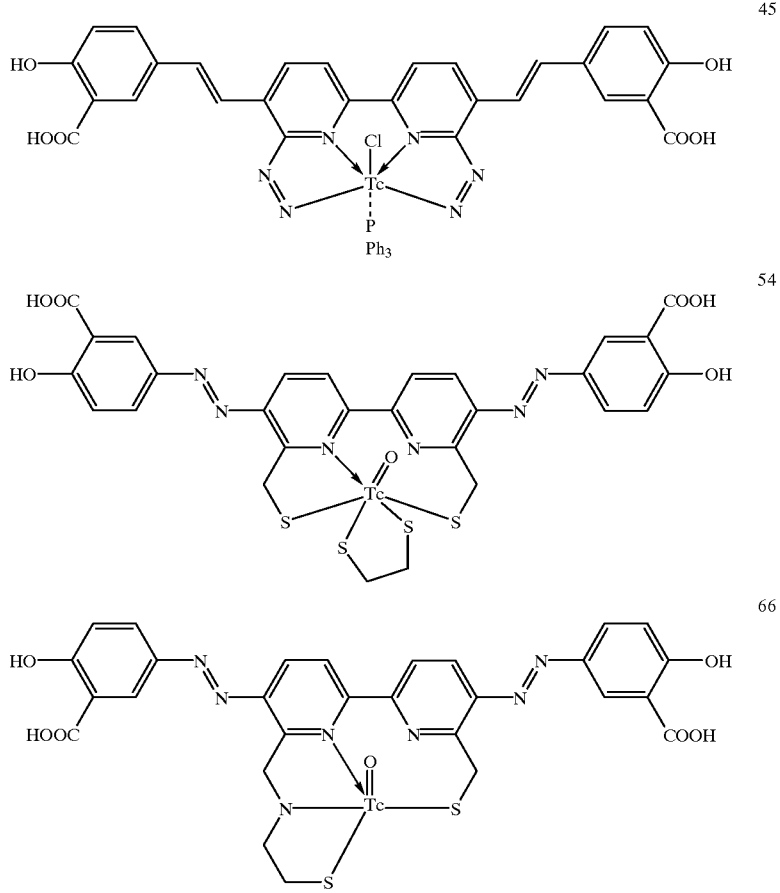

This invention also provides an amyloid binding compound of the formula:

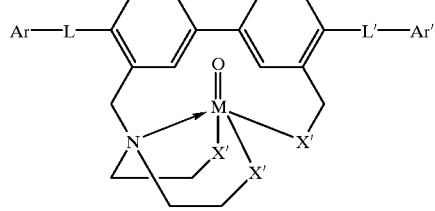

and pharmaceutically acceptable salts thereof, wherein

M is $^{99m}$Tc, $^{111}$In, $^{90}$Y, $^{99}$Tc or $^{186}$Re;

X' is S, NH or O;

L and L' are —N=N—, —CONH—, —NHCO—, —HN—NH—, or —C=C—, and can be the same or different from each other; and Ar and Ar' are

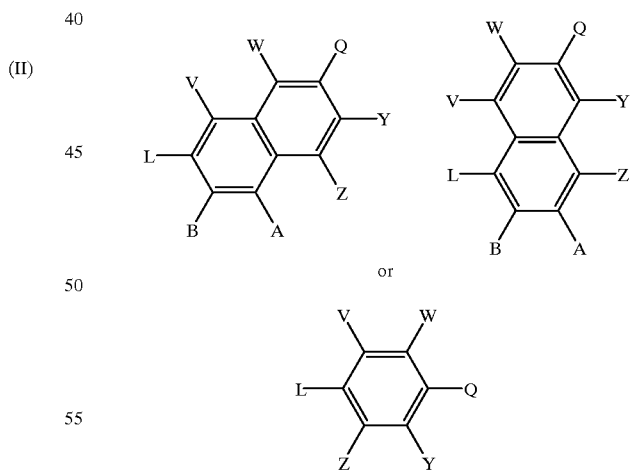

and can be the same or different from each other, where each of V, W, Q, Y, Z, A and B is OH, COOH, H, $R^5$ ($R^5$ is $C_{1-6}$ hydrocarbon), $CO_2R^6$ ($R^6$ is $C_{1-6}$ hydrocarbon), $CONH_2$, CN, $NH_2$, $CH_2NH_2$ or $SO_3$ and can be the same or different from each other.

Compounds of formula II, referred to herein as $NX_3$ compounds, can be used, e.g., in SPECT imaging of amyloid, described herein. An advantage of compounds of formula II is that the metal complex is uncharged and therefore can pass more easily through the blood brain barrier when administered to mammals. The uncharged $^{99m}Tc$ complex is easier to prepare than a charged complex (as, e.g., compounds of formula I), a consideration which influences the practicality of such a reagent for widespread SPECT imaging.

Preferred compounds of formula II have the formulas:

The invention also provides a compound of the formula

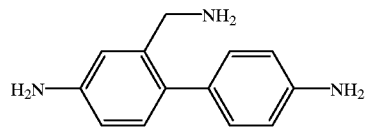

79

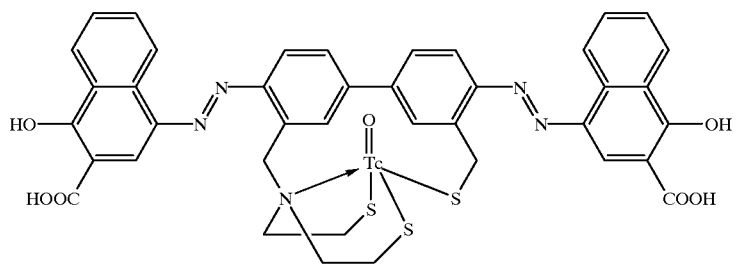

140

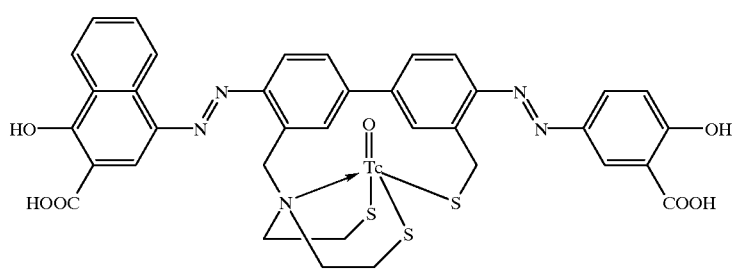

141

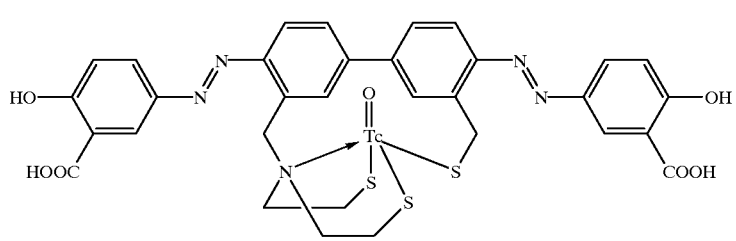

142 and

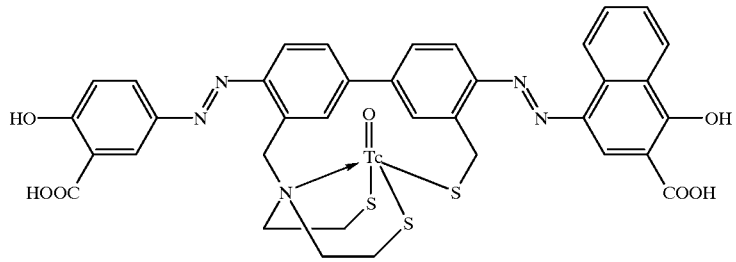

143

The invention also provided a compound of the formula

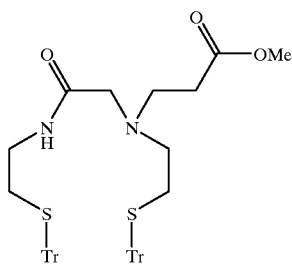
82

The invention also provides a compound of the formula

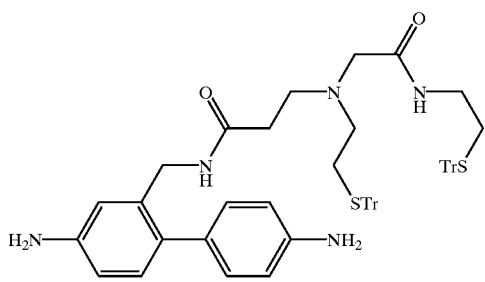
83

Each of the above three compounds can be used to synthesize the amyloid binding compounds of formula II discussed above. In addition, compounds 79 and 82 allow the synthesis of $N_2S_2$ dimers (formula IV) and a type of head-to-tail dimer (formula VIII). Compound 79 also allows the synthesis of fluorescent probes (formulas IX and X).

The invention also provides an amyloid binding compound of the formula

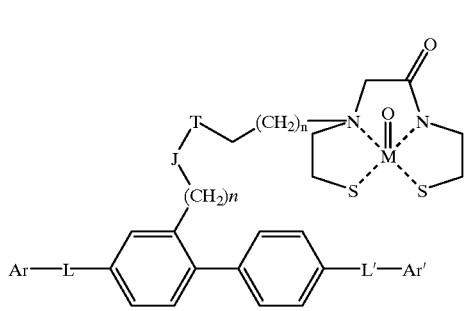
(III)

and pharmaceutically acceptable salts thereof, wherein
J is NH, O or S;
T is CO or $CH_2$;
n is the number 1, 2, 3, 4, 5 or 6;
M is $^{99m}Tc$, $^{111}In$, $^{90}Y$, $^{99}Tc$ or $^{186}Re$;
L and L' are —N=N—, —CONH—, —NHCO—, —HN—NH—, or —C=C—, and can be the same or different from each other; and
Ar and Ar' are

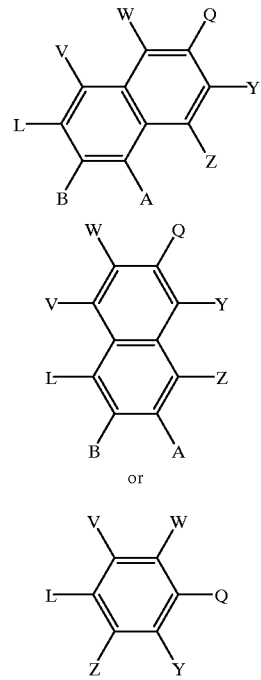

and can be the same or different from each other, where each of V, W, Q, Y, Z, A and B is OH, COOH, H, $R^5$ ($R^5$ is $C_{1-6}$ hydrocarbon), $CO_2R^6$ ($R^6$ is $C_{1-6}$ hydrocarbon), $CONH_2$, CN, $NH_2$, $CH_2NH_2$ or $SO_3$ and can be the same or different from each other.

Compounds of formula III, referred to herein as $N_2S_2$ compounds, can be used, e.g., in SPECT imaging of amyloid, described herein. An advantage of compounds of formula III is that the metal complex is uncharged and therefore can pass more easily through the blood brain barrier when administered to mammals. The uncharged metal complexes are easier to prepare than a charged complex (as, e.g., compounds of formula I), a consideration which influences the practicality of such a reagent for widespread SPECT imaging.

Preferred compounds of formula rII have the formulas:

144
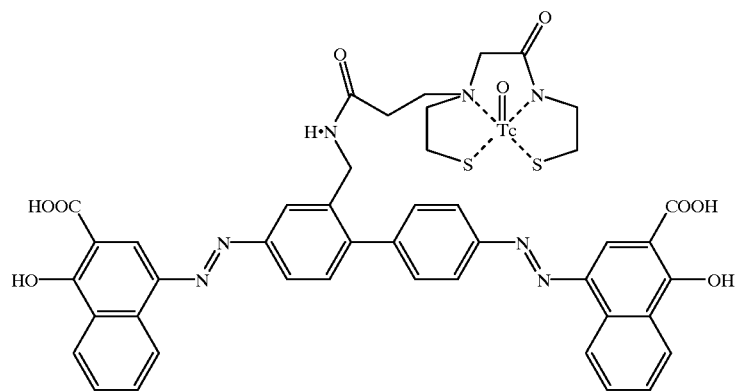
145
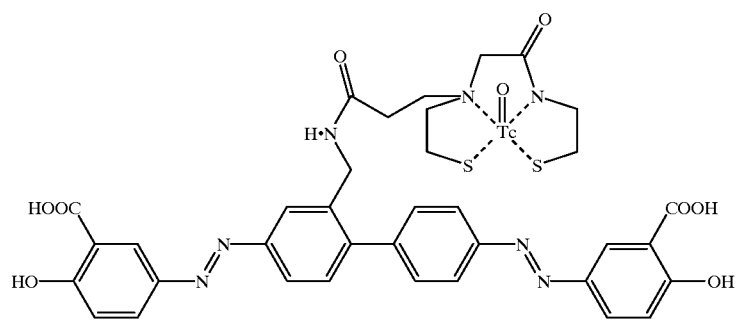
146
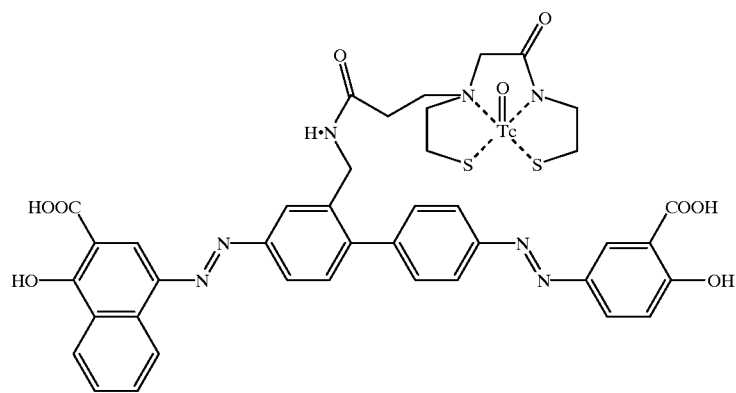
and
147
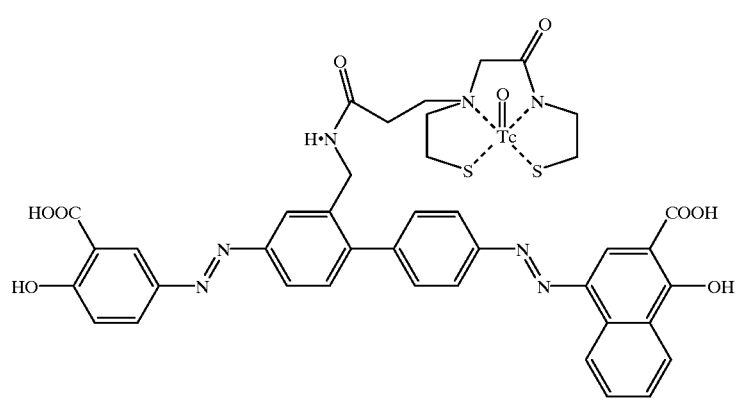

The invention also provides an amyloid binding compound of the formula

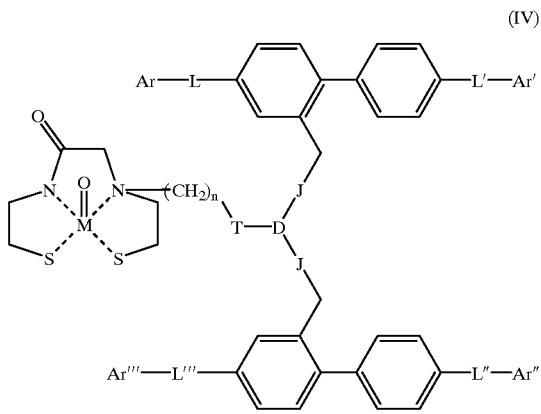

(IV)

and pharmaceutically acceptable salts thereof,
wherein
J is NH or S;
T is CO or CH$_2$;
n is the number 1, 2, 3, 4, 5 or 6;
M is $^{99m}$Tc, $^{111}$In, $^{90}$Y, $^{99}$Tc or $^{186}$Re;
L, L', L" and L'" are —N=N—, —CONH—, —NHCO—, —HN—NH—, or —C=C—, and can be the same or different from each other;
Ar, Ar', Ar" and Ar'" are

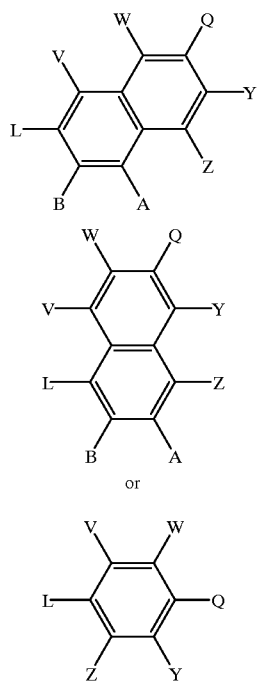

and can be the same or different from each other, where each of V, W, Q, Y, Z, A and B is OH, COOH, H, R$^5$ (R$^5$ is C$_{1-6}$ hydrocarbon), CO$_2$R$^6$ (R$^6$ is C$_{1-6}$ hydrocarbon), CONH$_2$, CN, NH$_2$, CH$_2$NH$_2$ or SO$_3$ and can be the same or different from each other; and when J is NH and T is CO, then D is a trifunctional linker with two carboxyl groups and one amine group; and when J is NH and T is CH$_2$, then D is COCH$_2$(CH$_2$S)CH$_2$CO;

when J is S and T is CO, then D is CH$_2$CH(CH$_2$NH)CH$_2$; and when J is S and T is CH$_2$, then D is CH$_2$CH(CH$_2$S)CH$_2$.

In certain embodiments, when J is NH and T is CO, then D is

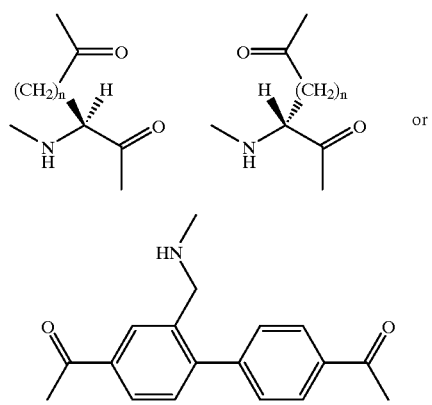

and n is the number 1 or 2.

Preferred compounds of formula IV have the formula:

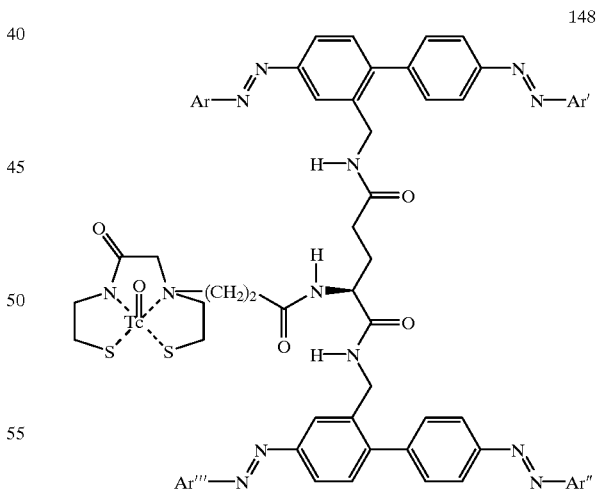

148

Examples of compounds of formula IV include:

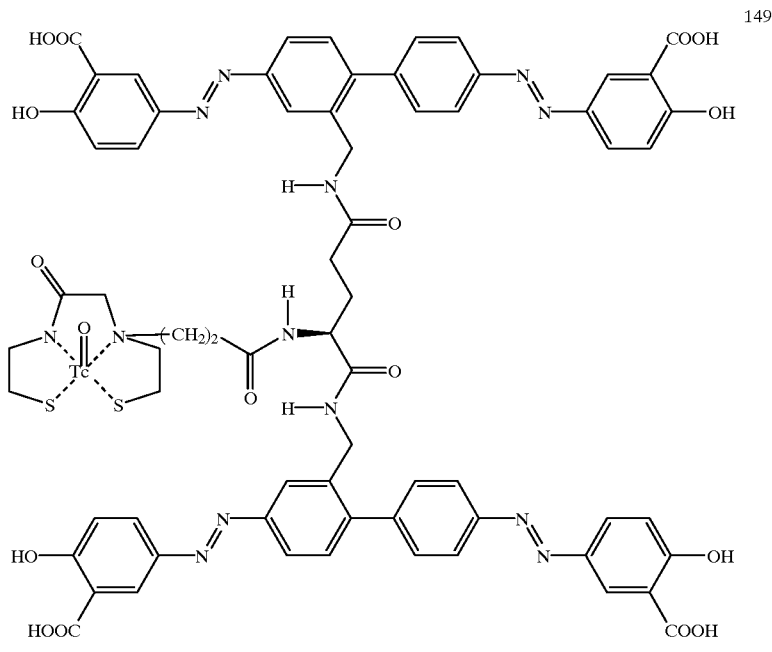

149

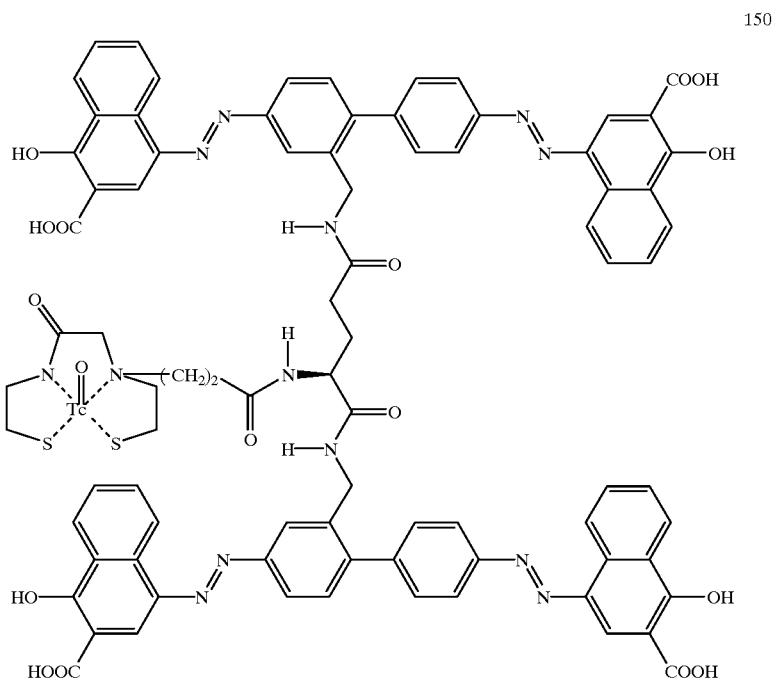

150

Compounds of formula IV ($N_2S_2$ dimers with a trifunctional linker) can be synthesized, e.g., as described in Example 26 or by combinatorial synthesis of libraries as described in Example 31.

Compounds of formula IV can be used, e.g., in SPECT imaging of amyloid, described herein. An advantage of these dimeric compounds is that they can have increased affinity for binding amyloid as compared to the related monomeric compounds.

The invention also provides an amyloid binding compound of the formula

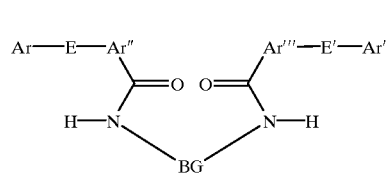

(V)

and pharmaceutically acceptable salts thereof, wherein

BG is any dicarbonyl or dithiocarbonyl moiety;

E and E' are

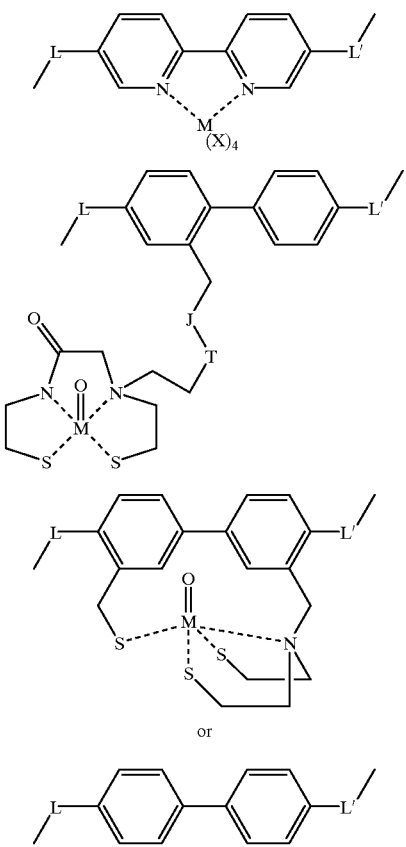

and can be the same or different from each other, wherein

M is $^{99m}$Tc, $^{111}$In, $^{90}$Y, $^{99}$Tc or $^{186}$Re;

L and L' are —N=N—, —CONH—, —NHCO—, —HN—NH—, or —C≡C—, and can be the same or different from each other; and J is NH or S;

T is CO or CH$_2$;

X is Cl, I, Br, F, P(R$^2$)$_3$ (R$^2$ is C$_{1-6}$ hydrocarbon), P(Ar$^2$)$_3$ (Ar$^2$ is aryl or substituted aryl), R$^3$NC (R$^3$ is C$_{1-6}$ hydrocarbon), Ar$^3$NC (Ar$^3$ is aryl or substituted aryl), SR$^4$ (R$^4$ is CH$_2$CH$_2$SH or C$_{1-6}$ hydrocarbon), or P(R$^5$)$_2$R$^6$ (R$^5$ is C$_{1-6}$ hydrocarbon; R$^6$ is C$_{1-6}$ hydrocarbon or CH$_2$CH$_2$P(CH$_3$)$_2$, and each X can be the same or different from each other; and Ar and Ar' are

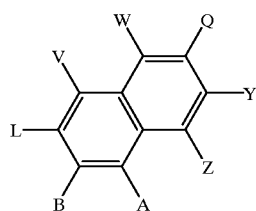

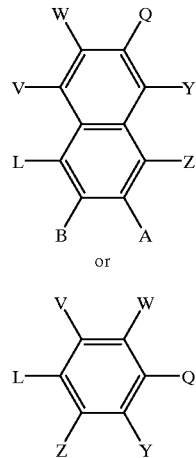

and can be the same or different from each other, where each of V, W, Q, Y, Z, A and B is OH, COOH, H, R$^5$ (R$^5$ is C$_{1-6}$ hydrocarbon), CO$_2$R$^6$ (R$^6$ is C$_{1-6}$ hydrocarbon), CONH$_2$, CN, NH$_2$, CH$_2$NH$_2$ or SO$_3$ and can be the same or different from each other, and Ar″ and Ar‴ are

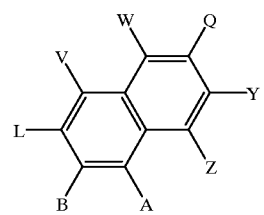

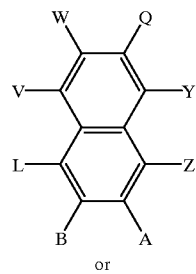

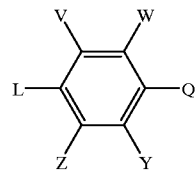

and can be the same or different from each other,, where one of V, W, Q, Y, Z, A and B is COOH and each of the others is OH, COOH, H, R$^5$ (R$^5$ is C$_{1-6}$ hydrocarbon), CO$_2$R$^6$ (R$^6$ is C$_{1-6}$ hydrocarbon), CONH$_2$, CN, NH$_2$, CH$_2$NH$_2$ or SO$_3$ and can be the same or different from each other.

In certain preferred embodiments, BG is CO(CH$_2$)$_n$CO, CS(CH$_2$)$_n$CS, COCH(NH$_2$)(CH$_2$)$_2$CO or COCH(NH$_2$)CH$_2$CO, and n is the number 1–6.

The dimeric compounds of formula V can be synthesized, e.g., directly or by combinatorial synthesis of libraries, as described, e.g., in Example 31. Compounds of formula V can be used, e.g., in SPECT imaging of amyloid, described herein. An advantage of these dimeric compounds is that they can have increased affinity for binding amyloid as compared to the related monomeric compounds.
Preferred compounds of formula V (BIPY dimers) have the formulas:
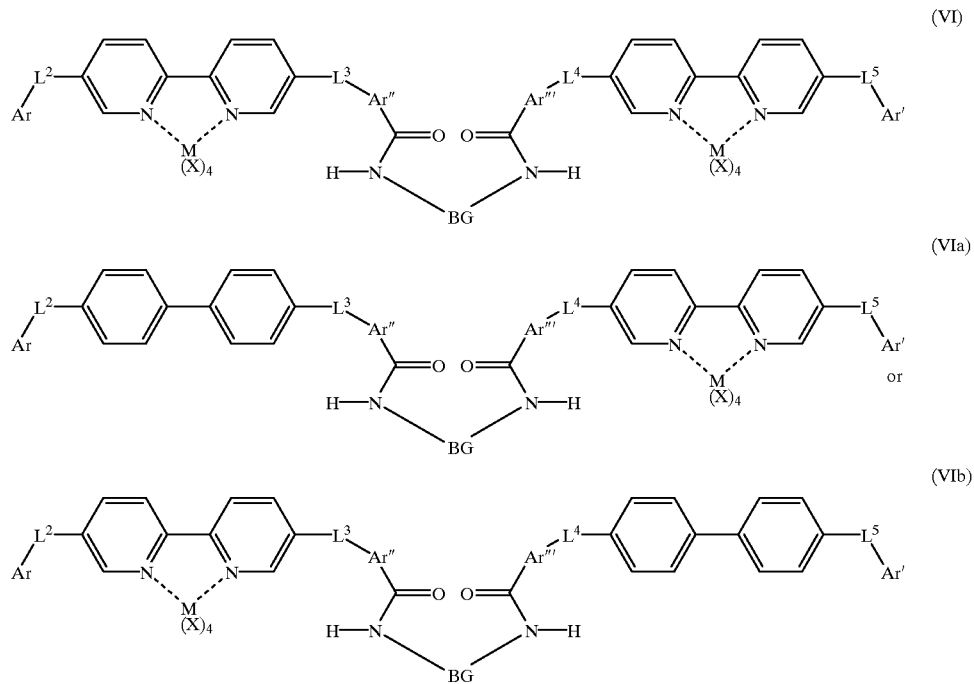
In the above, $L^2$, $L^3$, $L^4$ and $L^5$ are —N=N—, —CONH—, —NHCO—, —HN—NH—, or —C≡C—, and can be the same or different from each other.
Other preferred compounds of formula V ($NX_3$ dimers) have the formulas:
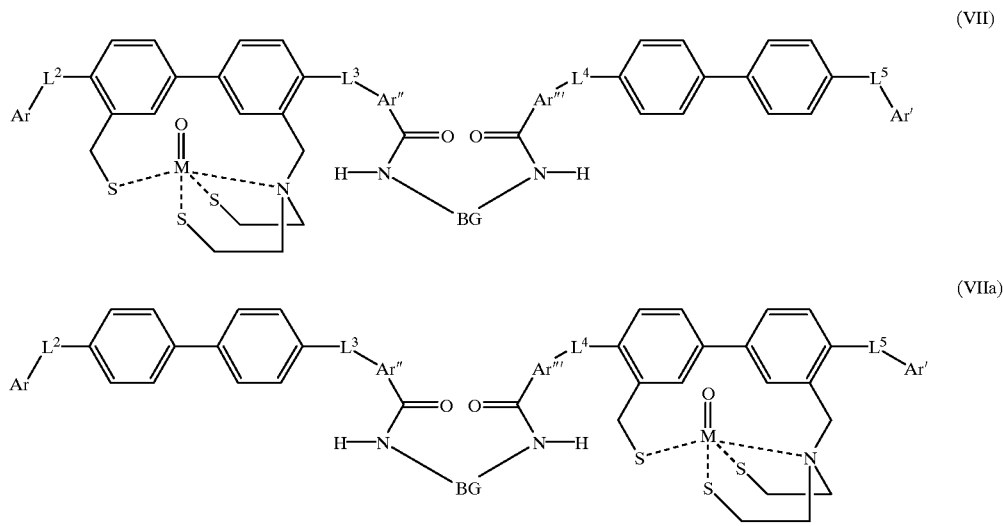

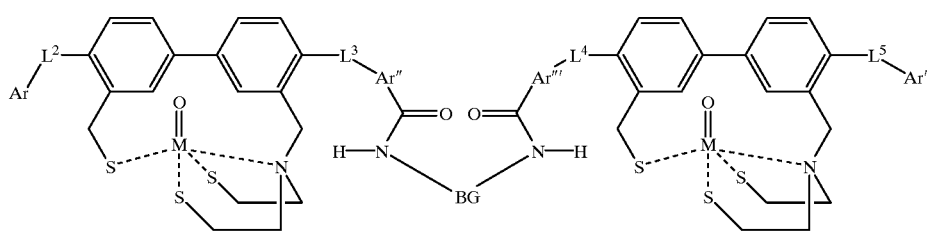
(VIIb)
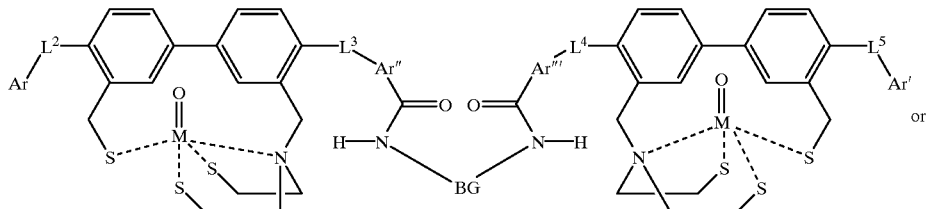
(VIIc)
or
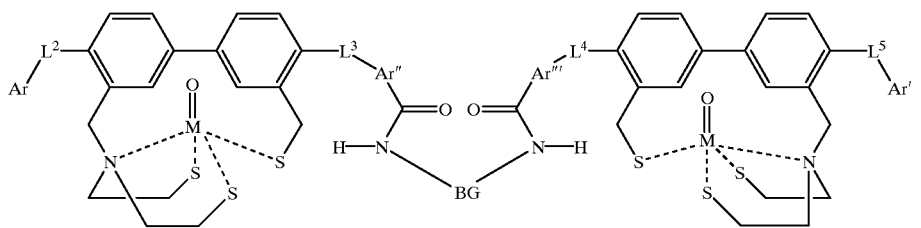
(VIId)
wherein L², L³, L⁴ and L⁵ are —N=N—, —CONH—, —NHCO—, —HN—NH—, or —C=C—, and can be the same or different from each other.
Other preferred compounds of formula V (N$_2$S$_2$ dimers) have the formula:
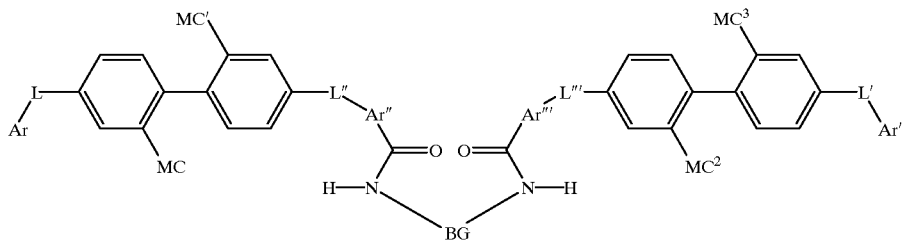
(VIII)
wherein
L², L³, L⁴ and L⁵ are —N=N—, —CONH—, —NHCO—, —HN—NH—, or —C=C—, and can be the same or different from each other; and MC, MC¹, MC² and MC³ are
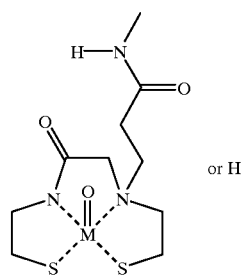
or H where any one of MC, MC¹, MC² or MC³ is a metal binding group and the others are H, or where MC or MC¹ is H and MC² or MC³ is H and the others are a metal binding group.

The invention also provides an amyloid binding compound of the formula

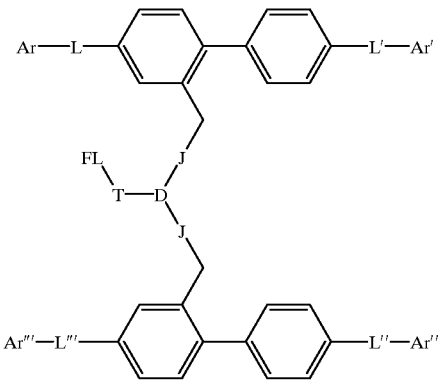

(IX)

and pharmaceutically acceptable salts thereof, wherein

J is NH or S;

T is CO or $C_2$;

FL is fluorescein, rhodamine, coumarin, or any other fluorescent moiety;

L and L' are —N=N—, —CONH—, —NHCO—, —HN—NH—, or —C=C—, and can be the same or different from each other; and Ar and Ar' are

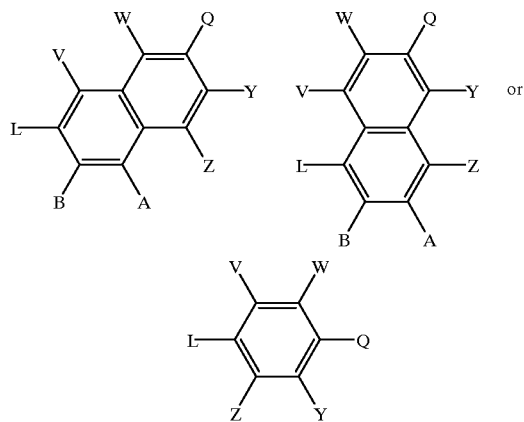

and can be the same or different from each other, where each of V, W, Q, Y, Z, A and B is OH, COOH, H, $R^5$ ($R^5$ is $C_{1-6}$ hydrocarbon), $CO_2R^6$ ($R^6$ is $C_{1-6}$ hydrocarbon), $CONH_2$, CN, $NH_2$, $CH_2NH_2$ or $SO_3$ and can be the same or different from each other.

A preferred compound of the fluorescent dimer of formula IX is

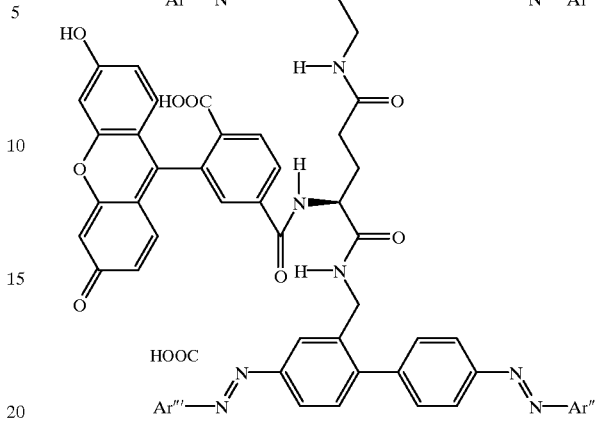

The fluorescent dimeric compounds of formula IX can be used, e.g., to measure aggregated forms of β-amyloid protein in cultured cells, e.g., in an in vitro assay for screening for compounds which inhibit aggregation in a physiologically-relevant location. An advantage of these dimeric compounds is that they have increased affinity for binding amyloid as compared to the related monomeric compounds.

The invention also provides and amyloid binding compound of the formula

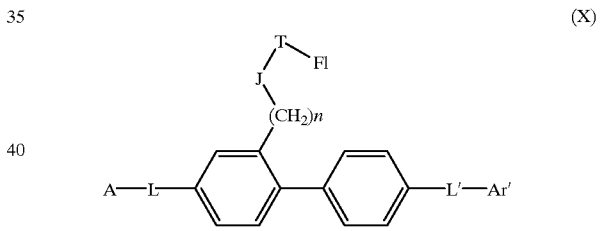

(X)

and pharmaceutically acceptable salts thereof, wherein

J is NH or S;

T is CO or $CO_2$;

FL is fluorescein, rhodamine, coumarin, or any other fluorescent moiety;

L and L' are —N=N—, —CONH—, —NHCO—, —HN—NH—, or —C=C—, and can be the same or different from each other; and Ar and Ar' are

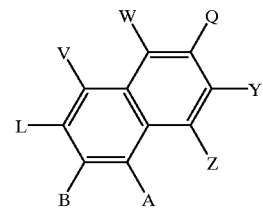

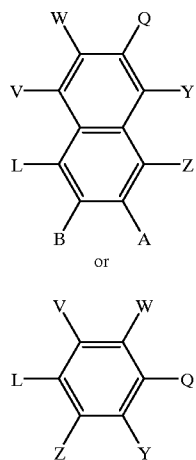

and can be the same or different from each other, where each of V, W, Q, Y, Z, A and B is OH, COOH, H, $R^5$ ($R^5$ is $C_{1-6}$ hydrocarbon), $CO_2R^6$ ($R^6$ is $C_{1-6}$ hydrocarbon), $CONH_2$, CN, $NH_2$, $CH_2NH_2$ or $SO_3$ and can be the same or different from each other.

The fluorescent monomeric compounds of formula X can be used, e.g., to measure aggregated forms of β-amyloid protein in cultured cells, e.g., in an in vitro assay for screening for compounds which inhibit aggregation in a physiologically-relevant location.

This invention also provides a method for diagnosing the degree of progression of Alzheimer's disease in a mammal. A first mammal having Alzheimer's disease and having brain amyloid fibrils is provided. A labeled ligand capable of interacting with the amyloid fibrils is also provided. The labeled ligand is administered to the mammal under conditions which allow the labeled ligand to interact with the amyloid fitirils in the brain so as to result in labeled amyloid fibrils. The localization or quantification of the labeled amyloid fibrils in the mammal is determined by imaging so as to diagnose the degree of progression of the Alzheimer's disease.

Mammal is meant to include human and non-human mammals. Alzheimer's disease is meant to include human Alzheimer's disease and similar diseases in other mammals characterized by Alzheimer's disease-like amyloidosis. Alzheimer's disease is a progressively deteriorating disease which eventually leads to death. A mammal having Alzheimer's disease is meant to include stages of the disease in which the symptoms of the disease are apparent or not apparent.

By amyloid fibril is meant aggregated amyloid protein. Amyloid fibril is meant to include any aggregated precursor, intermediate or mature form of amyloid protein that is formed in vitro or in vivo. Examples of amyloid proteins include β-amyloid, NAC, Islet amyloid polypeptide (IAPP), immunoglobulin G (Ig) light chain, transthyretin, lysozyme, $β_2$-microglobulin and prion protein. β-amyloid proteins are meant to include Aβ1-42 and Aβ1-40 (a C-terminally truncated relative of Aβ1-42), Aβ17-42, Aβ3-42 (pyro Glu), as well as other length β-amyloid peptides. Under certain conditions, amyloid proteins aggregate. Examples of aggregated β-amyloid, i.e., β-amyloid fibrils, include protofibrils, type-1 fibrils, type-2 fibrils, neuritic plaque, diffuse amyloid, and combinations thereof.

Protofibrils are a distinct oligomeric aggregate of β-amyloid which form during the early phases of in vitro fibril formation by synthetic β-amyloid peptides (e.g., Aβ1-40 and Aβ1-42). Using atomic force microscopy (AFM), protofibrils appear as small elongated β-amyloid oligomers which become detec table during the early phase of aggregation and elongate slowly with time before rapidly disappearing following the appearance of prototypical amyloid fibrils. Average protofibril heights measured by AFM are 3.1 nm+0.31 nm for Aβ1-40 and 4.2+0.58 nm for Aβ1-42. Protofibril lengths are similar for both Aβ1-40 and Aβ1-42 and are as short as 20 nm at early time points and gradually increase with longer incubation times to reach lengths commonly exceeding 200 nm. These protofibrils are further characterized by small periodic increases in diameter with a periodicity of 20–22 nm which are observed by AFM for both Aβ1-40 and Aβ1-42. The protofibril is the precursor to the type-1, type-2 and neuritic β-amyloid fibrils. In a preferred embodiment, it is the protofibrils in the mammal that interact with the labeled ligand.

Type-1 and type-2 fibrils are formed during in vitro synthesis of β-amyloid peptides and are examples of prototypical β-amyloid fibrils. Type-1 and type-2 fibrils have lengths rarely less than about 1 μm and often greater than about 5 μm, as observed using AFM. Type-1 fibrils have larger apparent diameters than protofibrils (7.8+0.45 nm for Aβ1-40 and 7.3+0.53 nm for Aβ1-42), and a left-handed helical twist that creates periodic increases in diameter along the long axis of the fibril with a period of approximately 43 nm (for both Aβ1-40 and Aβ1-42). Type-1 fibrils may be composed of prcotofibrils wrapped around each other. Type-2 fibrils have average heights measured by AFM of about 4–6 nm. Type-2 lack the period increases in diameter which characterize both protofibrils and type-1 fibrils. Instead, they display discontinuities at less regular intervals, often in excess of 100 nm, which make the fibrils appear to be composed of smooth segments assembled linearly with the ends slightly offset.

Neuritic plaques contain aggregated β-amyloid fibrils, e.g., type-1 and type-2 fibrils and protofibrils. Neuritic plaques have classically been defined as the disease-associated fibrils in, e.g., Alzheimer's disease. Postmortem brains of persons having Alzheimer's disease are characterized by the presence of such β-amyloid neuritic plaques. In Alzheimer's disease, the predominant brain amyloid proteins are Aβ1-42 and its C-terminally truncated relative Aβ1-40.

By diffuse amyloid is meant Aβ1-40 and Aβ1-42 aggregates that appear amorphous using electron microscopy. Diffuse amyloid characterizes the brains of individuals who are predisposed to Alzheimer's disease. Diffuse amyloid does not contain type-1 or type-2 fibrils, but may contain protofibrils which cannot be detected by electron microscopic examination of diseased tissue. Detection of protofibrils thus can provide a method for detecting aggregated β-amyloid earlier than is possible by targeting later-stage fibrils, and therefore can be used as a diagnostic tool for identifying individuals predisposed to Alzheimer's disease. Stabilization of the protofibril intermediate can also inhibit formation of later-stage fibrils.

The ligand of this invention is capable of interacting with amyloid fibrils. In certain embodiments, the ligand is capable of interacting specifically with brain amyloid fibrils. In certain embodiments, the ligand is capable of interacting specifically with only certain types of amyloid fibrils, e.g., it interacts with β-amyloid protofibrils, but not with β-amyloid fibrils, or it interacts with type-1 or type-2 β-amyloid fibrils but not with diffuse amyloid. Interacts is meant to include, e.g., binds, complexes, associates, or conjugates. In certain embodiments, the ligand is, e.g., an aromatic azo dye, e.g., an analog of Congo Red or Chrysamine G. Preferably, the ligand is an organometallic ligand. By organometallic ligand is meant a ligand which has organic parts and metallic parts.

Any label whose presence in the mammal can be determined by non-invasive procedures can be used. For example, the label in the labeled ligand can be a gamma emitter. Preferred gamma emitters are technetium-99m, indium-111, yttriurn-90 and rhenium-186. Technetium-99m is most preferred. A preferred beta emitter is technetium-99. Preferably, the labeled liganad is an organometallic ligand.

In a preferred embodiment, the labeled ligand is a compound of formula I, or a pharmceutically acceptable salt thereof described above. Preferred compounds of formula I are compounds of formulas 3, 6, 15, 28, 35, 45, 54 and 66, or pharmaceutically acceptable salts thereof, described above. Most preferred compounds of formula I are formulas 3 or 6, or a pharmaceutically accept able salt thereof.

other preferred compounds are compounds of formulas II or III or pharmaceutically acceptable salts thereof, described above. Examples of compounds of formula II are 140–143, and examples of compounds of formula III are 144–147, described above. Most preferably, the compounds are the dimers of formula IV or V, or pharmaceutically acceptable salts thereof, described above.

Dimers are preferred because Congo Red does not specifically stain amyloid in Alzheimer's disease brain tissue. Rather, it is concentrated in plaque and appears as a green stain when a tissue section is viewed under polarized light. This phenomenon, known as birefringence, is specific to amyloid and arises because the Congo Red molecules are aligned in an ordered array along the fibril surface. It is believed that other interactions of Congo Red in tissue involve 1:1 interactions. The specificity of ordered multivalent binding is exploited by the covalent dimers of the compounds of this invention without being bound by any theory, these dimers should exhibit increased affinity for the fibril surface, but not have increased affinity for nonspecific, i.e., 1:1, binding partners. The increased affinity results from the fact that the covalent dimer loses less entropy on binding (i.e., the entropy of binding will be less unfavorable) than do two separate molecules. Accordingly, covalent dimers in which the two Congo Red-based subunits are rigidly held in the geometry required for fibril binding, should lose no entropy on binding and therefore have an even greater affinity. The rigidification of the dimer "linker" can be accomplished by the combinatorial approach discussed infra. The entropic advantage enjoyed by the dimer is even greater for trimers or higher oligomers. Trimers and higher oligomers are also meant to be covered by this invention. Trimers can be prepared using similar chemistry as for the synthesis of the dimers.

In certain embodiments, the labeled ligand is capable of interacting specifically with brain amyloid fibrils. In preferred embodiments, the labeled ligand is capable of interacting specifically with one kind of amyloid fibril, e.g., type-1 fibrils or type-2 fibrils. Most preferably, the labeled ligand is capable of interacting specifically with β-amyloid protofibrils.

Administration of the labeled ligand into the mammal can be accomplished by any method which allows the labeled ligand to interact with amyloid fibrils in the brain so as to result in labeled amyloid fibrils. These methods include, e.g., injection, infusion, deposition, implantation, oral ingestion or topical administration, or any other method of administration where access to the brain by the labeled ligand is obtained. Preferably, administration is by injection. Injections can be, e.g., intravenous, intradermal, subcutaneous, intramuscular or intraperitoneal. Single or multiple administrations of the ligand can be given. In certain embodiments, a combination of different ligands are given. In other embodiments, the labeled ligand can be administered with one or more additional materials.

The labeled ligand can be in a liquid, e.g., in dissolved form or colloidal form. The liquid can be a solvent, partial solvent or non-solvent. In many cases, water or an organic liquid can be used.

The dose of the labeled ligand that is administered is determined in part by the amount of radioactivity that is desirable to administer. The amount of radioactivity depends upon the isotope used and can be determined by one skilled in the art without undue experimentation. For example, it is preferred to use about 0.1 mCi/dose to about 100 mCi/dose.

The labeled ligand needs to cross the blood brain barrier so as to reach the brain. By blood brain barrier is meant capillary endothelial cells with continuous tight junctions and with no detectable transendothelial pathways. Such structures provide a cellular barrier between the blood and the interstitial fluid, thus controlling the exchange of materials between the blood and the central nervous system. In certain embodiments, the labeled ligand itself is able to cross the blood brain barrier. See, e.g., Tubis et al., J. Am. Pharmaceutical Assoc. 49:422–425 (1960), which reports that a tetra-iodinated form of Congo Red crosses the blood brain barrier to the extent of 0.03% of a peritoneally injected dose. Such an amount results in nM levels of the compound in the brain, which is sufficient for SPECT imaging. It is preferred to use electrically neutral ligands to cross the blood brain barrier. Examples of electrically neutral compounds of this invention are compounds of formulas II, III and IV, and some versions of V, VII and VIII. In other embodiments, materials are administered so as to aid the labeled ligand to cross the blood brain barrier. For example, mannitol, an organic solvent, certain drugs, or RMP-7 can be used to copen the blood brain barrier so as to allow the labeled ligand to enter. Any method for opening the blood brain barrier known to those skilled in the art can be used in this invention.

The labeled ligand interacts with the amyloid fibrils in, e.g., the brain, so as to result in labeled amyloid fibrils. The localization or quantification of the labeled amyloid fibrils is determined by imaging. By imaging is meant the detection of the distribution of the label in the body by non-invasive means. Examples of imaging include radioimaging, magnetic resonance imaging and single photon emission computed tomographic imaging. The presence of gamma emitters can be determined, e.g., by a gamma camera or a single photon emission computed tomography (SPECT) camera. The presence of positron emitters can be determined, e.g., by a positron emission tomographic (PET) camera. These imaging techniques are known to those skilled in the art. The imaging can be a total body scan or a partial body scan, e.g., of the brain. The timing after administration of the labeled ligand for a scan can be minutes, hours, days or weeks.

Depending upon the localization and/or quantification of the labeled amyloid fibrils, a diagnosis is made regarding the degree of progression of the Alzheimer's disease. In certain embodiments, the localization or quantification ofE the labeled amyloid fibrils is compared to a standard. The standard can be, e.g., the localization or quantification pattern of a second mammal not having Alzheimer's disease, or the localization or quantification pattern obtained from an earlier determination of the first mammal.

The invention also provides a method for monitoring the response to a therapy in a mammal having Alzheimer's disease. A mammal having Alzheimer's disease and having brain amyloid fibrils is provided. The mammal is treated with a therapy for Alzheimer's disease. The response of the mammal to the treating step is monitored by determining whether the therapy alters the localization or quantification of the amyloid fibrils in the mammals.

Therapy is meant to include, e.g., compounds, mixtures of compounds, radiation, ultrasound, or any other type of treatment which can alleviate Alzheimer's disease.

In certain embodiments, the labeled ligand is capable of interacting specifically with brain amyloid fibrils. In preferred embodiments, the labeled ligand is capable of interacting specifically with one kind of amyloid fibril, e.g., type-1 fibrils or type-2 fibrils. Most preferably, the labeled ligand is capable of interacting specifically with β-amyloid protofibrils.

In preferred embodiments, the determining step comprises providing a labeled ligand capable of interacting with the amyloid fibrils. The labeled ligand is administered to the mammal under conditions which allow the labeled ligand to interact with the amyloid fibrils in the brain so as to result in labeled amyloid fibrils. The localization or quantification of the labeled amyloid fibrils in the mammal is determined by imaging. Preferably, the labeled ligand is a compound of formula I, or a pharmaceutically acceptable salt thereof, described above. Preferred compounds of formula I are compounds of formulas 3, 6, 15, 28, 35, 45, 54 or 66, or a pharmaceutically acceptable salt thereof, described above. Other preferred compounds are compounds of formulas II or III or pharmaceutically acceptable salts thereof, described above. Examples of compounds of formula II are 140–143, and examples of compounds of formula III are 144–147, described above. Most preferably, the compounds are the dimers of formula IV or V, or pharmaceutically acceptable salts thereof, described above.

The invention also provides a method for evaluating the ability of an agent to alter the localization or quantification of brain amyloid fibrils in a mammal. A mammal having brain amyloid fibrils is provided. An agent is provided. The agent is administered to the mammal and it is determined whether the agent alters the localization or quantification of the brain amyloid fibrils in the mammal.

Altering is meant to include directly or indirectly altering the localization or quantification of brain amyloid fibrils. For example, an agent can affect some condition or factor which in turn affects the localization or quantification of brain amyloid fibrils, or the agent can directly affect the localization or quantification.

The agent being tested can be, e.g., a putative therapeutic agent for a disease, e.g., Alzheimer's disease, or it can be a putative agent which alters other abnormal states-which affect localization or quantification of brain amyloid fibrils, or it can be a putative agent which alters the normal localization or quantification of brain amyloid fibrils. Agents can include, e.g., proteins, peptides, carbohydrates, polysaccharides, glycoproteins, nucleic acids, peptidomimetics, organic molecules (preferably, less than 1500 kDa), fragments or recombinant forms of the above, or any other type of compound which can be administered to the mammal. Agents are also meant to include, e.g., ionizing radiation, non-ionizing radiation and ultrasound. Agents include, e.g., inhibitors or activators of a molecule that is either required for, or inhibits, the synthesis, post-translational modification or functioning of some element involved in the localization or quantification of amyloid. Agents can, e.g., regulate the spatial or temporal control of expression of a gene product. Agents can include, e.g., cytokines, growth factors, hormones, signaling components, kinases, phosphatases, homeobox proteins, transcription factors, translation factors and post-translational factors or enzymes. Agents can, e.g., make modifications, e.g., chemical, charge or shape modifications, in the amyloid or some other element. Agents can, e.g., affect the interaction between two or more cellular or extra-cellular components. The agent can, e.g., act directly or indirectly on the amyloid so as to alter the localization or quantification of the amyloid. The agent can be specific or non-specific for affecting amyloid localization or quantification. The agents of the invention are meant to include reversible and non-reversible agents.

Administration of the agent can be accomplished by any method which allows the agent to reach its target. These methods include, e.g., injection, infusion, deposition, implantation, suppositories, oral ingestion, inhalation or topical administration, or any other method of administration where access to the target by the agent is obtained. Injections can be, e.g., intravenous, intradermal, subcutaneous., intramuscular or intraperitoneal. Implantation includes inserting implantable drug delivery systems, e.g, microspheres, hydronels, polymeric reservoirs, cholesterol matrices, polymeric systems, e.g., matrix erosion and/ or diffusion systems and non-polymeric systems, e.g., compressed, fused or partially fused pellets. Suppositories include glycerin suppositories oral ingestion doses can be enterically coated. Inhalation includes administering the agent with an aerosol in an inhalator, either alone or attached to a carrier that can be absorbed.

The agent can be suspended in a liquid, e.g, in dissolved form or colloidal form. The liquid can be a solvent, partial solvent or non-solvent. In many cases water or an organic liquid can be used.

Administration of the agent can be alone or in combination with other therapeutic agents or other materials. In certain embodiments, materials are administered so as to aid the agent in crossing the blood brain barrier. In certain embodiments, the agent can be combined with a suitable carrier, e.g., a pharmaceutically acceptable carrier, incorporated into a liposome, or incorporated into a polymer release system.

In certain embodiments of the invention, the administration can be designed so as to result in sequential exposures to the agent over some time period, e.g., hours, days, weeks, months or years. This can be accomplished by repeated administrations of the agent by one of the methods described above, or alternatively, by a controlled release delivery system in which the agent is delivered to the mammal over a prolonged period without repeated administrations. By a controlled release delivery system is meant that total release of the agent does not occur immediately upon administration, but rather is delayed for some time period. Release can occur in bursts or it can occur gradually and continuously. Administration of such a system can be, e.g., by long acting oral dosage forms, bolus injections, transdermal patches and sub-cutaneous implants.

Examples of systems in which release occurs in bursts include, e.g, systems in which the agent is entrapped in liposomes which are encapsulated in a polymer matrix, the liposomes being sensitive to a specific stimuli, e.g., temperature, pH, light or a degrading enzyme, and systems in which the agent is encapsulated by an ionically-coated microcapsule with a microcapsule core-degrading enzyme. Examples of systems in which release of the agent is gradual and continuous include, e.g., erosional systems in which the agent is contained in a form within a matrix, and diffusional systems in which the agent permeates at a controlled rate, e.g., through a polymer. Such sustained release systems can be, e.g., in the form of pellets or capsules.

In preferred embodiments, the localization and quantification is determined by the methods described above. The localization or quantification is altered if, e.g., it differs from a standard localization or quantification pattern. The standard used can be, e.g., the pattern obtained from the same mammal when the agent is not present in the mammal, or the pattern obtained from another mammal.

Preferably, the labeled ligand is a compound of formula I or a pharmaceutically acceptable salt thereof, described above. Preferred compounds of formula I are compounds of formulas 3, 6, 15, 28, 35, 45, 54 or 66, or a pharmaceutically acceptable salt thereof, described above. Other preferred compounds are compounds of formulas II or III or pharmaceutically acceptable salts thereof, described above. Examples of compounds of formula II are 140–143, and examples of compounds of formula III are 144– 147, described above. Most preferably, the compounds are the dimers of formula IV or V, or pharmaceutically acceptable salts thereof, described above.

In certain embodiments, the labeled ligand is capable of interacting specifically with brain amyloid fibrils. In preferred embodiments, the labeled ligand is capable of interacting specifically with one kind of amyloid fibril, e.g., type-1 fibrils or type-2 fibrils. Most preferably, the labeled ligand is capable of interacting specifically with β-amyloid protofibrils.

The invention also includes a method for identifying an agent useful for treating a mammal having a disease associated with aggregated amyloid. A mammal having such a disease and having amyloid fibrils is provided. An agent is provided and administered to the mammal. It is determined if the agent alters the localization or quantification of the amyloid fibrils in the mammal. An alteration in the localization or quantification which results in a localization or quantification more similar to that of a mammal which does not have the disease is correlated with the agent being useful for treating the mammal having the disease. Treating is meant to include, e.g., preventing, treating, reducing the symptoms of, or curing the disease.

The disease can be any disease which is associated with aggregated amyloid, e.g., Alzheimer's disease (aggregated β-amyloid), type II diabetes (aggregated Islet amyloid polypeptide), B-cell lymphoma (aggregated Ig light chain), Creutzfeldt-Jacob disease or bovine spongiform encephelopathy (aggregated prion protein), familial transthyretin amyloidosis (aggregated transthyretin), complications from dialysis (aggregated $\beta_2$-microglobulin), or other systemic amyloidoses (e.g., aggregated lysozyme), e.g., serum amyloid A systemic amyloidosis.

In preferred embodiments, the disease is Alzheimer's disease. In such embodiments, it is preferred that the labeled ligand is capable of interacting specifically with brain amyloid fibrils, preferably with one kind of amyloid fibril, e.g., type-1 fibrils or type-2 fibrils, and most preferably with β-amyloid protofibrils.

In preferred embodiments, the localization and quantification is determined by the methods described above. Preferably, the labeled ligand is a compound of formula I or a pharmaceutically acceptable salt thereof, described above. Preferred compounds of formula I are compounds of formulas 3, 6, 15, 28, 45, 54 or 66, or a pharmaceutically acceptable salt thereof, described above. Other preferred compounds are compounds of formulas II or III or pharmaceutically acceptable salts thereof, described above. Examples of compounds of formula II are 140–143, and examples of compounds of formula III are 144–147, described above. Most preferably, the compounds are the dimers of formula IV or V, or pharmaceutically acceptable salts thereof, described above. Administration of the agent is as described above.

The invention also includes the agent obtainable by this method.

The invention further includes a method for determining the localization or quantification of amyloid fibrils in a mammal. A mammal having amyloid fibrils is provided. An organometallic ligand capable of interacting with the amyloid fibrils is provided. The organometallic ligand is administered to the mammal under conditions which allow the organometallic ligand to interact with the amyloid fibrils so as to result in organometallic ligand-amyloid fibril complexes. The localization or quantification of the complexes is determined in the mammal.

The amyloid fibrils can be anywhere in the body of the mammal. For example, the amyloid fibrils can be in the brain, pancreas, vasculature, spleen, liver, kidneys, adrenals, lymph nodes, muscle, cardiovascular system, skin, or any combination thereof. The organometallic ligands of this invention are useful, e.g., for detecting amyloid plaques characteristic of degenerating tissue, e.g., from Alzheimer's disease in the brain, type II diabetes in the pancreas, B-cell lymphoma in the vasculature, Creutzfeldt-Jacob disease in the brain, familial transthyretin amyloidosis in the liver and other peripheral sites, or complications from dialysis in the kidneys.

The organometallic ligands of this invention can have different relative affinities for the different types of amyloid fibrils. Thus, in addition to the general affinity of the organometallic ligands for all amyloid fibrils, there is a specific component to the affinity which depends on precise interactions between the organometallic ligand and the amyloid fibril. Therefore, certain of the organometallic ligands of this invention can be used to distinguish amyloid fibrils of different composition, e.g., the brain amyloid proteins β1-40 and NAC. NAC is a minor brain amyloid protein. NAC may represent up to 10% by moles of Alzheimer's disease brain amyloid fibrils. NAC fibrils seed polymerization of β1-40 in vitro and vice versa. Han et al., Chem. Biol. 2:163–169 (1995).

In certain embodiments, the labeled ligand is capable of interacting specifically with brain amyloid fibrils. In preferred embodiments, the labeled ligand is capable of interacting specifically with one kind of amyloid fibril, e.g., type-1 fibrils or type-2 fibrils. Most preferably, the labeled ligand is capable of interacting specifically with β-amyloid protofibrils.

In preferred embodiments, the localization and quantification is determined by the methods described above. Preferably, the organometallic ligand is a compound of formula I or a pharmaceutically acceptable salt thereof, described above. Preferred compounds of formula I are compounds of formulas 3, 6, 15, 28, 45, 54 or 66, or a pharmaceutically acceptable salt thereof, described above. Other preferred compounds are compounds of formulas II or III or pharmaceutically acceptable salts thereof, described above. Examples of compounds of formula II are 140–143, and examples of compounds of formula III are 144– 147, described above. Most preferably, the compounds are the dimers of formula IV or V, or pharmaceutically acceptable salts thereof, described above. The complexes formed between the organometallic ligand and the amyloid fibril can result from, e.g., bonding, associating, complexing or conjugating. It is preferred that the determining step is by imaging.

In certain embodiments, the administering and determining steps are repeated after a time interval so as to establish a time course for the localization or quantification of the complexes in the mammal. Preferably the time intervals are about 1 minute to about 24 hours, most preferably they are about 30 minutes to about 6 hours. These steps can be repeated one or more times.

In certain embodiments, the mammal is deceased, and the administering step is, e.g., to the postmortem brain or a portion thereof. In such embodiments, the determining step can be, e.g., by autoradiography, SPECT, PET or magnetic resonance imaging.

The invention also includes a method for treating Alzheimer's disease in a mammal. A mammal having Alzheimer's disease is provided. The mammal has non-aggregated amyloid proteins or aggregated amyloid proteins, or combinations thereof. An organometallic ligand capable of interacting with the non-aggregated amyloid proteins, or with the aggregated amyloid proteins, or with both of the amyloid proteins, is provided. A therapeutically effective amount of the organometallic ligand is administered to the mammal under conditions which allow the organometallic ligand to interact with the non-aggregated amyloid proteins, or with the aggregated amyloid proteins, or with both of the amyloid proteins, so as to inhibit aggregation of the amyloid proteins such that treatment of the Alzheimer's disease occurs.

Aggregated amyloid proteins is meant to include fully or partially aggregated amyloid proteins. By partially aggregated amyloid proteins is meant that aggregation of additional amyloid proteins onto the existing aggregated amyloid proteins, e.g., protofibrils or fibrils, can occur under the appropriate conditions. In certain embodiments, the aggregated amyloid proteins are Alzheimer's disease associated β-amyloid fibrils. In certain embodiments, the aggregated amyloid proteins are protofibrils, type-1 fibrils, type-2 fibrils, neuritic plaque, diffuse amyloid, or combinations thereof.

By inhibit aggregation is meant, e.g., that the amyloid proteins are unable to properly interact with each other to effect, e.g., formation of, or growth of, aggregates of amyloid proteins, e.g, the growth of protofibrils, the conversion of protofibrils into fibrils, the growth of fibrils and the growth of neuritic plaque. Inhibiting interaction is also meant to include reversing aggregation of the amyloid proteins.

In a preferred embodiment, the organometallic ligand specifically interacts with β-amyloid protofibrils. Stabilization or inactivation of the protofibril inhibits formation of later-stage fibrils.

Preferably, the organometallic ligand is a compound of formula I or a pharmaceutically acceptable salt thereof, described above. Other preferred compounds are compounds of formulas II and III describe above. Most preferred compounds are the dimers of formula IV or V described above. It is preferred that a non-radioactive organometallic ligand is used for treatment, so as to avoid potential toxicity from high dosages of radioactive organometallic ligands. Examples of non-radioactive metals that can be used in compounds of formula I and VI include Cd, Zn, Co, Cu. Fe, Ni, or combinations thereof. Oxo forms of these metals can also be used. The concentration of the organometallic ligand that is administered is at a dose about 1 to about 1500 mg/kg body weight. Preferably, the dose is about 2 to about 200 mg/kg body weight. Most preferably, the dose is about 2 to about 20 mg/kg body weight. Preferably, the dosage form is such that it does not substantially deleteriously affect the mammal.

Administration of the organometallic ligand is as described above. By therapeutically effective amount is meant that amount which is capable of at least partially preventing or reversing aggregation of the amyloid proteins. A therapeutically effective amount can be determined on an individual basis and will be based, at least in part, on consideration of the species of mammal, the mammal's size, the organometallic ligand used, the type of delivery system used, the time of administration relative to amyloid protein aggregation formation, and whether a single, multiple, or controlled release dose regimen is employed. A therapeutically effective amount can be determined by one of ordinary skill in the art employing such factors and using no more than routine experimentation.

In certain embodiments, the treatment can be assessed by determining the localization and/or quantification of any remaining amyloid fibrils after treatment, by the methods described above. Treating is meant to include, e.g., preventing, treating, reducing the symptoms of, or curing the disease.

The invention also includes a method for treating Alzheimer's disease in a mammal that is similar to the method described above, except that the ligands used are compounds of formulas II, III, IV and V, or pharmaceutically acceptable salts thereof, without any metals bound to them.

The invention also includes a pharmaceutical composition for treating Alzheimer's disease in a mammal comprising a therapeutically effective amount of an organometallic ligand, the ligand being able to interact with amyloid proteins in a mammal in need of treatment for Alzheimer's disease, and a pharmaceutically acceptable carrier. Preferably, the organometallic ligand is a compound of formula I or a pharmaceutically acceptable salt thereof, described above. More preferred compounds are compounds of formulas II or III described above. Most preferably, the compounds are the dimers of formula IV or V described above. Pharmaceutical compositions for treating other diseases associated with aggregated amyloid are also included in this invention. Preferably, non-radioactive organometallic ligands are used.

The invention also includes pharmaceutical compositions that are similar to the pharmaceutical compositions described above, except that the compounds used are compounds of formulas II, III, IV and V, and pharmaceutically acceptable salts thereof, without any metals bound to them.

In certain embodiments, the labeled ligand is capable of interacting specifically with brain amyloid fibrils. In preferred embodiments, the labeled ligand is capable of interacting specifically with one kind of amyloid fibril, e.g., type-1 fibrils or type-2 fibrils. Most preferably, the labeled ligand is capable of interacting specifically with β-amyloid protofibrils.

The invention also includes a method for determining the localization or quantification of amyloid fibrils in a deceased mammal. A deceased mammal or a portion thereof having amyloid fibrils is provided. An organometallic ligand capable of interacting with the amyloid fibrils is provided. The organometallic ligand is administered to the mammal or portion thereof under conditions which allow the organometallic ligand to interact with the amyloid fibrils so as to result in organometallic ligand-amyloid fibril complexes. The localization or quantification of the complexes in the mammal or portion thereof is determined, e.g., by autoradiography, SPECT, PET or magnetic resonance imaging.

Preferably, the organometallic ligand is a compound of formula I or a pharmaceutically acceptable salt thereof, described above. Preferred compounds of formula I are compounds of formulas 3, 6, 15, 28, 35, 45, 54 or 66, or a pharmaceutically acceptable salt thereof, described above. Other preferred compounds are compounds of formulas II or III or pharmaceutically acceptable salts thereof, described above. Examples of compounds of formula II are 140–143, and examples of compounds of formula III are 144–147, described above. Most preferably, the compounds are the dimers of formula IV or V, or pharmaceutically acceptable salts thereof, described above.

The invention also includes a method for detecting the presence of aggregated prion protein in a mammal. A mammal is provided. Bodily fluid or tissue obtained from the mammal is provided. A labeled ligand capable of interacting with aggregated prion protein is provided. The bodily fluid or tissue is contacted in vitro with the labeled ligand under conditions which allow the ligand to interact with the aggregated prion protein if the aggregated prion protein is present in the bodily fluid or tissue, so as to result in labeled aggregated prion protein. The presence or absence of the labeled aggregated prion protein in the bodily fluid or tissue is determined.

By prion protein is meant the infectious agent of a prion disease. The prion diseases are a group of transmissible neurodegenerative diseases which infect mammals, e.g., cows, sheep, and humans. In humans, the disease, known as Creutzfeldt-Jacob disease, resembles Alzheimer's disease with respect to symptoms and neuropathology. The majority of cases of prion disease are in the livestock population, e.g., in sheep (scrapie) and cows (bovine spongiform encephalopathy, BSE, also known as "mad cow disease"). The human prion disease is extremely rare and usually strikes elderly patients. It has been reported that BSE can be transmitted into humans via infected beef currently, there is no therapeutic agent for the prion diseases. There is a need for a sensitive, simple, and practical method to detect the infectious agent. For example, such a detection method would allow infected livestock, e.g., cows, to be selectively destroyed.

The infectious agent, or prion, is an aggregated form of a normal protein. Although the sequence of the prion protein differs from the amyloid protein of Alzheimer's disease, there is a significant similarity which may account for their similar structure: the prion often exists as an amyloid fibril. The ligands of this invention have affinity for prion.

Bodily fluid is meant to include any fluid from the mammal, e.g., lymph, blood, or urine. Preferably, the bodily fluid used is lymph. In certain preferred embodiments, the bodily fluid is filtered in vitro such that any prion infectious agent that is present in the bodily fluid does not pass through the filter. For example, a Millipore Ultrafree-MC polysulfone membrane, 300,000 NMWL cutoff, can be used. The filter is then contacted with the labeled ligand. Preferably, the presence of resulting labeled prion protein is determined using a SPECT detector, though any other method known to those skilled in the art to detect the labeled prion can also be used.

Preferably, the labeled ligand is a compound of formula I or a pharmaceutically acceptable salt thereof, described above. Preferred labels are the gamma or positron or beta emitters described above, however, any label known to those skilled in the art which is capable of being detected in vitro can be used. Preferably, the labeled ligand of formula I is a compound of formulas 3, 6, 15, 28, 35, 45, 54 or 66, or a pharmaceutically acceptable salt thereof, described above. Other preferred compounds are compounds of formulas II or III or pharmaceutically acceptable salts thereof, described above. Examples of compounds of formula II are 140–143, and examples of compounds of formula III are 144–147, described above. Most preferably, the compounds are the dimers of formula IV or V, or pharmaceutically acceptable salts thereof, described above.

Advantages of using the labeled ligands of this invention include that they are very sensitive, and are much cheaper to make and more chemically stable than antibodies. In addition, antibody tests do not distinguish the infectious form of the protein, the prion, which is usually fibrillar, from the normal, innocuous form of the protein.

The invention also includes another method for detecting the presence of aggregated prion protein in a mammal. A mammal is provided. A labeled ligand capable of interacting with aggregated prion protein is provided. Preferably, the labeled ligand is a compound of formula I or a pharmaceutically acceptable salt thereof, described above. Preferred compounds of formula I are compounds of formulas 3, 6, 15, 28, 35, 45, 54 or 66, or a pharmaceutically acceptable s alt thereof, described above. Other preferred compounds are compounds of formulas II or III or pharmaceutically acceptable salts thereof, described above. Examples of compounds of formula II are 140–143, and examples of compounds of formula III are 144–147, described above. Most preferably, the compounds are the dimers of formula IV or V, or pharmaceutically acceptable salts thereof, described above. The labeled ligand is administered to the mammal under conditions which allow the labeled ligand to interact with the aggregated prion protein if the aggregated prion protein is present in the mammal, so as to result in labeled aggregated prion protein. The presence or absence of labeled aggregated prion protein is determined in the mammal by imaging.

The invention also includes using the labeled ligands to prevent aggregated prion formation in cell culture.

The invention also includes a method for determining the presence of aggregated intracellular β-amyloid. Cells having β-amyloid are provided. A fluorescent ligand capable of interacting with aggregated β-amyloid is provided. The cells are contacted with the fluorescent ligand under conditions which allow the fluorescent ligand to interact with aggregated β-amyloid if it is present so as to result in fluorescent-labeled aggregated β-amyloid. The presence or absence of a fluorescent signal is determined. The presence of a fluorescent signal indicates the presence of aggregated intracellular β-amyloid.

In certain embodiments, the cells are permeabilized prior to contacting the cells with the fluorescent ligand. Preferably, the fluorescent ligand is a compound of formula IX or X, or pharmaceutically acceptable salts thereof. Examples include Congo Red fluorescein ligand 131, Congo Red rhodamine ligand 133 and Congo Red coumarin ligand 135 other fluorescent labels known to those skilled in the art can also be used. The fluorescent ligands are particularly useful as cell culture probes.

The invention also includes a method for identifying an agent useful for treating a mammal for a disease characterized by aggregated intracellular β-amyloid. Cells having β-amyloid are provided. An agent is provided. A fluorescent ligand capable of interacting with β-amyloid fibrils is provided. The cells are contacted with the agent to form a mixture under conditions which allow aggregation of the β-amyloid if the agent was not present. The mixture is contacted with the fluorescent ligand under conditions which allow the fluorescent ligand to interact with β-amyloid fibrils if they are present so as to result in fluorescent- labeled β-amyloid fibrils it is determined if the agent inhibits aggregation of the β-amyloid. The presence of a fluorescent signal indicates the presence of β-amyloid fibrils and therefore minimal or no inhibition by the agent. The absence of a fluorescent signal indicates the absence of β-amyloid fibrils and therefore inhibition by the agent. This inhibition is correlated with the agent being useful for treating a mammal for a disease characterized by aggregated intracellular β-amyloid.

This method can be used for any disease which is characterized by aggregated intracellular β-amyloid, e.g., Down's syndrome or Alzheimer's disease. Preferably, the cells used are neurons which produce intracellular β-amyloid (possibly in aggregated form), e.g., neurons from Down's syndrome patients (Yankner, B., February 1997, Keystone Meeting "Molecular Mechanisms of Alzheimer's Disease), or guinea pig neurons treated with hydrogen peroxide (Younkin, S., February 1997, Keystone Meeting "Molecular Mechanisms of Alzheimer's Disease). Preferably, the fluorescent ligand is a compound of formula X or a pharmaceutically acceptable salt thereof. More preferably, a dimeric fluorescent ligand is used, e.g., a compound of formula IX or a pharmaceutically acceptable salt thereof. Examples of fluorescent compounds include Congo Red fluorescein ligand 131, Congo Red rhodamine ligand 133 and Congo Red coumarin ligand 135. This method identifies agents which can penetrate the cell and reach the site of β-amyloid aggregation, as well as inhibiting the aggregation process itself.

The invention also includes a method for identifying a labeled ligand which selectively binds to one type of β-amyloid fibril. A labeled compound is provided. First β-amyloid fibrils are provided, and second β-amyloid are provided. The labeled compound is contacted with the first β-amyloid fibrils under conditions which allow the labeled ligand to interact with the first β-amyloid fibrils. It is determined if the labeled compound binds to the first β-amyloid fibrils. If the labeled compound does not bind to the first β-amyloid fibrils, then the labeled compound is contacted with the second β-amyloid fibrils under conditions which allow the labeled compound to interact with the second β-amyloid fibrils. It is determined if the labeled compound binds to the second β-amyloid fibrils, binding being correlated with a labeled ligand which selectively binds to the second β-amyloid fibrils as compared to the first β-amyloid fibrils.

The binding of the labeled compound to the β-amyloid fibrils can be determined by standard methods known in the art, e.g., by retention of the labeled compound on a filter which retains the β-amyloid fibrils. Preferably, the labeled compound is a compound of formula I or pharmaceutically acceptable salts thereof, or formula II, III, IV or V. The β-amyloid fibrils can be any β-amyloid fibrils, including, e.g., protofibrils, type-1 fibrils, type-2 fibrils, neuritic plaque or diffuse amyloid. Preferred fibrils are composed of Aβ1-40 or Aβ1-42 proteins. In a preferred embodiment, the second β-amyloid fibrils are protofibrils. Labeled ligands which bind specifically to protofibrils can allow the non-invasive detection of protofibrils, the appearance of which can precede the appearance of neuritic plaque and Alzheimer's disease symptoms by years. Such a protofibril diagnostic is useful for identifying individuals for early therapeutic intervention.

The invention also includes the labeled ligand obtainable from this method.

The invention also includes a method for identifying a labeled ligand which binds to one or more amyloid proteins, e.g., β-amyloid, Islet amyloid polypeptide, Ig light chain, transthyretin, lysozyme, or $β_2$-microglobulin, using, e.g., a labeled compound of formula I, II, III, IV, V, or pharmaceutically acceptable salts thereof. The invention also includes the labeled ligand obtainable from this method.

The following non-limiting examples further illustrate the present invention.

EXAMPLES

Example 1

Synthesis of Bipyridyl-Congo Red (2)

This example illustrates the synthesis of bipyridyl-Congo Red (2), represented by the following formula:

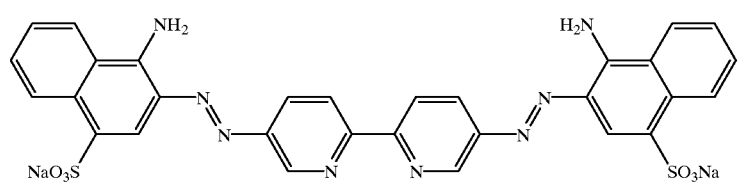

5,5'-diamino-2,2'-bipyridine was prepared from ethyl nicotinate according to the procedures described in Park, T. K. Ph.D. Thesis, Massachusetts Institute of Technology, Cambridge, Mass., pp. 94–98, pp. 170–173 (1992); Knorpp et al., J. Nucl. Med. 1:23–30 (1960); Calogero et al.,.Dyes Pigm. 8:431–447 (1987). To a solution of 5,5'-diamino-2, 2'-bipyridine dihydrochloride (75 mg, 0.30 mmol) in 10% HCl (420 μL) and $H_2O$ (7.5 mL) at −5° C. was added $NaNO_2$ (45 mg, 0.66 mmol) in $H_2O$ (120 μL). After stirring at −5° C. for 5 min, the resulting yellow solution was added to 4-amino-1-naphthalenesulfonic acid sodium salt (183 mg, 0.75 mmol) and sodium acetate trihydrate (324 mg, 2.4 mmol) in $H_2O$ (3 mL) at −5° C. A distinct color change was immediately observed. After stirring at −50° C. for 1 h, $Na_2CO_3$ (900 mg, 9 mmol) was added. Purification by reversed-phase HPLC ($H_2O$/MeOH) afforded 114 mg (58%) of a purple solid.

Analytical HPLC; Delta-Pak C18 reversed-phase column (3.9×300 mm, 15-μm particle size, 300-Å pore size, Waters, Milford, Mass.); 15% MeOH/85% $H_2O$, 3 mL/min, $R_v$=24 mL. $^1$H NMR ($CD_3OD$) δ8.82 (s, 2H), 8.46 (d, J=7.3 Hz,, 2H), 8.40 (s, 2H), 8.16 (d, J =8.0, 2H), 8.03 (d, J=8.0, 2H), 7.83 (d, J=7.3, 2H), 7.21 (m, 4H); MALDI MS using TPKS (Juhasz and Biemann, Proc. Natl. Acad. Sci. U.S.A. 91–4333–4337 (1994)) for $C_{30}H_{22}N_8O_6S_2$ [M], calcd 654.7, found 654.6; UV (10 mM $NaH_2PO_4$, pH 7.4) $λ_{max}$514 (ϵ=2.78×10$^4$cm$^{-1}$ ·M$^{-1}$, 344 (ϵ=2.21×10$^4$).

Example 2

Synthesis of a Technetium Complex with Bipyridal-Congo Red [Tc(CNtBu)$_4$(bpcr)]$^+$ (3)

This example illustrates the synthesis of a technetium complex (3) with bipyridal-Congo Red, represented by the following formula:

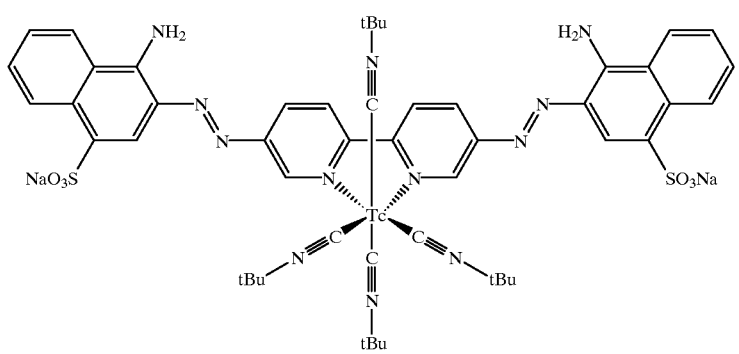

To a 4 mL vial was added 43 mM bipyridyl-Congo Red 2 (250 μL), obtained from Example 1, EtOH (500 μL), and 50 mM NH$_4$[TcO$_4$] (400 μL, New England Nuclear, Boston, Mass.). To this solution tert-butyl isocyanide (5 μL, 44 μmol) and 40 mM Na$_2$S$_2$O$_4$ (1.5 mL in aqueous NaOH at pH 12) were added, and the mixture was stirred and heated in a boiling water bath for 1 h. The vial was then removed from the bath and allowed to cool to room temperature.

Purification by flash chromatography using C18 corasil (37–50 μm, Waters, Milford, Mass.). (H$_2$O/MeOH) followed by reversed-phase HPLC gave 3.3 mg (28%) of a blue solid (specific activity=1.26 MCI/mmol).

Analytical HPLC; 0–5 min 10% MeOH/90% H$_2$O, 5–20 min 10–100% MeOH, 3 mL/min, R$_v$=48 mL. $^1$H NMR (CD$_3$OD) δ9.53 (s, 2H), 8.68 (d, J=8.0, 2H), 8.58 (s, 2H), 8.13 (bs, 4H), 8.09 (d, J=8.0, 2H), 7.47 (t, J=8.2, 2H), 7.35 (t, J=8.2, 2H), 1.70 (s, 18H) 1.38 (s, 18H); MALDI MS (Juhasz and Biemann, Proc. Natl. Acad. Sci. U.S.A. 91:4333–4337 (1994)) for C$_{50}$H$_{58}$N$_{12}$O$_6$S$_2$Tc [M]$^+$, calcd 1085.3, found 1085.8; UV (10 mM NaH$_2$PO$_4$, pH 7.4) λ$_{max}$546 (ε=2.25 ×10$^4$) 332 (ε=2.50×10$^4$).

Thus, the $^{99}$Tc:bipyridyl ligand stoichiometries of the resultant complex were determined to be 1:1 by mass spectrometry, which showed parent ions for the complex, and by $^1$H NMR, which showed two distinct resonances, corresponding to two equatorial and two axial t-butyl isocyanide ligands. (O'Connell et al., Inorg. Chem. 29:3539–3547 (1990)). The anticipated chelation of Tc by the bipyridal group (O'Connell et al., Inorg. Chem. 29:3539–3547 (1990); Adams et al., Inorg. Chem. 22:2798–2800 (1983)) was confirmed by $^1$H NMR, which showed a retention of ligand symmetry and a downfield shift of the protons adjacent to the bipyridyl nitrogens in the complex 3(δ=9.53) relative to the uncomplexed ligand 2 (δ=8.82).

Example 3

Synthesis of Bipyridal-Chrysamine G (5)

This example illustrates the synthesis of bipyridal-Chrysamine G (5), represented by the following formula:

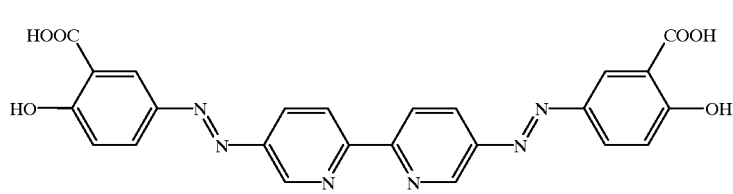

5,5'-diamino-2,2'-bipyridine was prepared from ethyl nicotinate according to the procedures described in Park, T. K. Ph.D. Thesis, Massachusetts Institute of Technology, Cambridge, Mass., pp. 94–98, pp. 170–173 (1992); Knorpp et al., J. Nucl. Med. 1:23–30 (1960); Calogero et al., Dyes Pigm. 8:431–447 (1987). To a solution of 5,5'-diamino-2, 2'-bipyridine (50 mg, 0.27 mmol) in 10% HCl (1.34 mL) was added 2 M NaNO$_2$ (0.27 mL) slowly over 10 min at 0° C. The resulting solution was stirred for 1 h at 0° C. during which the color changed to pale yellow. To this solution at 0° C. was added salicylic acid (111 mg, 0.81 mmol) in 0.5 M Na$_2$CO$_3$ (2.7 mL) which was cooled to 0° C. prior to addition. The pH of the reaction mixture was adjusted to 9 by periodic addition of 0.5 M Na$_2$CO$_3$. After stirring overnight at 4° C., the reaction mixture was warmed to room temperature over 2 h, and acidified to pH 2 with 10% HCl. The precipitate was then filtered, washed with HCl (pH 2) twice, dried, washed with MeOH (2×10 mL), and finally washed with DMF (2×15 mL). The DMF solution was concentrated, filtered through a plug of silica gel with DMF, and dried in vacuo to provide 95 mg (73%) of a brown solid.

$^1$H NMR (DMSO-d$_6$) δ9.16 (d, J=2.2, 2H), 8.62 (d, J=8.5, 2H), 8.34 (d, J=2.7, 2H), 8.26 (dd, J=8.5, 2.2, 2H), 7.87 (dd,

J=8.8, 2.7, 2H), 6.76 (d, J=8.8, 2H); FABMS(+) for $C_{24}H_{15}N_6O_6[M-H]^+$, calcd 483.1, found 483.4; UV (DMF) $\lambda_{max}$468 ($\epsilon$=2.67×10$^4$).

Example 4

Synthesis of a Technetium Complex with Bipyridal-Chrysamine G [Tc(CNtBU)$_4$(bpcg)]$^+$ (6)

This example illustrates the synthesis of a technetium complex (6) with bipyridal-Chrysamine G, represented by the following formula:

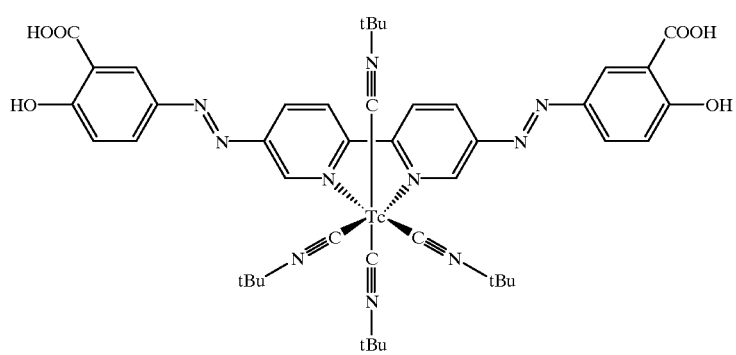

To a 20 mL hydrolysis tube charged with bipyridyl-Chrysamine G 5 (14.4 mg, 0.03 mmol), obtained from Example 3, H$_2$O (1.5 mL), and EtOH (1.5 mL) were added sequentially NH$_4$[TcO$_4$] (0.6 mL of 30 mg/6 mL aqueous solution), tert-butyl isonitrile (15 μL), and Na$_2$S$_2$O$_4$ (30 mg dissolved in 3 mL H$_2$O) at room temperature. The reaction mixture was heated to 100° C. for 1.2 h, cooled to room temperature over 1 h, and MeOH (10 mL) was added. The resulting suspension was filtered, concentrated to 1 mL, and ether (30 mL) was added. The precipitate was filtered, washed with excess ether to remove [Tc(CNtBu)$_6$]$^+$, and washed with MeOH (30 mL). The collected methanolic solution was concentrated, filtered through a plug of silica gel, and dried in vacuo to give 8 mg (29%) of a blue-purple solid (specific activity=0.51 mCi/mmol).

$^1$H NMR (CD$_3$OD) δ9.52 (d, J=2.1, 2H), 8.59–8.55 (m, 4H), 8.37 (dd, J=8.4, 2.1, 2H), 7.99 (dd, J=8.7, 2.4, 2H), 6.94 (d, J=8.7, 2H), 1.64 (s, 18H), 1.28 (s, 18H); MALDI MS (Juhasz and Biemann, Proc. Natl. Acad. Sci. U.S.A. 91:4333–4337 (1994)) for $C_{44}H_{52}N_{10}O_6Tc$ [M]$^+$, calcd 915.4, found 915.9; UV (MeOH) $\lambda_{max}$418 ($\epsilon$=2.39×10$^4$), 272 ($\epsilon$=1.21×10$^4$).

Thus, the $^{99}$Tc:bipyridyl ligand stoichiometries of the resultant complex were determined to be 1:1 by mass spectrometry, which showed parent ions for the complex, and by $^1$H NMR, which showed two distinct resonances, corresponding to two equatorial and two axial t-butyl isocyanide ligands. O'Connell et al., Inorg. Chem. 29:3539:3547 (1990). The anticipated chelation of Tc by the bipyridal group (O'Connell et al., Inorg. Chem. 29:3539–3547 (1990); Abrams et al., Inorg. Chem. 22:2:2798–2800 (1983)) was confirmed by $^1$H NMR, which showed a retention of ligand symmetry and a downfield shift of the protons adjacent to the bipyridyl nitrogens in the complex (δ=9.52) relative to the uncomplexed ligand 5 (δ=9.16).

Example 5

Synthesis of Zinc, Cadmium, Nickel, Coper and Cobalt Complexes with Bipyridyl-Congo Red This example illustrates the synthesis of zinc, cadmium, nickel and copper complexes with bipyridyl-Congo Red.

The stoichiometry of the metal complexes was determined from titrations performed under saturating conditions (the concentration of bipyridyl-Congo Red is much greater than K$_d$) where the stoichiometry of the complex was reflected by the number of equivalents of metal ions needed to reach saturation. Metal titrations were performed in a 1 cm path-length quartz curvet with bipyridyl-Congo Red solutions (~20 μM) in buffer (10 mM NaH$_2$PO$_4$, pH 7.4) at 25° C. Spectra over the wavelength range 190–820 nm were collected after each addition of metal ions (ZnCl$_2$, NiCl$_2$·6H$_2$O, CoCl$_2$·6H$_2$O, CuCl$_2$·2H$_2$O, and CdCl$_2$·2.5H$_2$O) in 1 μM increments followed by equilibration with stirring for at least 30 min. Upon addition of metal ions to bipyridyl-Congo Red (2) the absorptions at 344 and 514 nm decreased in intensity with the concomitant appearance of two new absorptions at ca. 390 and 610 nm. Bipyridyl-Congo Red:metal stoichiometry determined at $\lambda_{max}$; Zn(II) (2:1 ratio, 610 nm), Ni(II) (2:1, 592), Cu(II) (3:1, 568), Cd(II) (2:1, 606), Co(II) (2:1, 608).

Example 6

Binding of Bipyridal-Congo Red Technetium Complexes to β-Amyloid

This example illustrates affinity of the radioactive complexes 3 and 6 for β1-40 amyloid fibrils. Bound and free ligand were separated by centrifugation. In both cases, saturable binding was observed. Saturation experiments for binding of 3 and 6 to β1-40 fibrils (5 μM total protein), as well as Scatchard analyses of the binding data, were performed.

Dissociation constants, IC$_{50}$ and inhibition constants were determined. Aggregated β1-40 peptides (Bachem, Torrance, Calif.; peptide concentrations were determined by amino acid analysis) were prepared by stirring supersaturated solutions of peptide (100 μM) in the standard buffer (10 mM NaH$_2$PO$_4$, pH 7.4) at room temperature for at least 72 h and remained stirring while aliquots were taken. Equilibrium dissociation constants (K$_d$) were measured in standard buffer containing aggregated peptides (5.0 μM total β1-40) and the various concentrations of the labeled ligands. For determination of the IC$_{50}$ value (concentration of inhibitor required to competitively decrease the fraction of the labeled ligand bound to fibrils by 50%), an aggregated peptide solution was added to a constant concentration of the labeled ligand and a varying concentration of inhibitor. The solution was briefly vortexed and allowed to equilibrate at room temperature for 2 h. The solution was centrifuged for 1 min at 14,000 rpm (16,000 g) and the amount of the labeled ligand bound ([B]) to fibrils was obtained by measuring the radioactivity of the pellets or calculated using the equation [B] =[T] - [F] where [F] is the concentration of the labeled ligand in the supernatant (i.e., amount unbound or free) and [T] is the total amount of the labeled ligand added. A Scatchard plot was used to obtain $[B]_{max}$ (apparent maximum amount of the labeled ligand bound to fibrils) and $K_d$. (Freifelder, D., Physical Biochemistry: Applications to Biochemistry and Molecular Biology, 2nd ed.; W. H. Freeman & Co., N. Y. Chapter 10, p. 654 (1982)). The $[B]_{max}$ was based on total protein concentration. Given that not all of the protein is in the fibrous form (solubility of β1-40 is ca. 1 μM, NAC is ca. 11 μM), these values probably represent lower limits; the actual values may be higher. The $IC_{50}$ value was used to calculate the inhibition constant $K_i$. (Cheng et al., Biochem. Pharmacol. 22:3099–3108 (1973)).

The $K_d$'s of 3 and 6 were 630 nM and 160 nM, respectively (see Table 1).

TABLE 1

Dissociation Constants ($K_d$, μM) and Inhibition Constants ($K_i$ μM) for β1-40 fibrils and NAC fibrils at 25° C. and pH 7.4[a]

| amyloid | Congo Red analogs | $K_d$ | $K_i^b$ | $K_i^c$ |
|---|---|---|---|---|
| β1-40 | [Tc(CNtBu)₄(bpcr)]⁺(3) | 0.63(0.06) | | |
| | [Tc(CNtBu)₄(bpcg)]⁺(6) | 0.16(0.05) | | |
| | Congo Red (1) | | 0.46(0.03) | 0.56(0.14) |
| | Bipyridyl-CR (2) | | 0.51(0.11) | 0.48(0.12) |
| | Bipyridyl-CG (5) | | 0.76(0.15) | 0.42(0.10) |
| | Zn (2)₂ | | 1.52(0.23) | |
| NAC | [Tc(CNtBu)₄(bpcr)]⁺(3) | 0.77(0.14) | | |
| | [Tc(CNtBu)₄(bpcg)]⁺(6) | 0.43(0.15) | | |

[a]Data shown are an average of at least three separate experiments and are expressed as mean (±S.D.)
[b]This value was obtained using [Tc(CNtBu)₄(bpcr)]⁺ as the labeled ligand.
[c]This value was obtained using [Tc(CNtBu)₄(bpcg)]⁺ as the labeled ligand.

These values are comparable to the reported $K_d$'s of Chrysamine G to β10-43 fibrils (Klunk et al., Neurobiol. Aging 15:691–698 (1994)) and of Congo Red to insulin amyloid fibrils (Klunk et al., J. Histochem. Cytochem. 37:1273–1281 (1989)).

The relative affinities ($K_i$'s) of the free bipyridyl ligands were determined by displacement of complexes 3 or 6 (see Table 1). Comparable values were obtained for displacement of either complex, suggesting shared binding sites, which may be hydrophobic pockets spaced at regular intervals along the fibril surface. The ordered nature of these sites is suggested by the observed birefringent staining by Congo Red (Cooper, J. H., Lab. Invest. 31:232–238 (1974)), and the fact that the Zn(2)₂ complex, obtained from Example 5, in which the two bipyridyl Congo Red ligands are likely to be orthogonal, does not bind more tightly than the 1:1 Tc complexes (see Table 1). The stoichiometry of saturation, as estimated by Scatchard analysis of the binding curves, differed slightly, with 2.7 moles of 3 and 1.6 moles of 6 bound per mole of β1-40.

Example 7

Binding of Bipyridal-Congo Red Technetium Complexes to NAC

This example illustrates the binding of complexes 3 and 6 to amyloid fibrils comprising the minor brain amyloid peptide NAC. The NAC binding studies were done as described in Example 6 for β1-40, except the NAC concentration used was 15 μM. The binding showed similar features to the binding of β1-40 fibrils (see Table 1). Again, the bipyridal Congo Red complex 3 bound less avidly than the bipyridal Chrysamine G complex 6; dissociation constants of 770 nM and 430 nM, respectively were measured as described in Example 6. Analogous to the case with β1-40 fibrils, the stoichiometry of saturation with 3 (1.4 moles 3 per mole NAC) was slightly higher than for 6 (0.6). The NAC amyloid fibrils and the β1-40 fibrils may share a general feature, suggested by their local sequence homology (Han et al., Chem. Biol. 2:163–169 (1995)), which is recognized by Congo Red, 3 and 6.

Although complex 6 binds to both β1-40 and NAC amyloid fibrils two- to four-fold more avidly than does 3, additional studies demonstrated that the relative affinity of two amyloid probes was not constant for a series of amyloid fibrils comprising different proteins. Thus,, the ligands can show protein-specificity for different amyloids.

Example 8 synthesis of Bisazo Linkers (L=L'=—N=N—)

A. Preparation of Tc-Complex (15) (Prep. Scheme I)

(i) 5,5'-Diethoxicarbonylamino-2',2'-bipyridine(9)

To diacid 7 (1.3 g, 5.32 mmol) in 20 mL of $SOCl_2$ was heated under reflux for 4 hr. The reaction mixture was concentrated in vacuo, suspended in 50 mL of acetone, and treated with 2.1 g of $NaN_3$ in 5 mL of $H_2O$ in portions at 0° C. The mixture was stirred for 30 min, diluted with 100 mL of $H_2O$, filtered, thoroughly washed with $H_2O$, and dried in vacuo. The crude acyl azide 8 suspended in 50 mL of xylene and 50 mL of ethanol was heated under reflux overnight. The reaction mixture was, cooled, and the white precipitate was filtered to give 1.5 g (85%) of dicarbamate 9 as white powder.

(ii) 5,5'-Diethoxycarbonylamino-6,6-difluoro-2'2'-bipyridine (10)

To bipyridine 9 (1.5 g, 4.5 mmol) were added 3 mL of $H_2SO_4$ and 3 mL of fuming $HNO_3$ at 0° C. The mixture was heated at 90° C. for 30 min. The reaction mixture was cooled and poured into crushed ice. The precipitated dinitrodicarbamate 10 was filtered off, washed with $H_2O$ to give 1.3 g (68%) of product.

(iii) 5,5'-Diethoxycarbonylamino-6,6-difluoro-2'2'-bipyridine(11)

A solution of dinitrobipyridine 10 (0.5 g, 1.2 mmol) and 0.1 g of $PtO_2$ in ethanol (20 mL) was stirred under $H_2$ atmosphere for 30 min at room temperature. The reaction mixture was filtered off, concentrated in vacuo and suspended in 1 mL of 48% fluoboric acid. To this solution was added a solution of sodium nitrite (0.18 g, 2.5 mmol) in water dropwise to maintain the reaction temperature around −5° C. After 1 hour, the reaction mixture was filtered off to give 0.17 g (40% yield) of difluoro-bipyridine 11.

(iv) 5,5'-Diamino-6,6'-difluoro-2,2'-bipyridine(12)

A solution of dicarbamate 11 in 1:1 mixture of 2.5 M NaOH and DMSO was stirred overnight at 45° C., according to the procedure described in Andrews et al., J. Chem. SDoc. PT1, 12:2995–3006 (1982). To the reaction mixture was added water, and the precipitated solid was filtered and washed with water to give the diamine 12.

(v) Difluoro-azo dye (13)
Difluorodiamine 12 is tetrazotized by addition of NaNO$_2$. The resulting tetrazo salt is coupled with 2 eq. of salicylic acid to give the difluoro dye 13.

(vi) Dihydrazine-azo dye (14)
Following the procedure described in Ple et al., J. Heterocyclic Chem., 26:475–476 (1989), difluoride 13 in ethanol is treated with 2 eq. of hydrazine hydrate in ethanol at 0° C. After 1 hour, the dihydrazine dye 14 is isolated by filtration and purified by column chromatography.

(vii) Tc-Complex (15)
A mixture of the dye 14, 2 eq. HCl, NH$_4$TcO$_4$, and Na$_2$S$_2$O$_4$ in EtOH is heated under reflux for 6 to 12 hours, and cooled to room temperature. The precipitated solid is removed, dissolved in EtOH, treated with 1 eq. triphenyl phosphine, and the resulting Tc$^+$ is further reduced to Tc$^0$ either electrochemically or with metal hydrides. The same complex 15 can be made from a photochemical reaction of the dye ligand 14 with hexakistbutylisonitrile-Tc complex.

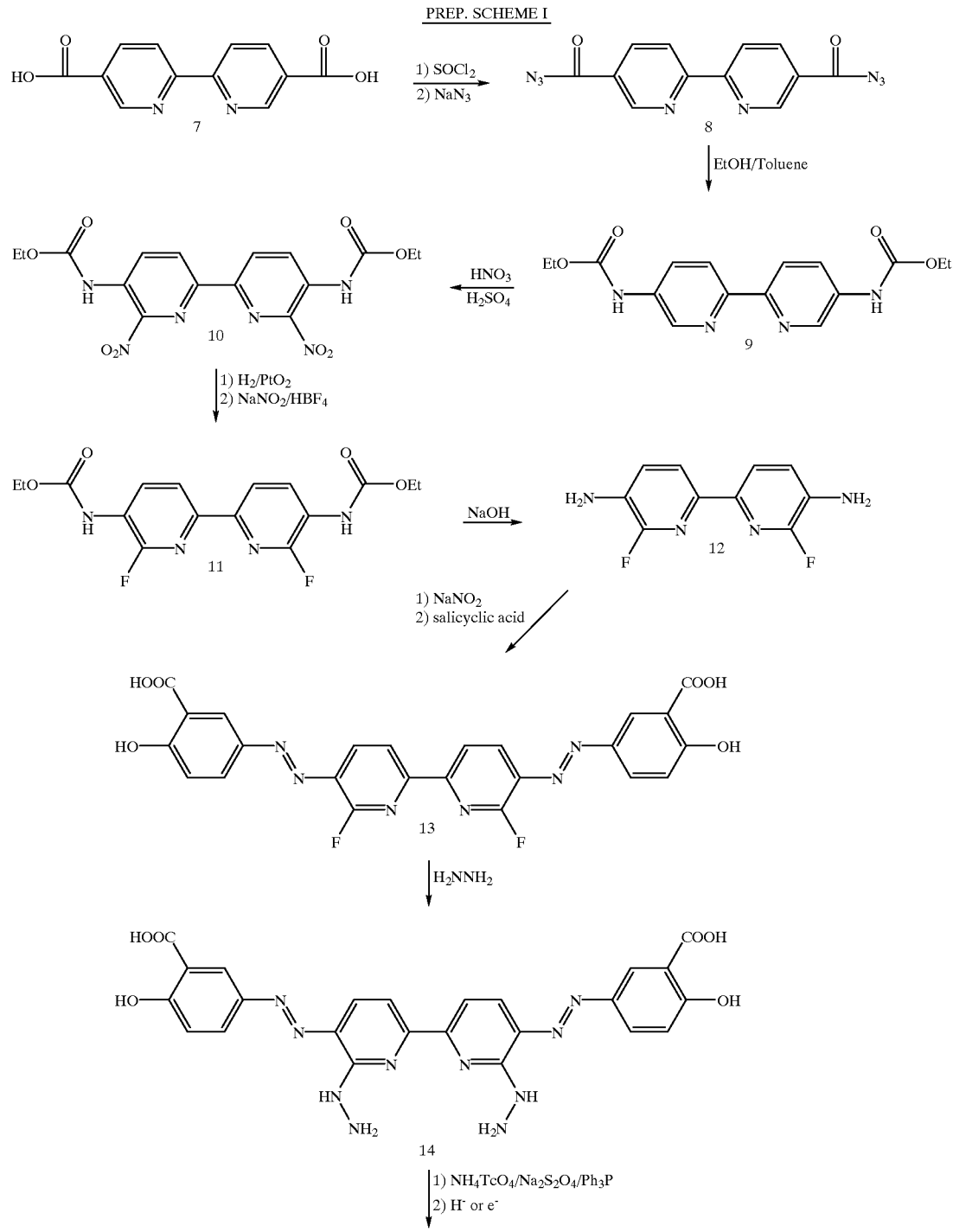

PREP. SCHEME I

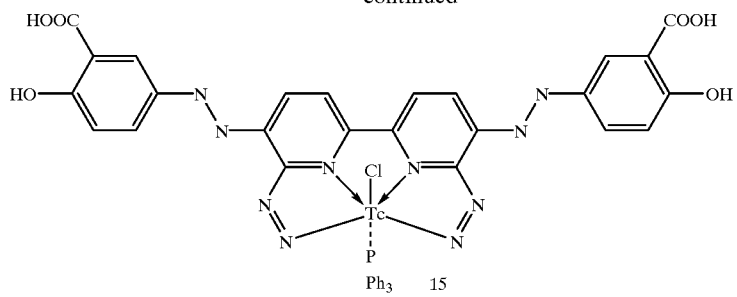

B. Alternative Preparation of Tc-Complex (15) (Prep. Scheme II)

Dinitro-diamine 16, prepared from 10 via hydrolysis, is tetrazotized and coupled with salicylic acid. The resulting dinitro azo dye 17 is reduced to diamine with $H_2/PtO_2$ in ethanol or preferentially with NaSH according to the procedure described in Ueno, J. Amer. Chem. Soc. 74:4508–4511 (1952). The diamine 18 is then tetrazotized and reduced with $SnCl_2$ or Zn to dihydrazine 14 (Hass et al., J. Org. Chem. 15:8–14 (1950)). When the reduction of diazonium group to hydrazine is problematic, direct substitution of hydrazine provides the same product 14, which is transformed to the complex 15 under the same protocol as described above.

PREP SCHEME II

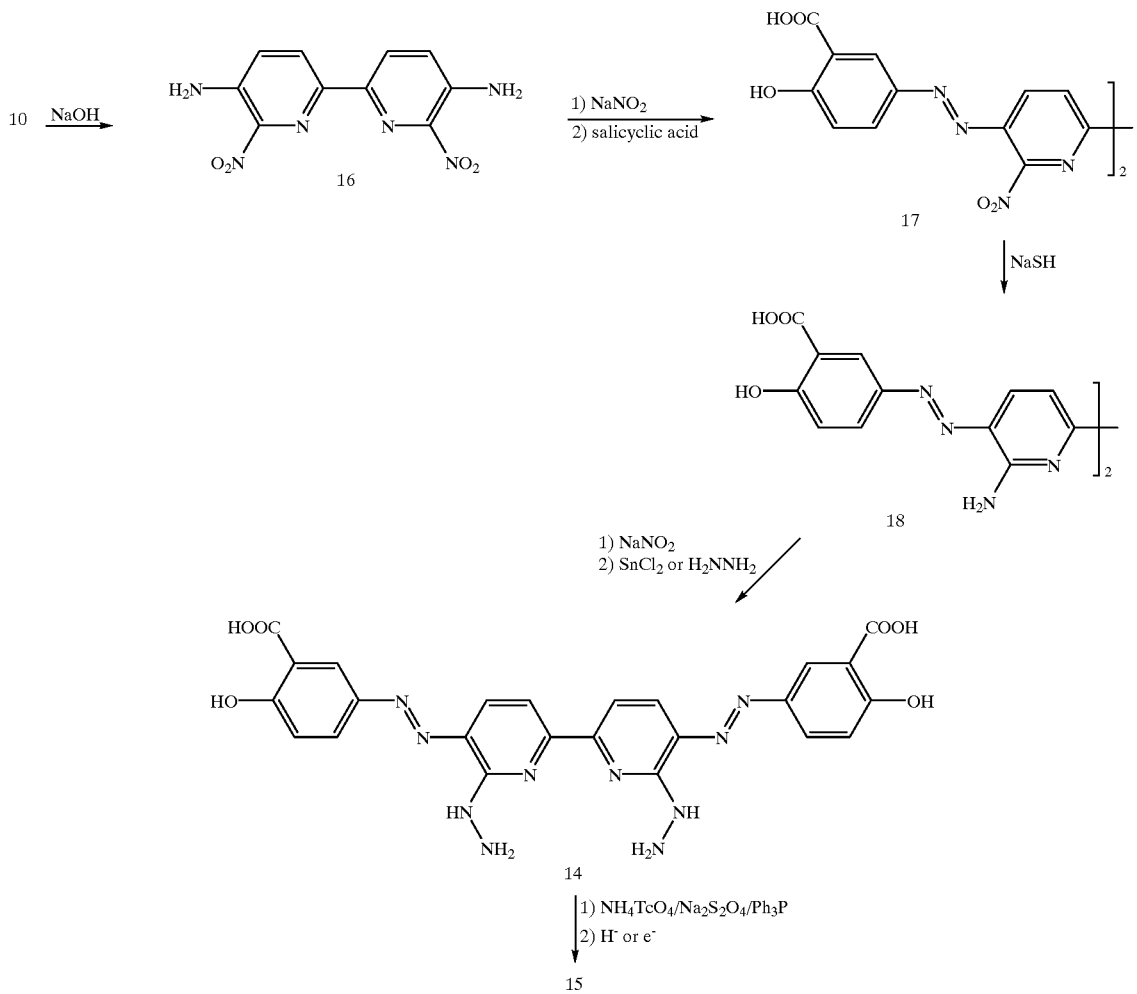

C. Alternative Preparation of Tc-Complex 15 (Prep. Scheme III)

The diamide 9 was hydrolyzed to the diamine 19 according to Andrews et al., J. Chem. Soc. PT1, 12:2995–3006 (1982). To 0.5 g of diamine 19 was added 2.5 mL of 35% HCl, and the solution was heated at 80° C. To this solution was added 0.4 mL of 38% $H_2O_2$, and the resulting solution was stirred for 5 hours at 80° C. The reaction mixture was cooled to room temperature, and basified with 2.5 M NaOH. The brown solids precipitated was filtered off and dried in vacuo. A mixture of crude 20 and hydrazine in DMSO is heated overnight to give the diaminodihydrazine 21. The dihydrazine 21 is treated with 2 eq. $Ac_2O$ to the protected hydrazine 22, which is then tetrazotized, coupled with salicylic acid, and deprotected to afford the dye 23. The dye 23 is transformed to the complex 15 using the same protocol.

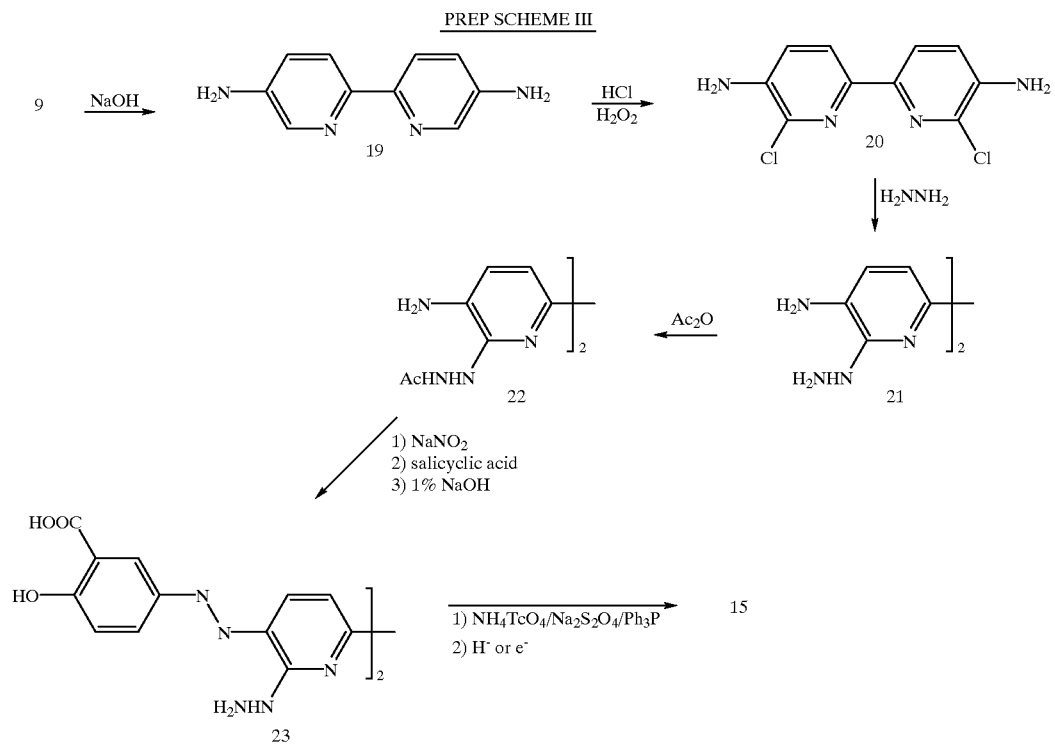

PREP SCHEME III

Example 9

Synthesis of Bisamide Linkers (L=L'=—CONH—)

Preparation of Complex 28 (Prep. Scheme IV)

Diamino-dinitro-bipyridine 16 is coupled with 4-hydroxyisophthalic acid (24) using DCC/DMAP or other coupling conditions (Klausner et al., Synthesis, 549–559 (1974)), to provide diamide 25. The dinitrodiamide 25 is reduced with $H_2/PtO_2$ to diamine 26 as described above. The diamine 26 is tetrazotized and treated with hydrazine or reduced with stannous chloride to the diamide ligand 27. The bis-amide dye 27 is transformed to the Tc-complex 28 using the same protocol as for 15.

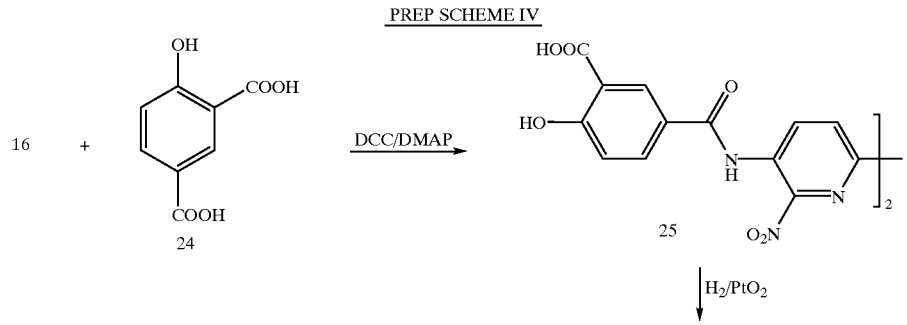

PREP SCHEME IV

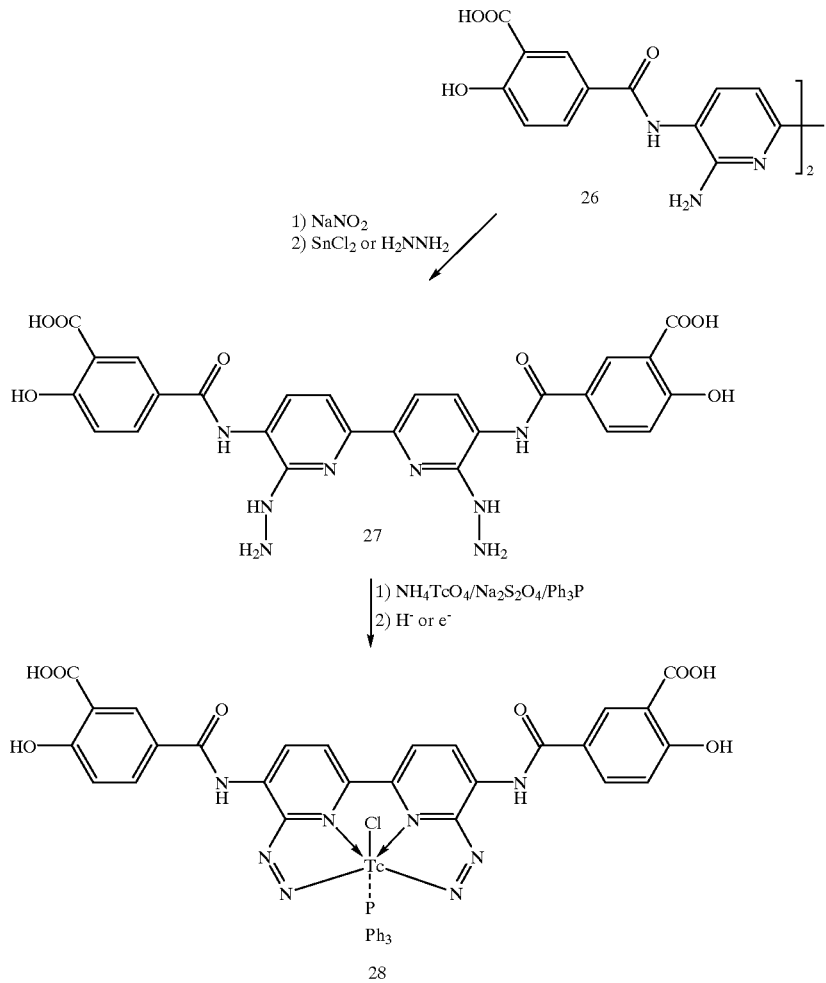

Example 10

Synthesis of Bisamide Linkers (L=L'=—NHCO—)

Preparation of Bisamide 35 (Prep. scheme V)

Diethyl-bipyridine-dicarboxylic acid 29 is nitrated with $H_2SO_4$/fuming $HNO_3$ to provide the dinitro ester 30. The ester 30 is saponified with KOH/EtOH to the diacid 31, which is then coupled with 4-aminosalicylic acid (32) under DCC/DMAP condition to give diamide 33. The nitro groups in 33 are reduced to amines by catalytic hydrogenation, and the resulting diamine is tetrazotized, reduced with stannous chloride or treated with hydrazine to afford the bisamide ligand 34. The bis-amide dye 34 is transformed to the Tc-complex 35 using the same protocol as for 15.

PREP SCHEME V

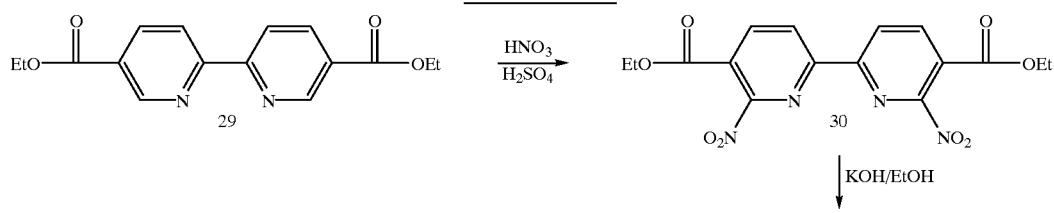

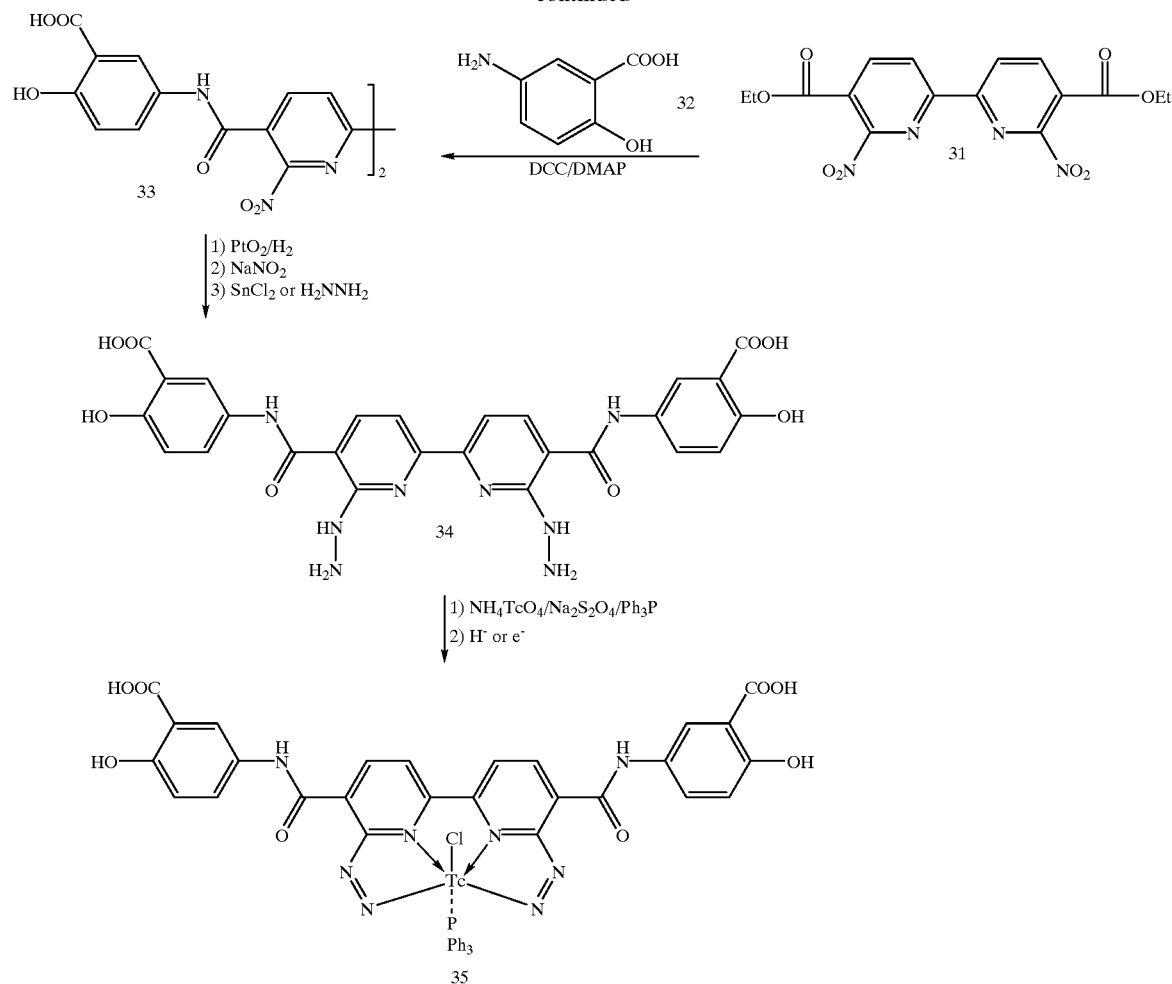
Example 11
Synthesis of Bishydrazine Linker (L=L'=—HN—NH—)
Preparation of Complex 37 (Prep. Scheme VI)
Bisazodiaminobipyridine 17 is tetrazotized with $NaNO_2$ and reduced with 4 eq. of $SnCl_2$ or Zn/HCl to the corresponding bishydrazinodihydrazine ligand 36. The bishydreizide 36 is transformed to the Tc-complex 37 using the same protocol as for 15.
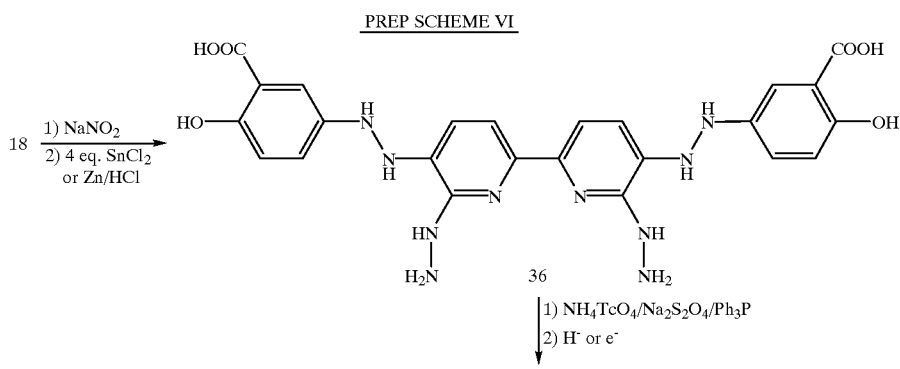
PREP SCHEME VI

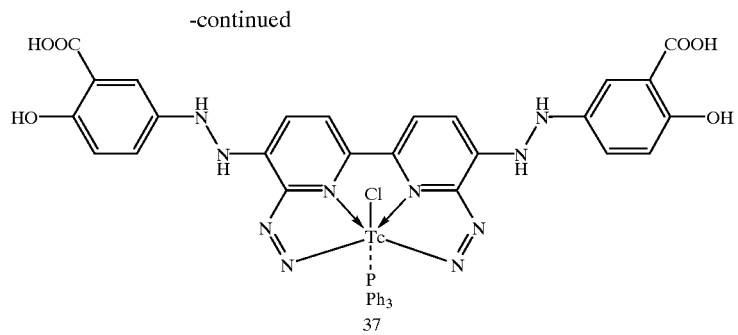

Example 12

Synthesis of Bisalkene Linker (L—L'=—C=C—, TRANS)

Preparation of Bisalkene 45 (Prep. Scheme VII)

The diester 30 is reduced to the diol 38 with DIBAL (dusobutylaluminum hydride). The diol groups in 38 are subsequently treated with first a mixture of NCS (N-chloro succinimide) and DMS (dimethyl sulfide), second with potassium diphenylphosphide, and finally with hydrogen peroxide to afford the phosphine oxide 39 (Posner et al., J. Org. Chem., 60:4617–4628 (1995)). The phosphine oxide 39 is deprotonated with phenyl lithium, and coupled with the aldehyde 40 (Lythgoe et al., J. Chem. Soc. PT1, 6:590–595 (1978)), prepared from 4-hydroxy-3-methyl benzaldehyde after hydroxylation with $SeO_2$ and followed by protection with TBDMS (t-butyldimethylsilyl) groups. The bis-alkene 41 is treated with TBAF (tetrabutylammonixim fluoride) to unmask the alcohol groups. The benzylic alcohol in 41 is oxidized with $MnO_2$ to the corresponding carboxylic acids (Ahrens et al., J. Heterocyclic Chem., 4:625–626 (1967)). Platinum oxide catalyzed reduction of dinitro groups in 42 provides the diamine 43 which is then tetrazotized with sodium nitrite and reduced with stannous chloride or treated with hydrazine to give the bis-alkene ligand 44. The bis-alkene 44 is transformed to the Tc-complex 45 using the same protocol as for 15.

PREP SCHEME VII

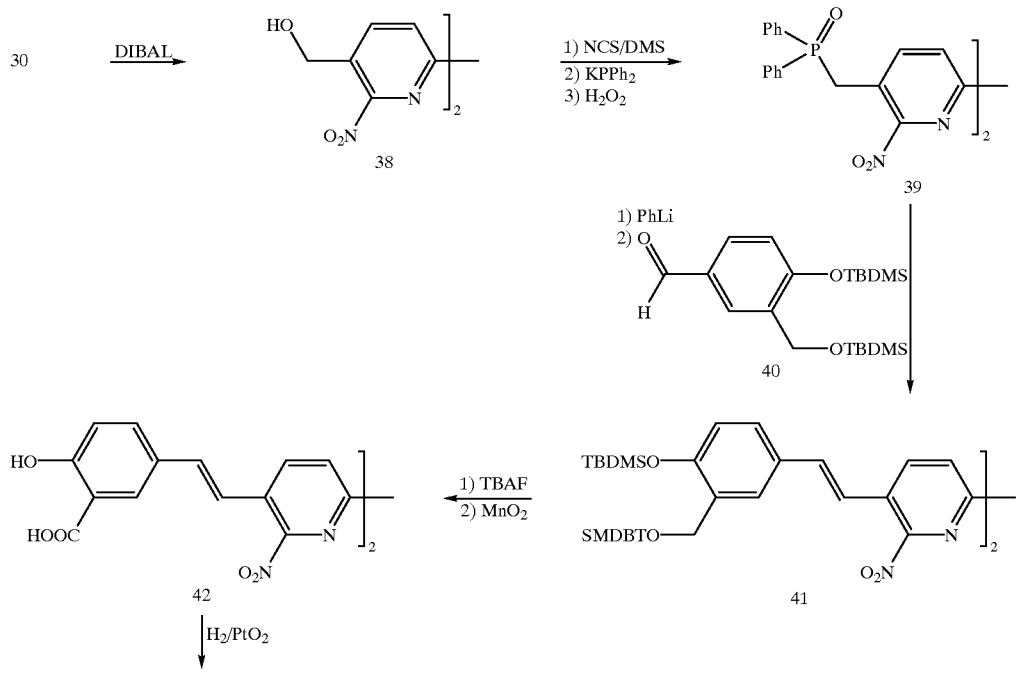

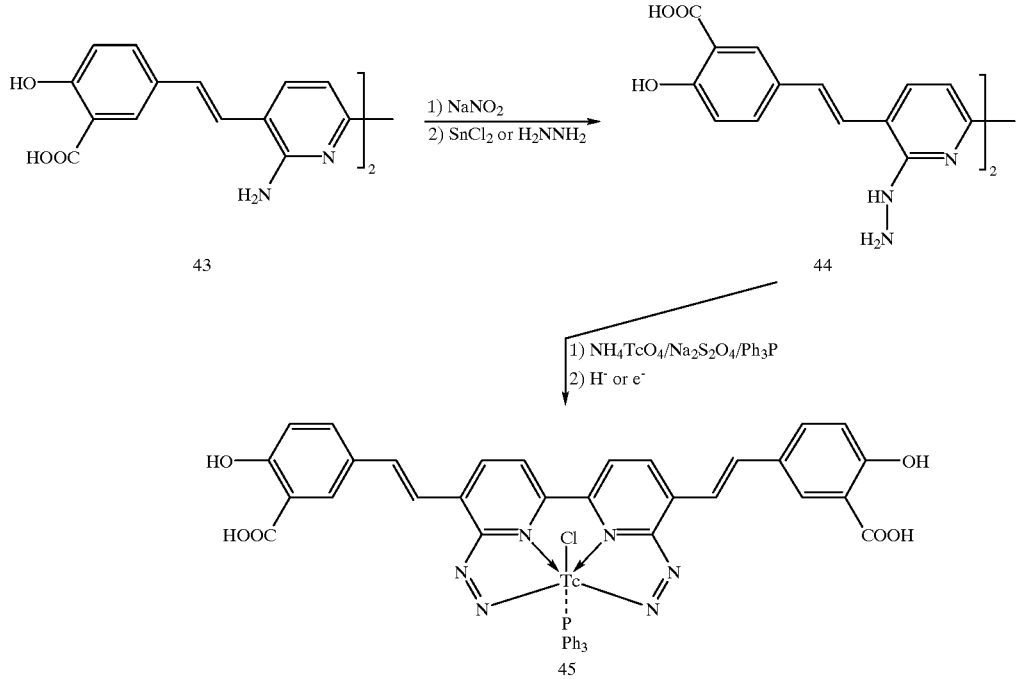

Example 13

Synthesis of R=R'=—CH$_2$OH, —CH$_2$NH$_2$, —CH$_2$SH, —o—C$_6$H$_4$—CH$_2$—COOH A. Preparation of Complexes 52, 53, and 54 (Prep. Scheme VIII)

(i) Tc-Complex 52

To the diamine 20 in 5% NaOH is added 2 eq. of Boc$_2$O at room temperature to give the dicarbamate 46. The dicarbamate 46 is treated with 4 eq. of nBuLi at −20° C., and quenched with DMF at −20° C. After 2 hours at room temperature, the bis-alcohol 47 in the reaction mixture is treated with 2 eq. of benzoyl chloride to give the bis-benzylester 48. The diamine 48 is treated with NaNO$_2$, and coupled with salicylic acid to af ford the hydroxy dye 49. A mixture of the dye 49, ammonium pertechnetate, dimercaptoethane, and sodium dithionate in EtOH is heated under reflux to give the Tc complex 52.

(ii) Tc-Complex 53

The bis-alcohol 49 is transformed to the bis-amine 50 via successive treatments with p-toluenesulfonyl chloride, lithium bis(trimethylsilyl)amide, and finally with hydrochloric acid (Mukaiyama et al., Tetrahedron Lett. 39:3411–3414 (1970). The dye 50 is similarly transformed to the complex 53 using the same protocol as for 52.

(iii) Tc-Complex 54

The bis-alcohol 49 is treated with thiolacetic acid and ZnI$_2$ (Gauthier et al., Tetrahedron Lett. 27:15–18 (1986)), to give the bis-thiol 51 after unmasking step. The dye 51 is similarly transformed to the complex 54 using the same protocol as for 52.

PREP SCHEME VIII

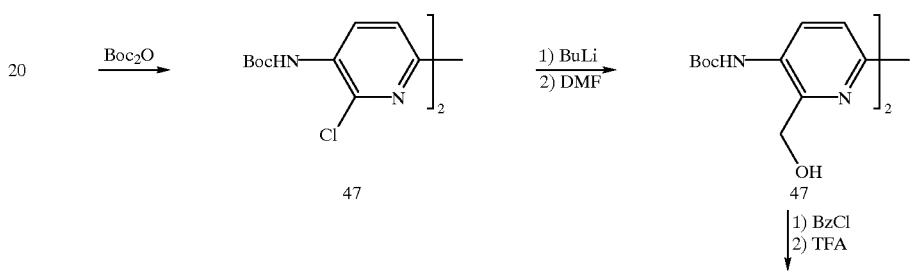

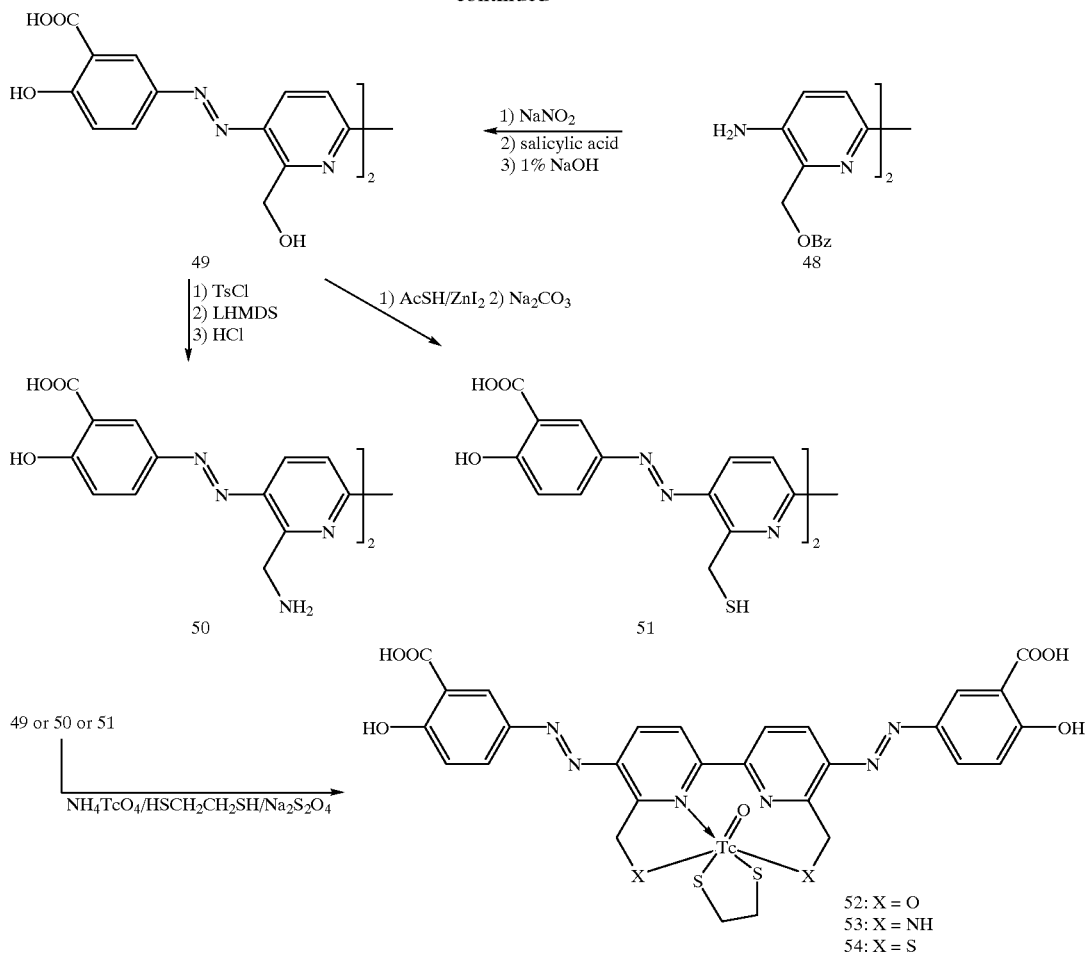

B. Preparation of Tc-Complex 60 (Prep. Scheme IX)

The dichloride 46 is reacted with the tin compound 55, prepared according to the procedure described in Bates et al., Tetrahedron Lett., 37:267–270 (1996), in the presence of tetrakis-(triphenylphosphine)-palladium to give the adduct 56. The bis-carbamate 56 is treated with trifluoroacetic acid (TFA) to afford the diamine 57, which is tetrazo coupled with salicylic acid to give the dye 58. The nitrile groups in the dye 58 are hydrolyzed to the dicarboxylic acid 59, which is then transformed to the complex 60 using the same protocol as for 52.

PREP SCHEME IX

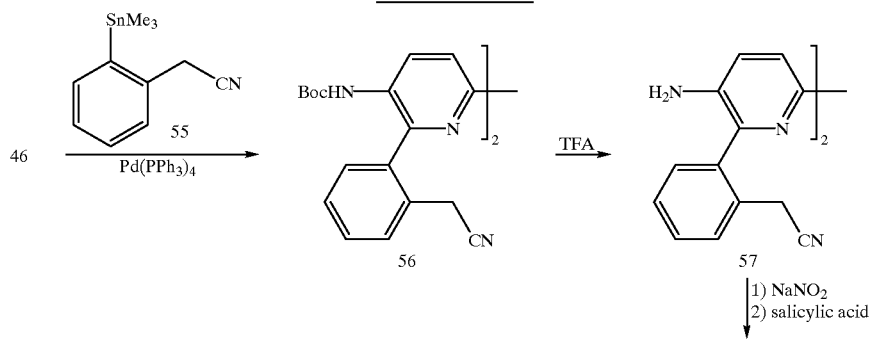

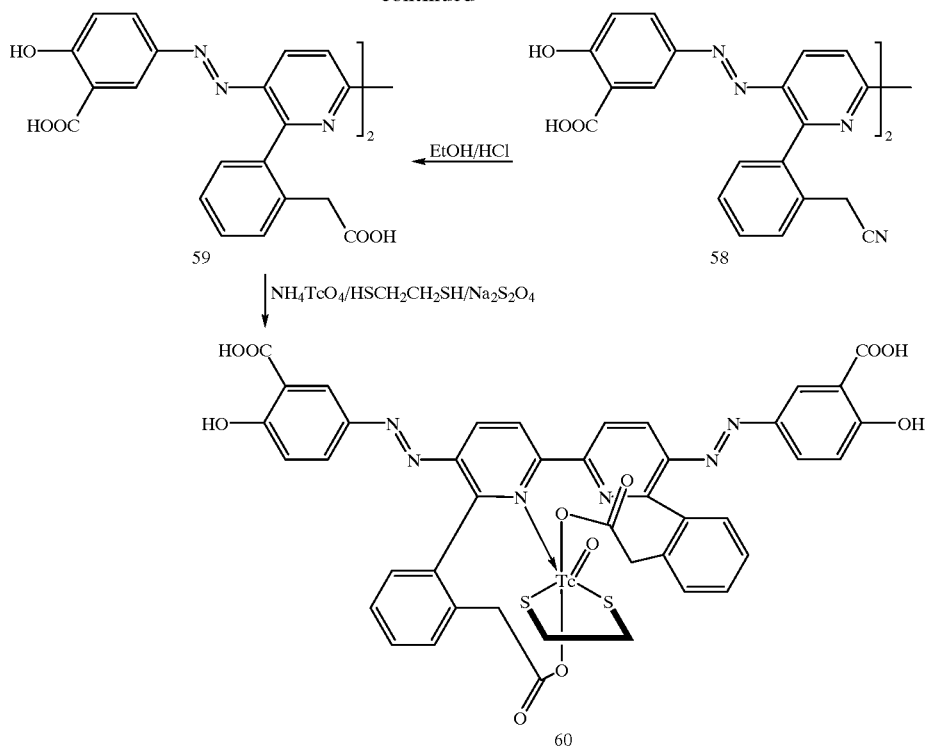

Example 14

Synthesis of R=—CH$_2$NHCH$_2$CH$_2$SH,
R'=—CH$_2$SH

Preparation of the Tc-Complex 68 (Prep. Scheme X)

The bis-alcohol 47 is brominated on the benzylic positions with CBr$_4$/PPh$_3$ system to the bis-bromide 61. Boc groups in 61 are removed with TFA to the corresponding bis amine, tetrazotized, coupled with salicylic acid to the dye 62. The displacement of one bromide group in the dye 62 is proceeded by using 0.5 eq. of the amine 63, prepared according to Hiskey et al., J. Org. Chem. 31:2178–2183 (1966). The other bromide group in 64 is then displaced with potassium thiolacetalte, treated with TFA to the dithiol 65. The dye 65 is suspended in EtOH and mixed with ammonium pertechnetate and sodium dithionate, and the resulting solution is heated under reflux to give the Tc-oxo complex 66 (Madras et al., Synapse 22:239–246 (1996)).

PREP SCHEME X

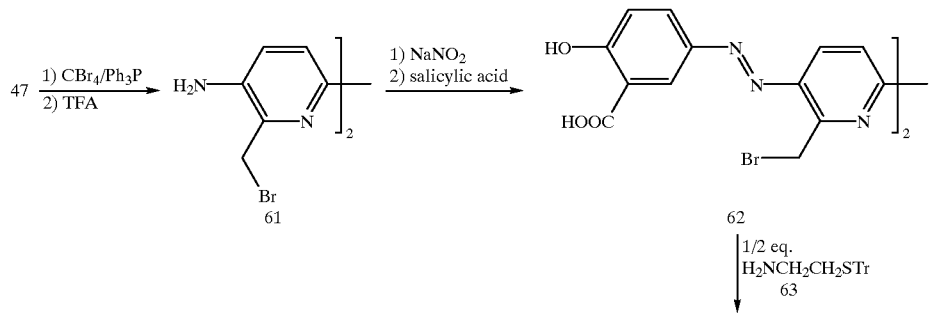

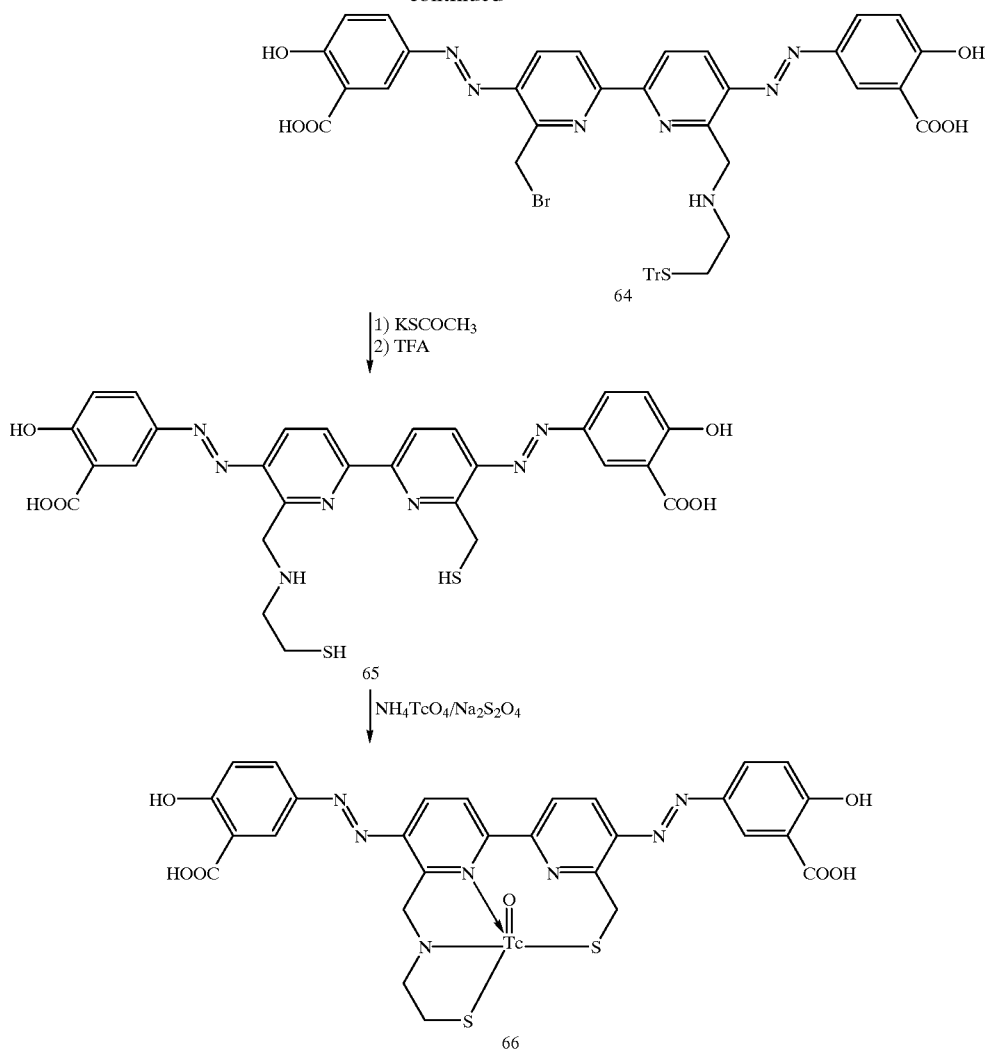

Example 15

Imaging with Organometallic Ligands Which Can Cross the Blood Brain Barrier Alone This example illustrates administration and imaging using an organometallic ligand which can cross the blood brain barrier by itself. The procedure used is adapted from Madras et al., Synapse 22:239–246 (1996). The organometallic ligand, e.g., 54 or 66 (ca. 15–75 mCi per 65 kg body weight) is administered to a patient intravenously via catheter as a saline solution. Images are acquired after 2 hours using a digital ASPECT system (Digital Scintigraphics, Inc., Boston, Mass.) or a comparable instrument (see, e.g., Neuwalt, Implication of the Blood Brain Barrier and Its Manipulation, Vol. II, Plenum Press, N.Y. (1989) p. 210). The procedure for reconstruction is described in Holman et al., J. Nucl. Med., 31:1206–1210 (1994).

Example 16

Imaging with Organometallic Ligands Plus a Blood Brain Barrier Opener

This example illustrates administration and imaging using an organometallic ligand plus alternative blood brain barrier openers.

Method 1: Osmotic Blood Brain Barrier Modification with Mannitol

The procedure used is adapted from Neuwalt, Implication of the Blood Brain Barrier and Its Manipulation, vol. II, Plenum Press, N.Y. (1989), pp. 207–213. The blood brain barrier is reversibly disrupted by administration of an arterial bolus of a hypertonic mannitol solution. This procedure has been used extensively to deliver drugs and imaging agents to the brain. A 10-step procedure is given in Neuwalt, vol. II, p. 213 (steps 5, 10–13 are specific to brain tumor patients).

After anesthetizing the patient, a hypertonic mannitol solution (180–300 ml over 30 sec.) is injected arterially, for example, via the vertebral artery or cartoid artery (see Neuwalt, p. 213). After about 5 minutes to about 3 hours, 15–30 mCi of the organometallic ligand, e.g., 3 or 6, is administered intravenously. Imaging is done as described in Neuwalt, p. 210. The radioactivity is quantified and localized. Patients in the early stages of Alzheimer's disease localize a significantly increased amount of radioactive ligand relative to age-matched controls. Late-stage Alzheimer's disease patients localize an even greater amount of radioactivity.

Method 2: Opening of the Blood Brain Barrier with Organic Solvents

Dimethyl sulfoxide (DMSO) is used to reversibly and innocuously open the blood brain barrier. The procedure used is adapted from Neuwalt, Implication of the Blood Brain Barrier and Its Manipulation, vol. I, Plenum Press, N.Y. (1989) pp. 336–337, and is modified, replacing the antitumor compound with 15–75 mCi of the organometallic ligand, e.g., 3 or 6.

Method 3: Opening of the Blood Brain Barrier with Drugs

Two classes of drugs have been shown to reversibly open the blood brain barrier. See Neuwalt, Implication of the Blood Brain Barrier and Its Manipulation, vol. I, Plenum Press, N.Y. (1989) pp. 332–334 and 337. Metrazol, a CNS stimulant, reversibly opens the barrier. This drug is coadministered with an anti-seizure drug, in order to suppress seizures which can result from the effective dose. In addition, certain anticancer drugs open the blood brain barrier for a relatively long period of time. These compounds, however, are toxic, and thus can cause additional problems. 15–30 mCi of the organometallic ligand, e.g., 3 or 6, is injected into the patient subsequent to administration of the drug.

Method 4: Opening of the Blood Brain Barrier with RMP-7

Polypeptides called receptor mediated permeabilizers (RMP) have been shown to increase the permeability of the blood brain barrier to various agents. See U.S. Pat. No. 5,268,164. RMP-7 is used according to the procedure described in U.S. Pat. No. 5,268,164 (column 14), so as to open the blood brain barrier and allow the organometallic ligand, e.g., 3 or 6, to pass through.

Example 17

Organometallic Ligands as Therapeutics

This example illustrates treatment of Alzheimer's disease with an organometallic ligand so as to inhibit aggregation of amyloid proteins in the brain. The organometallic ligand, e.g., Zn complex analogous to 3, at a dose of 10 mg/kg/day, is administered intravenously to a patient having Alzheimer's disease. A blood brain barrier opener is coadministered or preadministered (see Example 16), if necessary, to allow crossing of the blood brain barrier by the organometallic ligand. This procedure is followed daily for 100 days. Amyloid formation is imaged by the method described above. As a result of such treatment, aggregated amyloid formation is reduced.

Example 18

Detection of Scrapie Prion in Hamster Brain Tissue

This example illustrates a method for detecting the presence of scrapie prion in hamster brain tissue using an organometallic ligand. Hamster brain tissue (0.2 g) from normal and scrapie hamsters (obtainable from NIAID, Rocky Mountain Laboratory, Hamilton, Mt.) is homogenized in water (2 mL). An aliquot of the homogenate (5 μL) is removed and diluted into 100 μL with a 4% methanol-water solution of the $^{99}$Tc-Congo Red complex (15 μM), e.g., 3 or 6. The mixture is incubated for 30 min. at 25° C., and then spun for 30 min. at 234,000 × g at 20° C. The supernatant (95 μL) is separated from the pellet (5 μL) by pipetting. The two fractions are separately analyzed by scintillation counting, and the ratio of pellet cpm/supernatant cpm is determined. PrP$^{sc}$ (hamster) in scrapie hamster brain is detected above background.

Example 19

Detection of Bovine Spongiform Encephalopathy Prion (PrP$^{sc}$) in Bovine Tissue This example illustrates a method for detecting the presence of BSE prion in bovine brain or lymph tissue using an organometallic ligand. Bovine brain (est. 3–300 pg PrP$^{sc}$/g diseased brain), or lymph tissue (ca. 10 mg), is homogenized in water (100 μL). An aliquot of this homogenate (5 μL) is removed and diluted to 100 μL with a 4% methanol-water solution and the mixture is incubated for 30 min. at 25° C., then spun for 30 min. at 234,000 × g at 20° C. The supernatant (95 μL) is removed by pipetting and the pellet is resuspended in 95 μL of a 10% w/v solution of N-lauryl sarcosinate to solubilize membrane-associated proteins and the centrifugation procedure is repeated. The pellet from the second centrifugation is diluted into 95 μL of 4% methanol-water containing ca. 150 nM $^{99m}$Tc-Congo Red (3). The sample is sedimented as above and the pellet and supernatant are analyzed by a γ-camera. The ratio of cpm pellet/cpm supernatant is quantified; a high ratio indicates the presence of PrP$^{sc}$. The amount of PrP$^{sc}$ in the pellet is determined by comparison of the pellet cpm to a standard curve, determined using purified PrP$^{sc}$.

Example 20

Preparation of NX$_3$ Complex 120 (Prep. Scheme XI)

(i) 5-Bromo-2-N-Boc -Amino-Benzyl Alcohol 111

To a flask charged with 2.15 g (10 mmol) of 5-bromo, 2-amino-benzoic acid 109 was added 60 mL of THF and 1.7 g of NaH (60% in mineral oil) at room temperature. The mixture was heated under reflux for 1 hr, cooled to room temperature. To the mixture was added 2.04 g (1.2 eq) of di t-butyl dicarbonate and the resulting mixture was refluxed for 30 min, cooled to room temperature, and 0.8 g of NaH was added into the mixture. The reaction mixture was refluxed for 16 hr under Ar atmosphere. The mixture was then quenched with water carefully, acidified to pH 3, extracted with methylene chloride, concentrated to give the crude acid 110 (used for the next reaction without further purification). To a solution of 110 in 50 mL of THF was added N-methylmorpholine (1.0 g) and chloroethylformate (1.1 g) at −10° C. After 10 min, NaBH$_4$ (1.1 g) was added all at once, followed by careful addition of 100 mL of anhydrous MeOH with ice cooling. After 1 h, the reaction mixture was concentrated and partitioned into water and ethyl acetate. The separated organic layer was dried over MgSO$_4$, concentrated, and chromatograptied to give the alcohol 111 (1.4 g, 47% from 109) as a colorless solid. $^1$H NMR (300 MHz, CDCl$_3$) δ7.81 (d, 1H, J=8.7 Hz), 7.65 (bs, 1H), 7.38 (dd, 1H, J$_1$=8.7, J$_2$=2.4), 7.27 (d, 1H, J=2.4), 4.62 (d, 2H, J=5.9), 1.50 (s, 9H).

(ii) 5-Bromo-2-N-Boc-Amino-Acetyl Benzoate 112

To a solution of the alcohol 111 (1.24 g, 4.13 mmol) in 20 mL of anhydrous methylene chloride, 1 mL of acetic anhydride, 1 mL of acetyl chloride and 1 mL of pyridine was added 4-N,N-dimethylaminopyridine (10 mg) at room temperature. After 1 hr, the reaction mixture was partitioned into methylene chloride and water. The separated organic layer was dried over MgSO$_4$, concentrated and chromatographed to give 112 as a white solid (1.40 g, 4.08 mmol, 99% yield). $^1$H NMR (300 MHz, CDCl$_3$) δ7.78–7.76 (m, 1H), 7.45–7.42 (m, 2H), 5.03 (s, 2H), 2.10 (s, 3H), 1.52 (s, 9H).

(iii) 5-Bromo-2-N-Boc-Amino-Benzaldehyde 114

To a flask charged with the alcohol 111 (6.6 mmol) in 10 mL of methylene chloride was added 0.12 mL of DMSO, oxalyl chloride (0.07 mL) and 0.5 mL of triethylamine at −78° C. After 3 hr, the reaction mixture was diluted with ether and washed with aqueous NaHCO$_3$, water, and brine. The organic phase was dried over MgSO$_4$, concentrated and the crude product was purified by silica gel chromatography (solvent system) to afford aldehyde 114 as a white solid (0.17 g, 5.69 mmol, 86% yield). $^1$H NMR (300 MHz, CDCl$_3$) δ10.29 (bs, 1H), 9.82 (s, 1H), 8.93 (d, J=9.0 Hz), 7.71 (d, 1H, J=2.3), 7.63 (dd, 1H, J$_1$=9.0, J$_2$=2.3), 1.52 (s,9H).

(iv) Stannylated Benzoate 113

A mixture of 1.33 g (3.88 mmol) of the bromide 112, 0.24 g (0.2 mmol) of tetrakis (triphenylphosphine) palladium, 2.58 g of bistributyltin in 40 mL of triethylamine was refluxed under Ar for 12 hr. After cooling, the reaction mixture was decanted and chromatographed (95/5 hexane/ethyl acetate) to give the stannyl benzoate 113 as a colorless oil (1.03 g, 1.86 mmol, 48% yield). $^1$H NMR (300 MHz, CDCl$_3$)

(v) Biphenyl Adduct 115

A mixture of the 0.17 g (0.57 mmol) of the Promo benzaldehyde 114, 0.13 g (0.1 mmol) of tetrakis triphenylphosphine palladium in 10 mL of anhydrous toluene was refluxed under argon for 2 hours. A solution of the stannyl benzoate 113 in 5 mL of anhydrous toluene was added dropwise through the syringe over 1 hr while keeping the reaction mixture under reflux. After 12 h, the reaction mixture was concentrated and the crude product was purified by silica gel chromatography to give 0.11 g of the product 115 (0.11 g, <43% yield) contaminated with trace of tributyltin compounds. $^1$H NMR (300 MHz, CDCl$_3$) δ10.09 (bs, 1H), 9.98 (s, 1H), 8.52 (d, 1H, J=8.3), 7.96 (d, 1H, J=8.3), 7.78–7.76 (m, 2H), 7.55–7.53 (m, 2H), 5.17 (s, 2H), 2.12 (s, 3H), 1.55 (s, 9H).

(vi) Biphenyl Methoxybenzyl Sulfide 116

A solution of 80 mg of the biphenyl adduct 115 in 3 mL of THF and 1 mL of water was treated with excess LiOH at 0° C. After 6 hr, the reaction mixture was neutralized with aq. HCl, extracted with methylene chloride (30 mL×2), dried over MgSO$_4$, and concentrated. The crude product was purified by silica gel chromatography to provide the biphenyl alcohol (0.06 g). To a solution of the alcohol in 5 mL of THF was added 50 mg of carbon tetrabromide and 40 mg of triphenylphosphine at room temperature. After 2 hr, the reaction mixture was treated with the THF solution of the sodium thiolate prepared from 46 mg of 4-methoxy benzyl mercaptan and 200 mg of sodium hydride (60% in mineral oil) at room temperature. After 2 hr, the reaction mixture was partitioned into ethyl acetate and water. The separated organic layer was dried over MgSO$_4$, concentrated and purified by silica gel chromatography to afford the thioaldehyde 116 (55 mg, 70% overall yield from 115).

(vii) Biphenyl Bromide 117

A solution of 55 mg (0.095 mmol) of the aldehyde 116 in 5 mL of anhydrous MeOH was treated with 20 mg of NaBH$_4$ at room temperature. After 1 hr, the reaction mixture was quenched with 5 mL of water, extracted with ethyl acetate, dried over MgSO$_4$, concentrated, dissolved in 5 mL of THF and treated with carbon tetrabromide and triphenyl phosphine at room temperature. After 1 hr, the reaction mixture was concentrated and the crude product was purified by-silica gel chromatography to afford the bromide 117.

(viii) Biphenyl Bis-Hydroxyethyl Amine 118

To a solution of the bromide 117 in dioxane and water was added 2 eq. of bis-ethanolamine and solid Na$_2$CO$_3$ at room temperature. After 12 h, the reaction mixture was extracted with methylene chloride, dried over MgSO$_4$, and concentrated. The crude product was purified by silica gel chromatography to afford the bis-hydroxyethyl amine 118 (18 mg, 0.027 mmol, 42% overall yield from 116).

(ix) Biphenyl Disulfide 119

A solution of 15 mg (0.023 mmol) the bis-hydroxyethyl amine 118 was treated with 13 mg of carbon tetrabromide and 10 mg of triphenyl-phosphine at room temperature. After 2 hr, the reaction mixture was concentrated, redissolved in 1 mL of anhydrous ethanol and treated with 20 mg of potassium thioacetate at room temperature. After reflux for 4 hr, the reaction mixture was diluted with ethyl acetate, washed with sat. sodium bicarbonate, water, brine, dried over MgSO$_4$, and concentrated. The crude product was purified by silica gel chromatography to afford the bis-acetylthioethyl amine. The amine was treated with NaOH in methanolic water at room temperature. After 12 h, the reaction mixture was extracted with and with methylene chloride and the combined organic phases were dried over MgSO$_4$ and concentrated. The crude product was purified by silica gel chromatography to afford the disulfide 119 (6 mg, 0.009 mmol, 38% yield from 118).

(x) Technetium Complex 120

To a suspension of the disulfide 119 in 50% aqueous sulfuric acid is added ground sodium nitrite at 0° C., under which condition the Boc groups are removed prior to the tetrazotization. After 30 min, the reaction mixture is added salicylic acid dissolved in aq. sodium carbonate. Upon addition, the pH of the reaction mixture is adjusted to 9–10 by slow addition of precooled sat. sodium carbonate solution while keeping the reaction temperature under 10° C. After overnight at 4° C., the reaction mixture is acidified (pH 3) and the resulting precipitate is filtered with a Buchner funnel. The collected product mixture is purified with silica gel column using DMF-hexane as an eluent system. The purified dye suspended in water is then treated with ammonium pertechnetate (NH$_4$TcO$_4$), sodium hydrosulfite, and the resulting suspension is refluxed for 5 hr. The reaction mixture is extracted with methylene chloride, dried over MgSO$_4$, and chromatographed to give the metal complex 120.

SCHEME XI
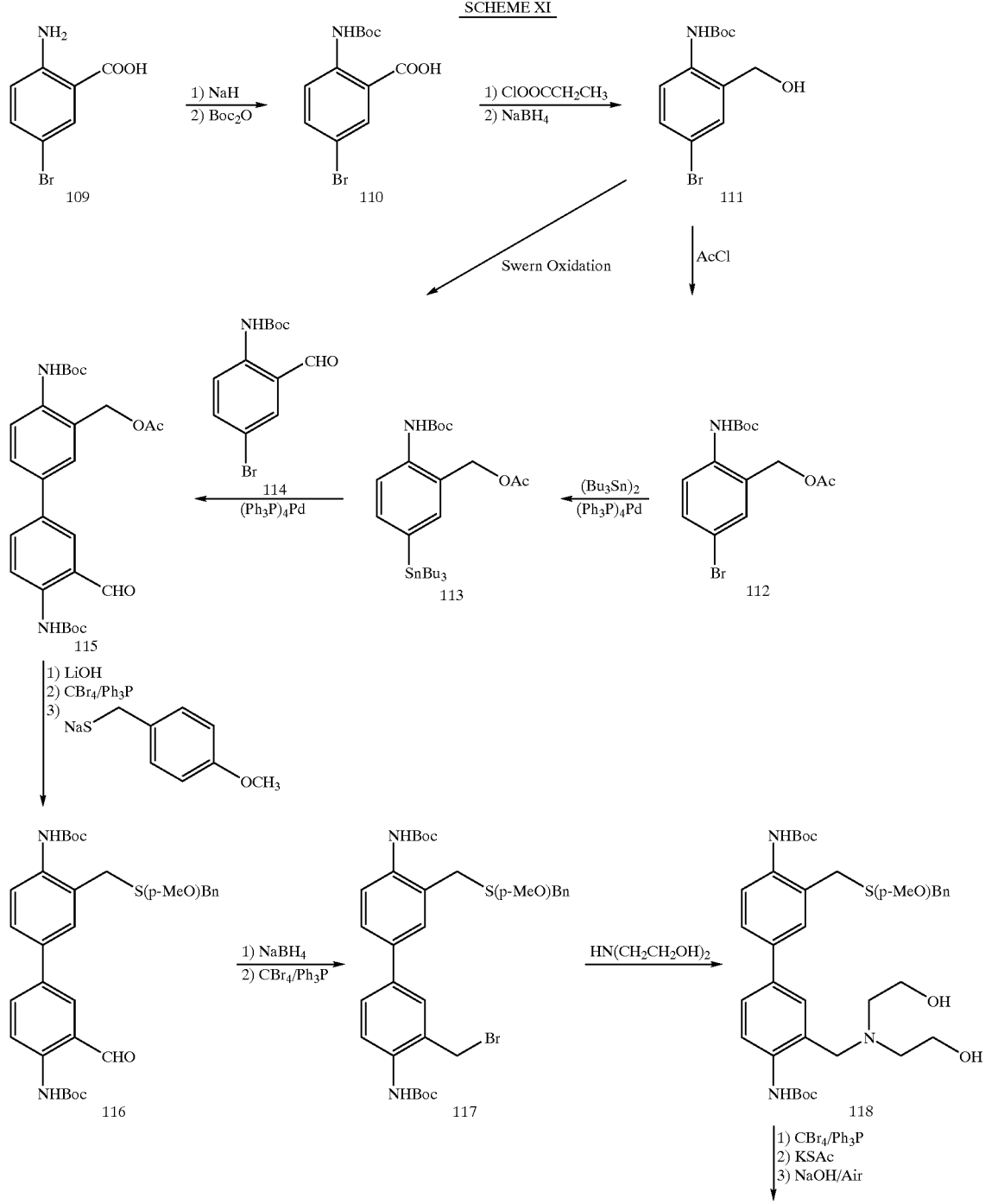

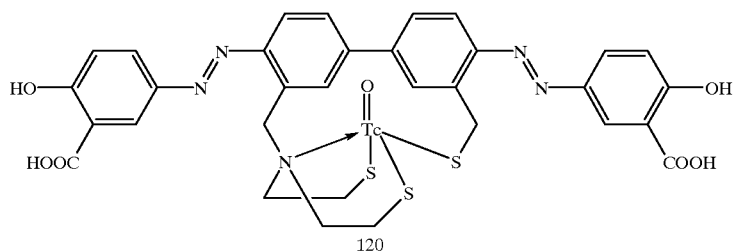
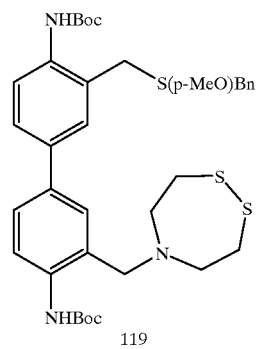

Example 21

Preparation of Tc Complex 122 (Prep. Scheme XII)

(i) Biphenyl Diol 121

To a solution of the benzoate 115 in THF and water is added LiOH at 0° C. After completion of the reaction, the product benzyl alcohol is treated with thionyl chloride at room temperature. The resulting benzyl chloride is subsequently reacted with sodium azide to give the biphenyl azide. A solution of the biphenyl azide in anhydrous MeOH is reduced with sodium borohydride to its azido alcohol. Upon reaction with thionyl chloride, the benzyl alcohol is converted to the biphenyl diol 121 via benzyl chloride.

(ii) Complex 122

The two hydroxy groups are converted into dibromide with either carbon tetrabromide/triphenyl phosphine system or bromine, which is then treated with excess sodium azide to give tri-azide. The tri-azide groups are reduced to the tri-amines with triphenyl phosphine, and subsequently protected with Fmoc group to afford the Fmoc protected amine. The Fmoc protected amine is tetrazotized with sodium nitrite in acid, under which condition the Boc groups are removed prior to the tetrazotization, to its tetrazonium salt. Treatment with 3 eq. salicylic acid affords the corresponding azo dye. Deprotection of Fmoc group with piperidine followed by Tc loading step using ammonium pertechtenate and sodium hydro sulfite in boiling water provides the desired metal complex 122.

SCHEME XII

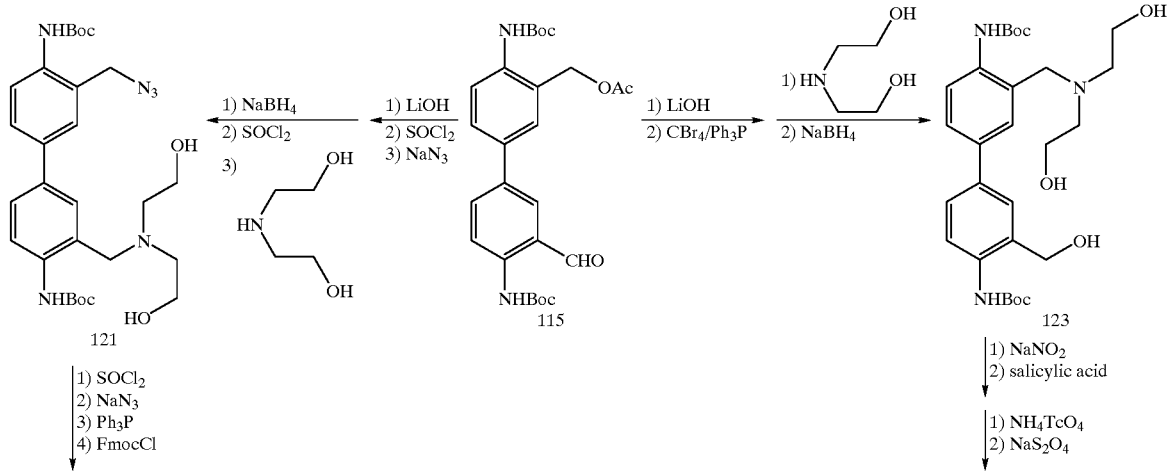

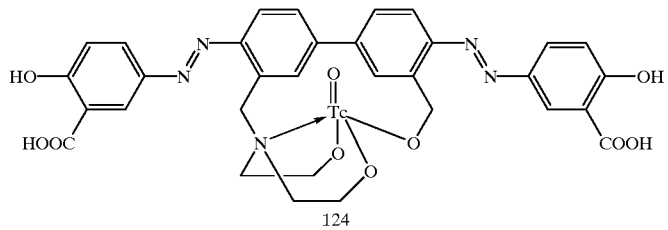

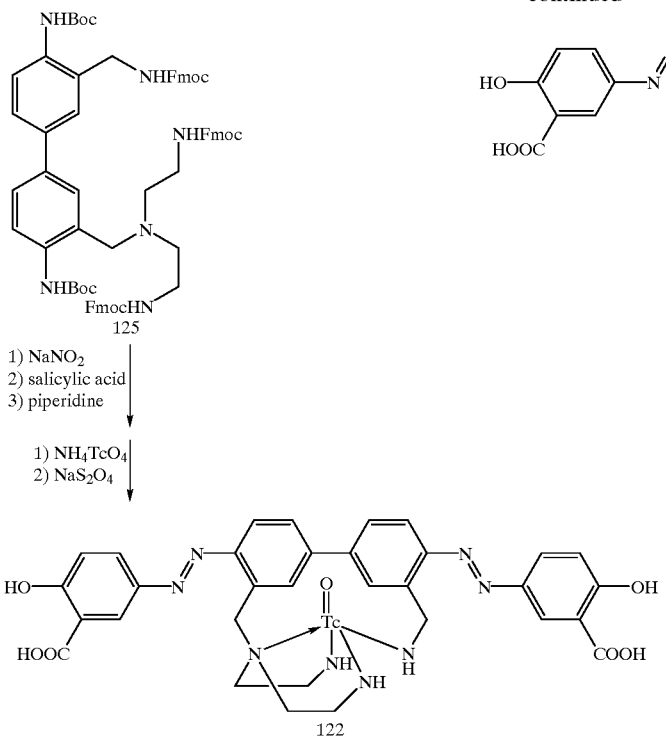

Example 22

Preparation of Tc Complex 124 (Prep. Scheme XII)

(i) Biphenyl Triol 123

The benzoate 115 is hydrolyzed to its alcohol with LiOH, which is then treated with carbon tetrabromide and triphenyl phosphine to its bromide. The bromide is reacted with bis-ethanolamine and its aldehyde functional group is reduced with sodium borohydride to the corresponding triol 123.

(ii) Tc Complex 124

The triol 123 is tetrazotized with sodium nitrite in acid under which condition the Boc groups are removed prior to the tetrazotization. Subsequent treatment with salicylic acid at pH around 9 provides the azo dye. The azo dye is treated with ammonium pertechtenate and sodium hydro sulfite in boiling water to give the complex 124.

Example 23

Binding of $NX_3$ Technetium Complexes to β-Amyloid

This example illustrates the affinity of $NX_3$ technetium complexes for β1-40 amyloid fibrils. A similar protocol to that described in Example 6 is used.

Example 24

Synthesis of $N_2S_2$ Complexes (Prep. Schemes XIII and XIV)

(i) 2-Iodo-4,4'-Dinitrobiphenyl 77

To a 250 mL 3-neck round-bottom flask charged with 7.8 g (30.16 imol) of the amine 76 (see Case, F. H., J. Am. Chem. Soc. 68:2574–2577 (1946)) was added 50 mL of conc. sulfuric acid. After the mixture became homogeneous, it was cooled to 0°. In a separate 50 bL flask 2.8 g of sodium nitrite was slowly to 25 mL of sulfuric acid over 30 min. at 5°. The resultant solution was then slowly added to the amine solution with cooling. Manual agitation of the reaction mixture was necessary. Next, 75 mL of 85% phosphoric acid was added over one hour via addition funnel, during which time the temperature of the reaction mixture was kept below 10°. The mixture was agitated periodically to assure homogeneity. Conversion to the diazonium salt was monitored by adding a drop of the reaction mixture to 10 mL of water. When the solution turned light yellow and no insoluble material was formed, the reaction was complete. The reaction mixture was then allowed to warm to room temperature over 2 h and, added to 500 mL of ice water with stirring. After 30 min, excess urea (6 g) was slowly added to destroy excess nitrous acid and the reaction mixture was stirred for 30 min. To this mixture was added an aqueous solution of potassium iodide (11.34 g in 75 mL). The reaction mixture was then heated to 70°. The reaction mixture was extracted with $CH_2Cl_2$, dried over $MgSO_4$ and (concentrated, The crude product was purified by silica gel chromatography (1/1 Hexane/$CH_2Cl_2$) to afford the dinitroiodide product 77 9.83 g, 26.86 mmol, 89% yield) as light yellow solid. $^1$H NMR (DMSO-$d_6$) δ8.75 (d, 1H, J=2.1 Hz), 8.38–8.32 (m, 3H), 7.71–7.64 (m, 3H).

(ii) 2-Cyano-4,4'-Dinitrobiphenyl 78

A solution of the iodide 77 (5.0 g, 13.66 mmol) and CuCN (1.65 g, 18.42 mmol) in 30 mL of anhydrous dimethiylsulfoxide was heated (180° C.) under an argon atmosphere. After 2 hr, the reaction mixture was added to a 0° solution of aqueous ammonium chloride (100 mL) and filtered through a Buchner funnel. The insoluble product was partitioned into methylene chloride and water. The separated organic layer was dried over $MgSO_4$ and concentrated. The crude product was purified by silica gel chromatography (1/1 Hexane/CH$_2$Cl$_2$ to 30%/69%/1% Hexane(CH$_2$Cl$_2$/MeOH) to afford the nitrile 78 (3.3 g, 12.27 mmol, 90% from 77) as a light yellow solid. $^1$H NMR (DMSO-d$_6$) δ8.69 (d, 1H, J=2.3), 8.56 (dd, 1H, J$_1$=8.6, J=2.3), 8.44–8.41 (m, 2H), 7.80–7.76 (m, 3H).

(iii) Triamine 79

A solution of nitrile 78 (750 mg, 2.79 mmol) in methanol (100 mL) was shaken with 10% Pd on C (200 mg) under H$_2$ (55 psi) for 24 h, using a Parr apparatus. The reaction mixture was filtered through Celite and concentrated to afford the diamino nitrile as a yellow oil (559 mg, 2.67 mmol, 96%) R$_f$=0.54 (7:93 MeOH/CH$_2$Cl$_2$). The crude product was dissolved in tetrahydofuran (5 mL) and added in a dropwise manner to a suspension of LiAlH$_4$ (1 g, 26.4 mmol) in THF (30 mL) and the reaction mixture was heated to reflux under argon. After 17 h, the reaction mixture was cooled to room temperature and quenched by sequential addition of H$_2$O and 5% NaOH. The mixture was filtered to remove insoluble aluminum salts and the filtrate was extracted with CH$_2$Cl$_2$, dried over potassium carbonate, filtered, and concentrated in vacuo to give a triamine 79 as a tan oil (432 mg, 2.03 mmol, 76% from 78). $^1$H NMR (DMSO-d$_6$) δ6.93 (d, J=8.3, 2H), 6.77 (d, J=8.5, 1H), 6.68 (d, J=1.8, 1H), 6.55 (d, J=8.4, 2H), 6.43 (dd, J=8.4, 2.5, 1H), 4.98 (brs,, 2H), 4.91 (brs, 2H), 3.32 (s, 2H), 3.17 (s, 2H).

(iv) Compound 81

A solution of 2-aminoethanethiol.HCl 80 (11.4 g, 100 mmol), triphenylmethanol (TrOH, 26.0 g, 100 mmol) in HCl (37%, 44.8 mL) and acetic acid (280 mL) was stirred for 5 h at 40° C. The reaction mixture was concentrated in vacuo and the resulting white solid was washed with ether and dissolved in H$_2$O/CH$_2$Cl$_2$ (1:1). After adjusting the pH of the aqueous layer to ca. 14 with 1 N NaOH, the desired compound was removed by extraction. The combined organic layers were dried (K$_2$CO$_3$), filtered, and concentrated in vacuo to provide a white solid, S-(triphenylmethyl) 2-aminoethanethiol (28.8 g, 90.0 mmol, 90% from 80). R$_f$=0.50 (1:9 MeOH/CH$_2$Cl$_2$); $^1$H NMR (DMSO-d$_6$) δ7.35–7.20 (m, 15H), 2.43 (t, J=6.1, 2H), 2.15 (t, J=5.9, 2H). To a solution of S-(triphenylmethyl) 2-aminoethanethiol (3.00 g, 9.40 mmol) and triethylamine (951 mg, 9.40 mmol) in dry CH$_2$Cl$_2$ (30 mL) was added bromoacetyl bromide (1.90 g, 9.40 mmol) over 15–20 min at −20°. The reaction mixture was stirred at −20° for 30 min and at room temperature for 1 h. To this mixture was added an additional equivalent of S-(triphenylmethyl) 2-amninoethanethiol (3.00 g, 9.40 mmol) and triethylamine (951 mg, 9.40 mmol). After stirring for 16 h at room temperature, the reaction mixture was concentrated under reduced pressure. The crude product was purified by flash chromatography (1:99 MeOH/CH$_2$Cl$_2$) to give compound 81 as a white foam (4.64 g, 6.95 mmol, 67% from amine 80). R$_f$0.60 (1:9 MeOH/CH$_2$Cl$_2$); $^1$H NMR (DMSO-d$_6$) δ7.77 (t, J=6.1, 1H), 7.35–7.20 (m, 30H), 2.97 (dd, J=6.0, 5.9, 2H), 2.86 (s, 2H), 2.35 (t, J=6.1, 2H), 2.18 (m, 4H). See Photaki et al., J. Chem. Soc. (c) 2683–2687 (1970); Bryson, N. J., Neutral technetium (v) complexes with N,S-donor chelates. Ph.D. thesis, Massachusetts Institute of Technology, Cambridge, Mass. (1988).

(v) Compound 82

To a solution of 81 (2.68 g, 3.96 mmol) in acetonitrile (100 mL) was added methyl 3-bromopropionate (2 mL, 28.8 mmol), KHCO$_3$ (500 mg), and K$_2$CO$_3$ (500 mg). The reaction mixture was refluxed under argon at 80° C. for 12 h. After cooling to room temperature and filtering, the solution was concentrated. The crude product was purified by flash chromatography (hexane, then 1:3 ethyl acetate/hexane) to give compound 82 as a pale yellow oil (1.96 g, 2.58 mmol, 65% from 81) R$_f$=0.35 (1:3 EtOAc:Hexane) and recovered 0.67 g (1.0 mmol) of 81 (yield was 87% based on recovered starting material). $^1$H NMR (DMSO-d$_6$) δ7.58 (t, J=6.0, 1H), 7.31–7.22 (m, 30H), 3.47 (s, 3H), 2.94 (q, J=6.5, 2H), 2.79 (s, 2H), 2.51–2.47 (m, 2H), 2.32–2.2,6 (m, 4H), 2.22–2.17 (m, 4H).

(vi) Compound 83

To a solution of 82 (1.53 g, 2.0 mmol) in MeOH (15 mL), H$_2$O (10 mL), and THF (15 mL) was added LiOH·H$_2$O (168 mg, 4.0 mmol). The resulting solution was stirred for 3 h at room temperature. Organic solvent was removed under vacuum and the resultant aqueous solution was acidified to pH 4 with 10% HCl and extracted with ethyl acetate. The combined ethyl acetate fractions were dried over MgSO$_4$ and evaporated to give the acid as a white solid (1.50 g) (R$_f$=0.71 (7:1:92 MeOH/acetic acid/CH$_2$Cl$_2$); $^1$H NMR (DMSO-d$_6$) δ7.67 (t, J=5.8, 1H), 7.31–7.18 (m, 30H), 2.95 (q, J=6.7, 2H), 2.79 (s, 2H), 2.51–2.46 (m, 2H), 2.30–2.16 (m, 8H). To a solution of the crude acid (1.50 g, 2 mmol) and N-hydroxysuccinimide (230 mg, 2.0 mmol) in THF (30 mL) was added 1,3-dicyclohexylcarbodiimide (430 mg, 2.0 mmol) in THF (10 mL). After stirring at room temperature for 2 h, the solution was filtered into a flask containing triamine 79 (405 mg, 1.9 mmol) in THF (10 mL). After 2 h at room temperature, the reaction mixture was concentrated and the crude product was purified by flash chromatography (CH$_2$Cl$_2$, then 3:97 MeOH/CH$_2$Cl$_2$) to give compound 83 as a brown solid (860 mg, 0.91 mmol, 45% from 82). R$_f$=0.49 (7:1:92 MeOH/acetic acid/CH$_2$Cl$_2$); $^1$H NMR (DMSO-d$_6$) δ8.09 (t, J=5.0, 1H), 7.71 (t, J=5.4, 1H), 7.29–7.19 (m, 30H), 6.89 (d, J=8.4, 2H), 6.82 (d, J=8.7, 1H), 6.55 (d, J=8.3, 2H), 6.49–6.47 (m, 2H), 4.99 (brs, 2H), 4.95 (brs, 2H), 4.04 (d, J=6.4, 2H), 2.95–2.91 (m, 2H), 2.76 (s, 2H), 2.51–2.49 (m, 2H), 2.35–2.31 (m, 2H), 2.22–2.13 (m, 6H).

(vii) Compound 84

To a solution of 83 (50 mg, 0.053 mmol) in THF (6 mL), H$_2$O (3 mL), and 10% HCl (280 μL) at 50 was added a solution of NaNO$_2$ (8 mg, 0.12 mmol) in H$_2$O (40 μL). After stirring at 5° for 2 min, the resulting yellow solution was added dropwise to a solution of 4-amino-1-naphthalenesulfonic acid sodium salt (61 mg, 0.25 mmol), sodium acetate trihydrate (108 mg, 0.79 mmol), and Na$_2$CO$_3$ (10 mg, 0.094 mmol) in H$_2$O (1 mL) at 5°. A distinct color change from yellow to orange-red was immediately observed. After stirring at 5° for 3 min, THF (1 mL) was added. After 1 h at 5° the mixture was concentrated and the crude product was purified by flash chromatography (CH$_2$Cl$_2$, then 1:9, 3:7 MeOH/CH$_2$Cl$_2$) followed by preparative HPLC (0–5 min 10% MeOH, 5–20 min 10–100% MeOH gradient, 20–25 min 100% MeOH, R$_v$=285–345 mL) to afford 84 as a red solid (32 mg, 0. 026 mmol, 42% from 83). R$_f$=0.29 (25:75 MeOH/CH$_2$Cl$_2$); UV(10 mM Na$_2$HPO$_4$, pH 7.4) λ$_{max}$486 nm (ε=4.36×10$^4$ cm$^{-1}$·M$^{-1}$), 324 nm (ε=4.56×10$^4$); $^1$H NMR (CD$_3$OD) δ8.81 (d, J=8.1, 2H), 8.65 (s, 1H), 8.64 (s, 1H), 8.29 (d, J=7.9, 1H), 8.28 (d, J=7.8, 1H), 7.96 (d, J=2.0, 1H), 7.91 (d, J=8.1, 3H), 7.66 (t, J=7.9, 2H), 7.53 (t, J=8.4, 4H), 7.46 (d, J=7.5, 1H), 7.30–7.25 (m, 12H), 7.16–7.0–7 (m, 18H), 4.48 (s, 2H), 2.97 (t, J=6.8, 2H), 2.86 (s, 2H), 2.62 (t, J=5.9, 2H), 2.34–2.25 (m, 8H). See Ashburn et al., Chemistry and Biology 3:351–358 (1996); Han et al., J. Am. Chem. Soc. 118:4506–4507 (1996).

(viii) Compound 86

To a solution of 83 (20 mg, 0.02 mmol) in THF (3 mL), H$_2$O (1.5 mL), and 10% HCl (80 μL) at 5° C. was added NaNO$_2$ (4 mg, 0.06 mmol) in H$_2$O (20 μL). After stirring at 5° for 2 min, the resulting yellow solution was added dropwise a solution of 250 uL 1-hydroxy-2-naphthoic acid (1:1 THF/0.5 M Na$_2$CO$_3$) at 5°. A distinct color change from yellow to orange-red was immediately observed. After stirring at 5° for 1 h, the solution was warmed to room temperature and acidified to pH 4–5 by addition of 10% HCl. This solution was extracted by EtOAc and dried over Na$_2$SO$_4$. Purification by flash chromatography (CH$_2$Cl$_2$, then 1:9, 3:7 MeOH/CH$_2$Cl$_2$) followed by preparative HPLC (0–5 min 10% MeOH, 5–20 min 10–100% MeOH gradient, 19–21 min 100% MeOH, R$_v$=285–315 mL) afforded 86 as a golden yellow solid (6 mg, 4.5 umol, 25% from 83). R$_f$=0.35 (25:75 MeOH/CH$_2$Cl$_2$); $^1$H NMR (CD$_3$OD) δ8.90 (dd, J=8.1, 7.8, 2H), 8.56 (s, 2H), 8.40 (d, J=8.1, 2H), 8.07–7.99 (m, 4H), 7.66–7.50 (m, 7H), 7.29–7.22 (m, 12H), 7.14–7.03 (m, 18H), 4.50 (s, 2H), 2.91 (t, J=6.9, 2H), 2.82 (s, 2H), 2.64 (m, 4H), 2.32–2.19 (m, 6H). See Ashburn et al., Chemistry and Biology 3:351–358 (1996); Han et al., J. Am. Chem. Soc. 118:4506–4507 (1996).

(ix) Compound 85

To a solution of 84 (9.0 mg, 6.4 μmol) in MeOH/H$_2$O (1:1, 3 mL) was added 0.1 M aqueous silver nitrate (330 μL). The dark silver mercaptide derived from 84 precipitated immediately. After 5 min, the precipitate was collected by centrifugation and resuspended in THF/H$_2$O (1:1, 3 mL). The solution was treated with 0.1 M dithiothreitol (DTT, 660 μL) for 5 min, followed by 10% Na$_2$CO$_3$ (80 μL) and the supernatant was collected by centrifugation. To a 10 mL vial containing 25 mM NH$_4$[TcO$_4$] (600 μL, New England Nuclear, Boston, Mass.) and 0.01 N NaOH (4.5 mL, pH 12) was added sequentially the supernatant and 1 M Na$_2$S$_2$O$_4$ (30 μL) in 0.01 N NaOH at room temperature. The reaction mixture was heated at ca. 75° C. for 30 min, cooled to room temperature, and purified by flash chromatography using C18 corasil (37–50 μm, Waters, Milford, Mass., 2×4 cm) (washed with H$_2$O, then eluted with MeOH). Purification by preparative HPLC (0–5 min 0% MeOH, 5–10 min 10% MeOH, 10–25 min 10–100% MeOH gradient, R$_v$=285–345 mL) afforded a red solid 85 (7.4 mg, 7.1 μmol, 88% from 84). Specific activity=1.26 mCi/mmol; UV (10 mM Na$_2$HPO$_4$, pH 7.4) λ$_{max}$482 nm (ε=1.19×10$^4$ cm$^{-1}$·M$^{-1}$), 328 nm (ε=1.43×10$^4$); $^1$H NMR (CD$_3$OD) δ8.77 (d, J=9.1, 2H), 8.62 (s, 1H), 8.60 (s, 1H), 8.30 (d, J=7.7, 2H), 8.02–7.90 (m, 4H), 7.67–7.47 (m, 7H), 4.56–4.48 (m, 4H), 3.54–3.47 (m, 2H), 3.13–2.40 (m, 10H); IR 1651, 1574, 1416, 1338, 1180, 1047, 960 (Tc=o) cm$^{-1}$. MALDI MS for C$_{42}$H$_{41}$N$_9$O$_9$S$_4$Tc [M]$^+$, calcd 1041, found 1042. See Han et al., J. Chem. Soc. 118:4506–4507 (1996).

SCHEME XIII

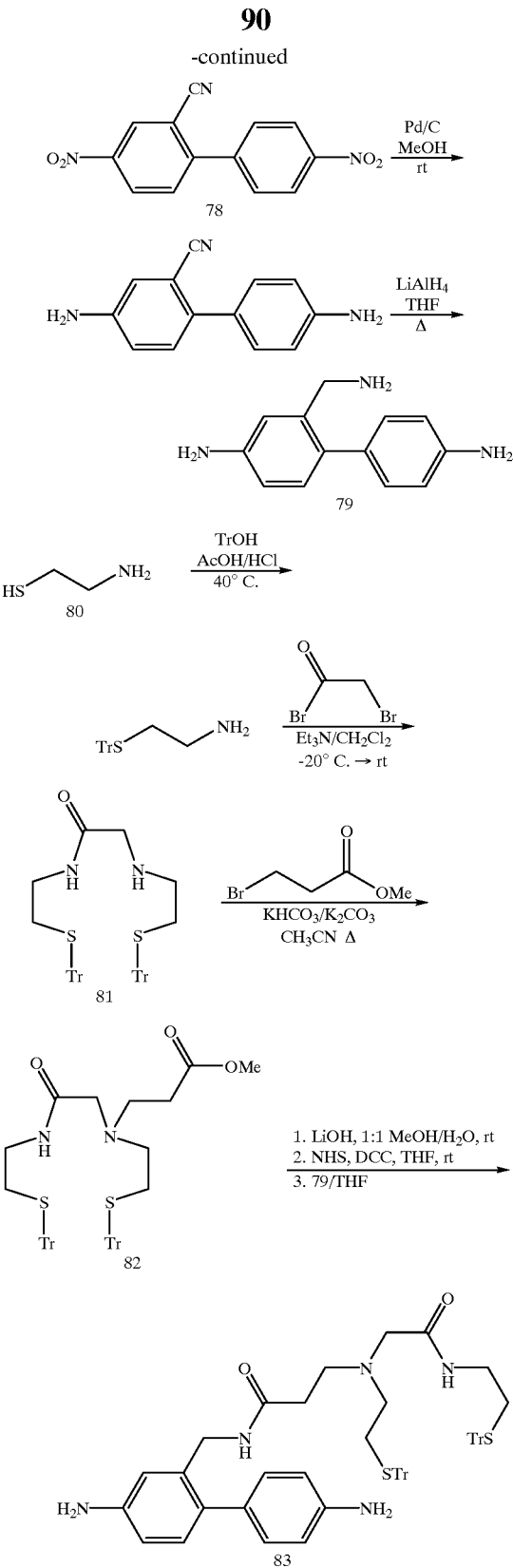

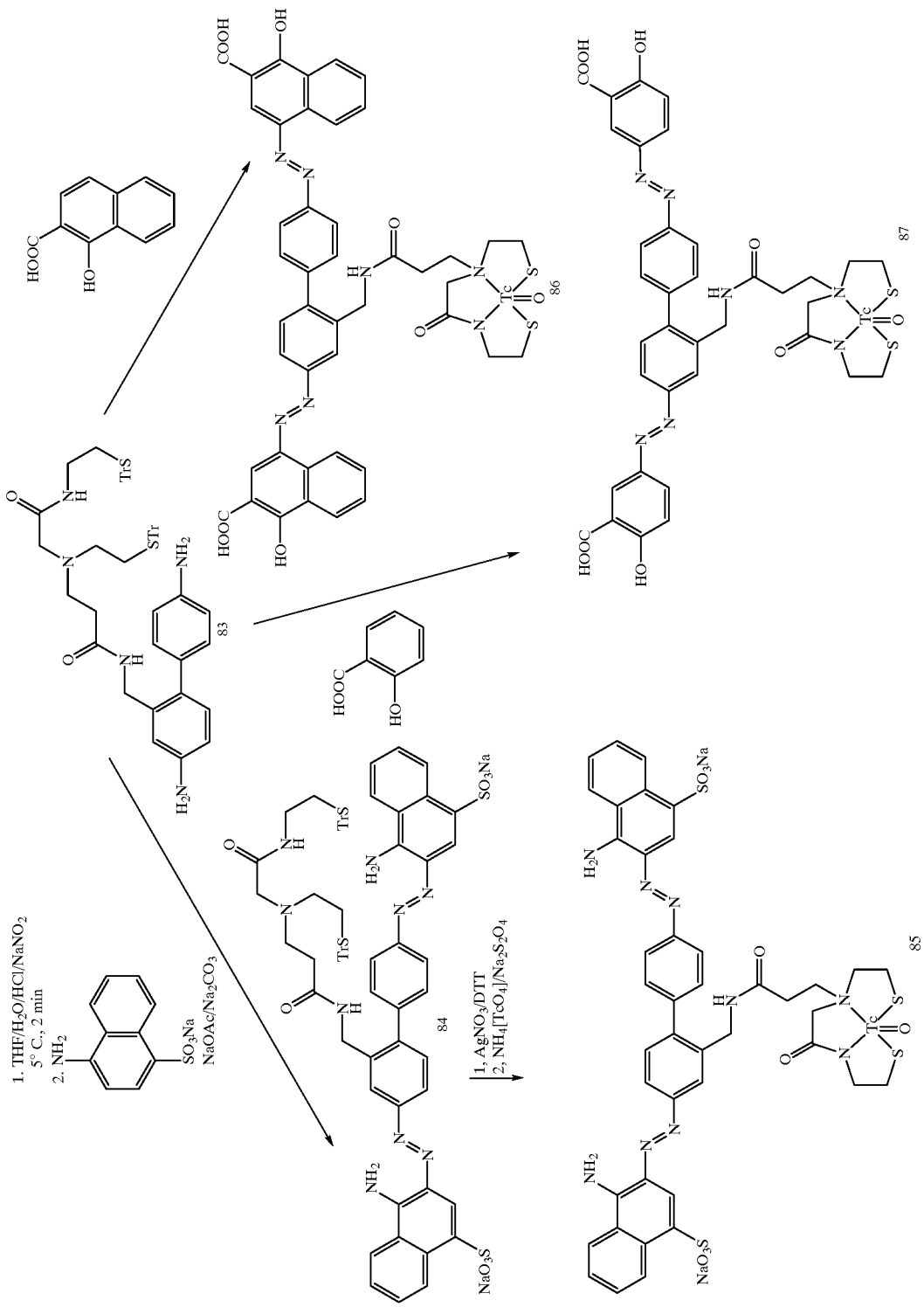

Example 25

Binding of $N_2S_2$ Technetium Complexes to β-Amyloid

This example illustrates the affinity of $N_2S_2$ technetium complexes for β1-40 amyloid fibrils. A similar protocol to that described in Example 6 is used.

Example 26

Preparation of Dimeric Amyloid Probes (a) Preparation of $N_2S_2$ Chyrsamine G-dimer 138 (Prep. Scheme XV)

To a solution of FMOCGlu in THF (ca. 0.2 M) is added 2 equiv. of 1,3,dicyclohexylcarbodiimide and 2 equiv. of N-hydroxy succinimide. After several hours, the solution is concentrated and the crude bis-NHS ester is precipitated as a white solid by addition of ether. The crude solid is dissolved in 1:1 THF:0.25 M $Na_2CO_3$ and 1 equiv. of triamine 79 is added. The solution is stirred at room temperature and extracted with dichloromethane. The combined organic phases are dried over sodium sulfate and concentrated to provide, after purification, the FMOC-protected tetraamine 137. 137 is diazotized and coupled to ortho salicylic acid as detailed in Example 24. The product is deprotected with piperidine and coupled to the N-hydroxysuccinimide ester 136 derived from 82. Technetium-99m is loaded according to Example 24, to afford compound 138.

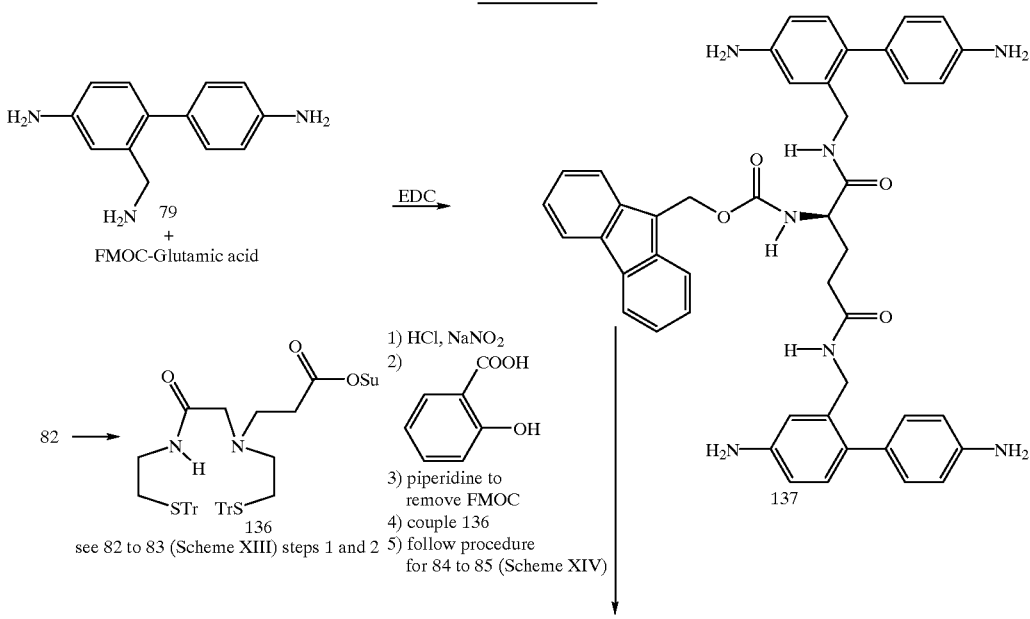

SCHEME XV

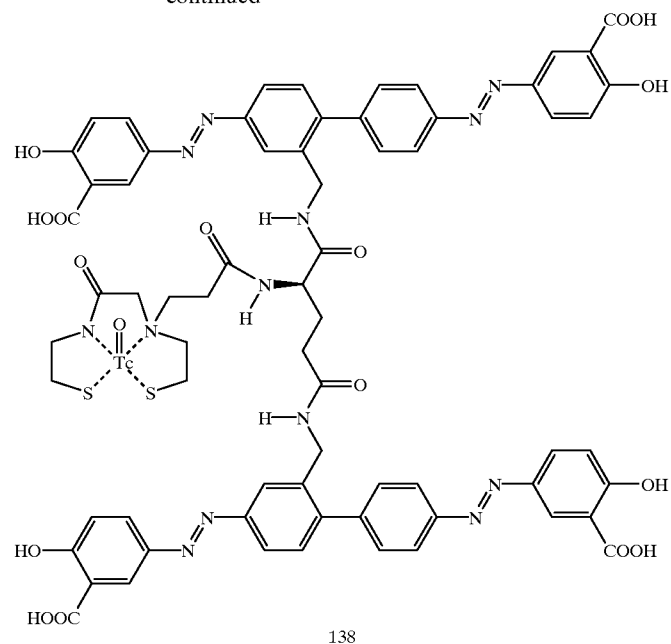

138

(b) Preparation of Head-to-Tail Dimer 127 (Prep. Scheme XVI)

Ortho salicylic acid is treated with oxalyl chloride (1 equiv.) in methylene chloride to afford the acid chloride, which is then added to a solution of 1,5 diamino pentane (0.5 equiv.) to afford, after concentration and purification, compound 126. 126 is added to a mixture of two bisdiazonium salts, derived from 83 and 4,4' biphenyl diamine by the procedure detailed in Example 24. The four possible coupling products are isolated and separated; the three shown in Scheme XVI, 127, 128 and 129, are possible amyloid probes.

SCHEME XVI

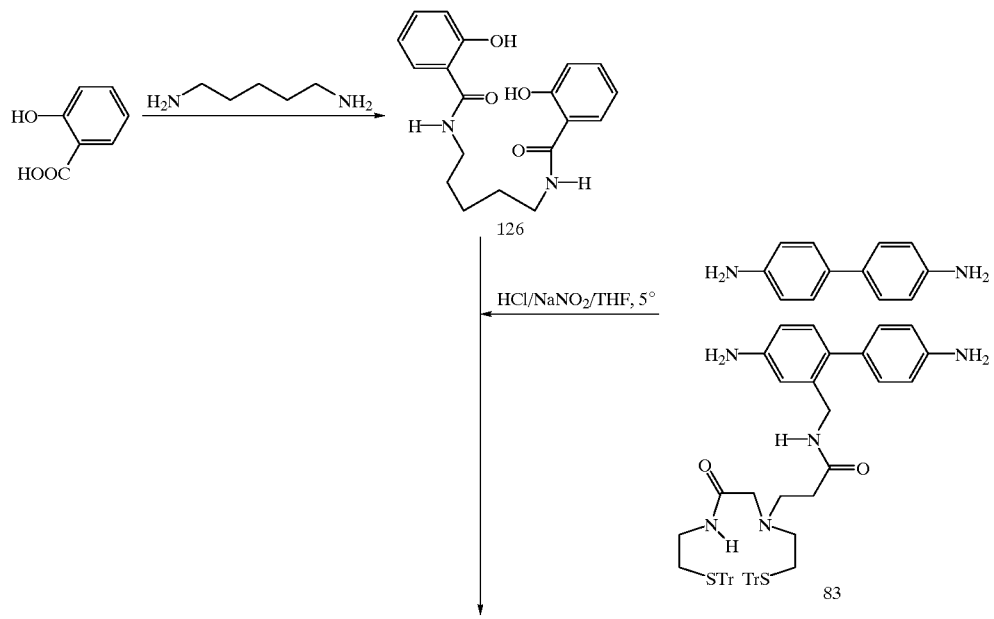

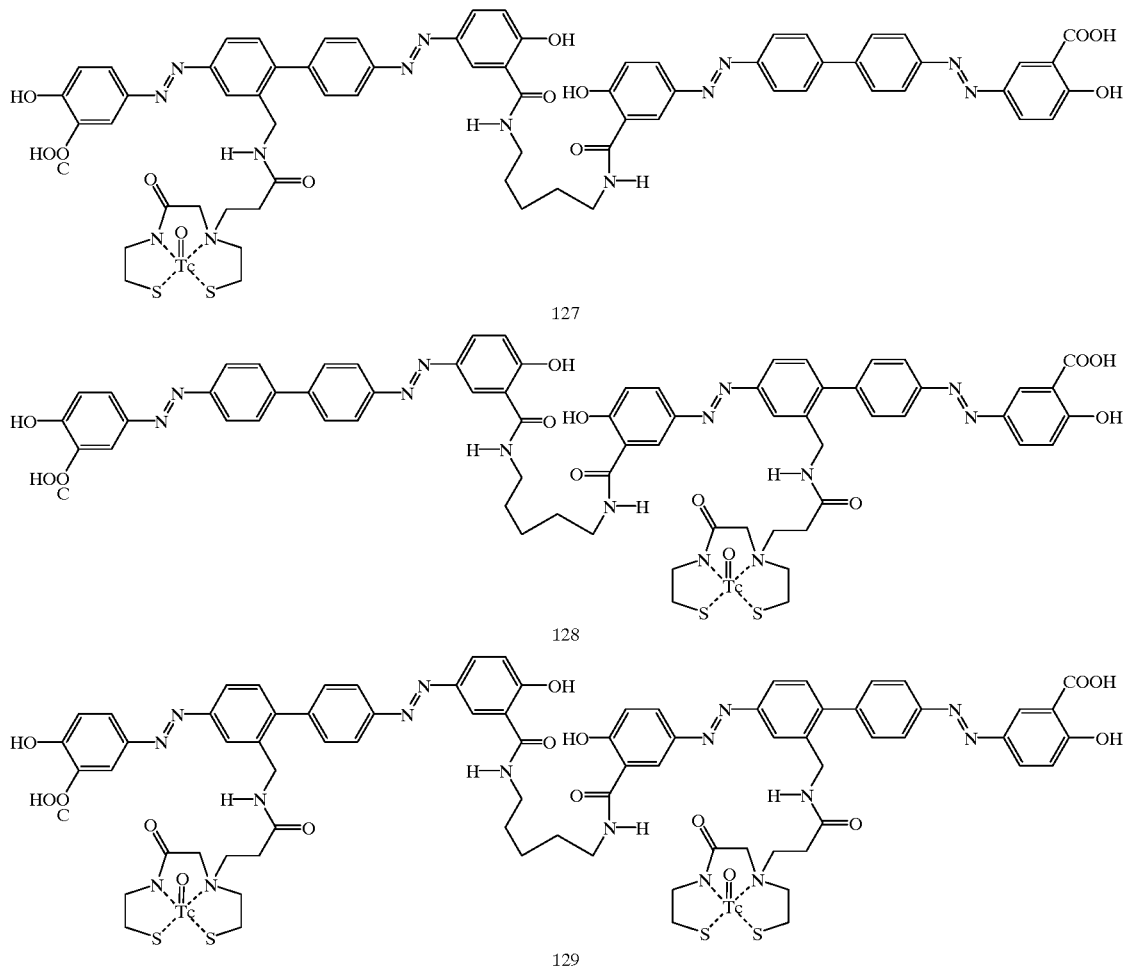

Example 27

Binding of N₂S₂ Technetium Dimers to β-Amyloid

This example illustrates the affinity of N₂S₂ technetium dimers for β1-40 amyloid fibrils. A similar protocol to that described in Example 6 is used.

Example 28

Preparation of Amyloid Binding Fluorescent Ligands (Prep. Scheme XVII)

(a) Congo Red Fluorescein Ligand 131

Triamine 79 (10 mg, 0.045 mmol) was dissolved in 1.0 mL of (1:1) THF/0.25 M Na₂CO₃ and Fluorescein succinimidyl ester (22 mg, 0.045 mmol) in 1 mL of (1:1) THF/0.25 M Na₂CO₃ was added. After stirring overnight, the solvent was evaporated and column chromatography on silica gel (0–25% MeOH/CH₂CL₂) to give the Fluorescein amine coupled compound 130 (20 mg, 75%). ¹H NMR (CD₃OD) δ8.45 (s, 1H), 8.10 (d, J=8.1, 1H), 7.28 (d, J=8.1, 1H), 7.05 (d, J=9.0, 1H), 6.52–7.06 (m, 12H), 4.52 (s, 2H), 1.95 (s, 1H). Congo Red with Fluorescein ligand was prepared by dissolving the Fluorescein diamine 130 in THF, H₂O and 10% HCl at 5° C., followed by addition of NaNO₂ in H₂O. After stirring at 5° C. for 2 min, the resulting yellow solution was added dropwise a solution of 4-amino-1-naphthalenesulfonic acid sodium salt, sodium acetate trihydrate and Na₂CO₃ at 5° C. This dimer 131 was purified by flash column chromatography on silica gel (0–25% MeOH/CH₂Cl₂CH₂CL₂) to give a red oil.

(b) Congo Red Rhodamine Ligand 133

Triamine 79 is dissolved in 1 mL of (1:1) THF/0.25 M Na₂CO₃ and the Fluorescin succinimidyl ester in 1 mL of (1:1) THF/0.25 M Na₂CO₃ is added. After stirring overnight, the solvent is evaporated and column chromatography on silica gel (0–25% MeOH/CH₂Cl₂CH₂CL₂) to give the Rhodamine amine coupled compound 132. Congo Red with Rhodamine probe is prepared by dissolving the Rhodamine diamine 132 in THF, H₂O and 10% HCl at 5° C., followed by addition of NaNO₂ in H₂O. After stirring at 5° C. for 2 min, the resulting solution is added dropwise a solution of 4-amino-1-naphthalenesulfonic acid sodium salt, sodium acetate trihydrate and Na₂CO₃ at 5° C. This dimer 133 is purified by flash column chromatography on silica gel (0–25% MeOH/CH₂Cl₂CH₂CL₂).

(c) Conqo Red Coumarin Ligand 135

Triamine 79 is dissolved in 1 mL of (1:1) THF/0.25 M Na₂CO₃ and the Coumarin Succinimidyl ester in 1 mL of (1:1) THF/0.25 M Na₂CO₃ is added. After stirring overnight, the solvent is evaporated and column chromatography on silica gel (0–25% MeOH/CH₂Cl₂CH₂CL₂) to give the Coumarin amine coupled compound 134. Congo Red with Coumarin ligand is prepared by dissolving the Coumarin diamine 134 in THF, H₂O and 10% HCl at 5° C., followed by addition of NaNO₂ in H₂O. After stirring at 5° C. for 2 min, the resulting solution is added dropwise a solution of 4-amino-1-naphthalenesulfonic acid sodium salt, sodium acetate trihydrate and Na₂CO₃ at 5° C. This dimer 135 is purified by flash column chromatography on silica gel (0–25% MeOH/CH₂Cl₂CH₂CL₂).

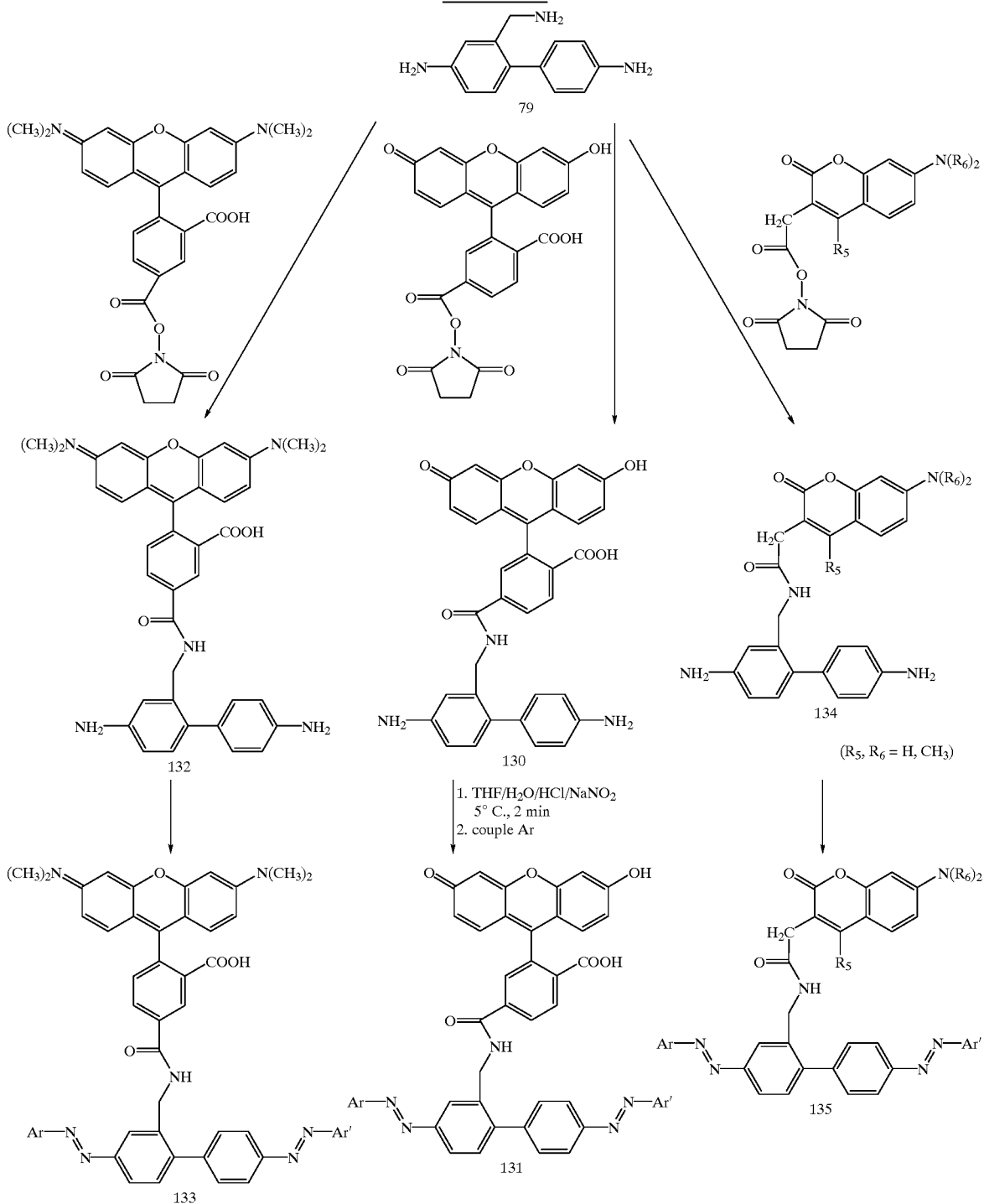

Example 29

Synthesis of Dimeric Fluorescent Ligands

Amine 79 is coupled to the appropriate fluorescent chromophore (FL, general formula), activated as the N-hydroxy succinimide ester (available from Pierce, Rockville, Ill.). The resultant compound (see Scheme XVII) is diazotizedt (HCl, NaSO$_2$, THF, 5°) according to the procedure used for the preparation of the N$_2$S$_2$ dimer, and coupled to two equivalents of the appropriate aromatic (Ar) compound, to provide fluorescent amyloid ligands. For example, by substituting fluorescent diamines 130, 132 or 134 (Scheme XVII) for diamine 83 in Scheme XVI, a series of head-to-tail fluorescent dimers can be assessed. Also, by substituting the commercially available fluorophore-NHS esters; (Pierce) for compound NHS ester 82 in Scheme XV, another class of fluorescent dimers can be produced.

Example 30

High-Throughput Fluorescent Assay for Inhibitors of Intracellular β-Amyloid Aggregation A cell line which produces intracellular β-amyloid is used. See, e.g., Martin et al., J. Biol. Chem. 270:26727–26730 (1995). Other cell lines also can be used, e.g., Down's syndrome human neurons isolated from Down's syndrome fetuses, or guinea pig neurons which have been treated with hydrogen peroxide. The cells are plated into a 96-well format. Solutions of candidate inhibitors are added and the cultures are incubated for between thirty minutes and 24 hours. At this time, the medium is removed by filtration and the cells are permeabilized using standard immunostaining methods. A solution of the fluorescent probe is added. After one to thirty minutes, the cells are washed (by filtration) several times to remove free probe. The plates are then analyzed in order to determine which wells retain the fluorescent probe. The wells which do NOT retain fluorescence contain a potential inhibitory compound or compounds. That is, an inhibitor inhibits the formation of β-amyloid aggregate and, therefore, the fluorescence signal. Those compounds which inhibit intracellular aggregation in this screen are further analyzed using standard fluorescence microscopy procedures.

Example 31

Combinatorial Synthesis of Labeled Compound Libraries (a) Labeled N$_2$S$_2$ Libraries (Prep. Scheme XVIII)

Scheme XIV illustrates the synthesis of a library of three molecules (85, 86 and 87) in which Ar=Ar'. These compounds are individually tested as described in Examples 33, 34 or 35. Libraries of greater complexity are synthesized and screened using the same principles.

Using any three aromatic groups described above as Ar or Ar', six compounds are possible in which Ar and Ar' are different. These are made by exposing the bis-diazonium salt derived from 83 to mixtures of two aromatic compounds (Scheme XVIII). The two aromatic compounds are not present in equimolar amounts, but rather are in a ratio determined by their relative reactivity, such that all four possible products are produced in equimolar ratios (see Scheme XVIII). This mixture is screened as described in Examples 33, 34 or 35, to determine the relative affinities for particular amyloid aggregates. Alternatively, the bis-diazonium salt derived from 83 is exposed to a mixture of all three aromatic compounds, to generate all nine possible compounds (85–93), which are screened for binding. Because it is difficult to generate approximately equimolar amounts of all possible adducts from more complex mixtures, larger libraries are generated from 2 or 3 aromatic compounds to produce groups of 4 or 9 compounds per well.

SCHEME XVIII

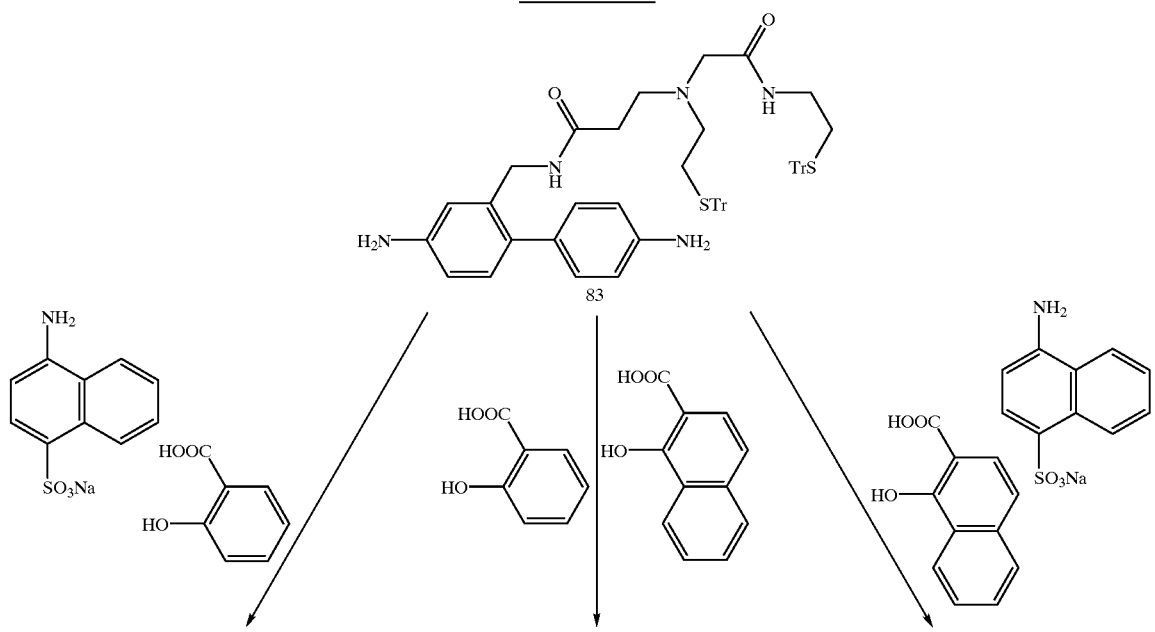

-continued

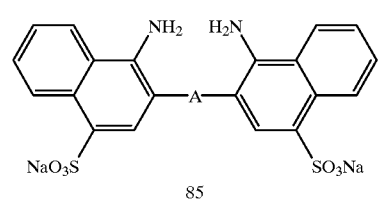
85

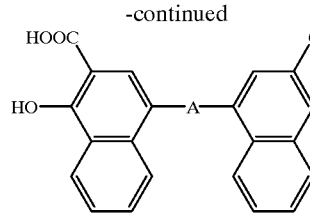
86

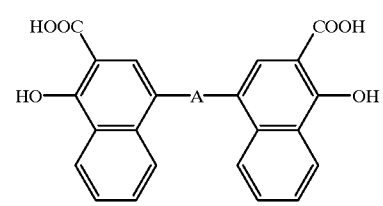
86

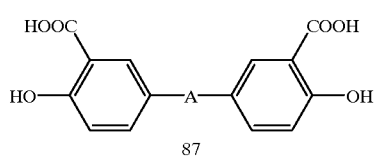
87

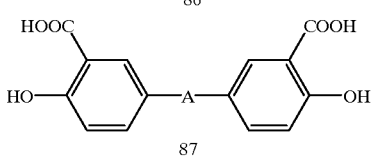
87

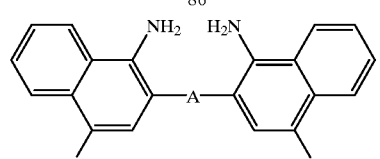
85

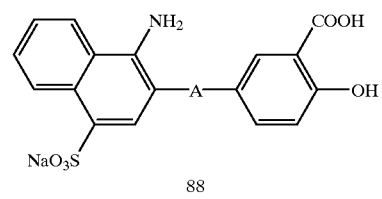
88

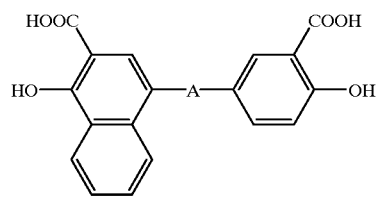
92

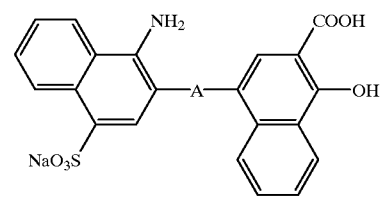
90

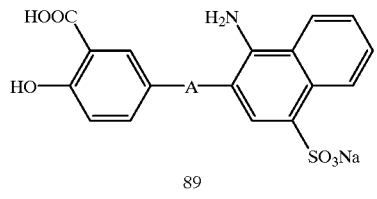
89

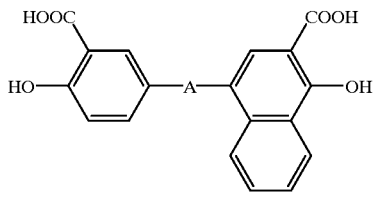
93

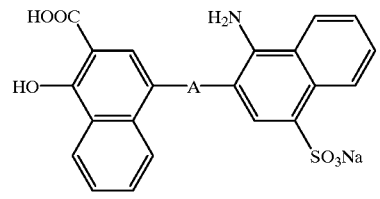
91

(b) Labeled $N_2S_2$ Dimer Libraries

Triamine 79 is protected with an acid-stable protecting group such as the fluorenylmethoxy carbonyl (FMOC) group, using standard procedures. The protected triamine is diazotized (dissolved in THF/water at 5° C. and diazotized by treatment with hydrochloric acid and sodium nitrite, as described in Example 24(vii)), and coupled to mixtures of aromatics as described above for the diamine 83. Using six aromatics, 36 FMOC-protected compounds are generated in groups of four. These compounds are deprotected by standard methods (e.g., piperidine, methylene chloride), and coupled to bis-N-hydroxysuccinimide esters that contain a protected (FMOC or tBOC) or derivatized (with $N_2S_2$ precursor) amino group. Thus, a group of four bis aromatic adducts (in approximately equimolar ratio) are coupled with a single diester to produce up to 16 compounds (if the diester is symmetric, there will be fewer adducts) in approximately equimolar ratio. Amyloid binding compounds are identified by any of the screening methods described in Examples 3.3–35. Libraries having, e.g., 12,960 compounds (36×36× 10), are easily generated and screened by this procedure.

Example 32

Generation and Isolation of β-Amyloid Protofibrils

This example illustrates a method for generating and isolating protofibrils using synthetic Aβ peptides. A stock solution was made by dissolving Aβ1-40 in DMSO to a final concentration of 2 mM and filtering through a 0.2 μm filter to remove undissolved material. An aliquot of the DMSO stock solution (10 μL) was diluted into 90 μl aqueous pH 7.4 buffer (10 mM phosphate, 100 mM Nacl) and thoroughly mixed. This solution was incubated at room temperature without agitation and protofibrils with lengths often exceeding 175 nm were visible by the second day of incubation. Protofibrils of similar lengths were also formed after similarly prepared incubations of Aβ1-42 at 20 μM were incubated for 8 days. Incubations of these peptides at lower concentrations generated protolibrils more slowly.

Protofibrils are isolated by sequential filtration of the early aggregation mixture through appropriate pore size and MW cutoff membranes to separate protofibrils from fibrillar and monomeric Aβ based on size differences. Aliquots of aggregation mixtures containing protofibrils are first filtered through an 0.2 μm pore size membrane to retain fibrils and allow Aβ protofibrils and monomers to pass into the filtrate. The peptide concentration of this filtrate is determined by quantitative amino acid analysis and aliquots of this filtrate are then centrifuged through 0.2 μm cutoff filter to separate protofibrils in the retentate from monomeric Aβ in the filtrate. The amount of monomeric Aβ remaining in the filtrate is determined by quantitative amino acid analysis and subtraction of this value from the peptide concentration of the first filtrate provides the amount of Aβ retained above the membrane in the form of protofibrils. The retained protofibrils are then resuspended in an appropriate aqueous buffer for use. cl Example 33

Screening Test Compounds For β-Amyioid Binding Ligands

This example illustrates treatment of various types of β-amyloid with test compounds to screen for compounds which are able to bind to the various types of β-amyloid.

β-amyloid is obtained by standard methods from naturally-derived neuritic plaque (mostly fibrillar by electron miscroscopy), naturally-derived diffuse amyloid (not fibrillar by electron microscopy; Congo Red negative), synthetic Aβ1-40 protofibrils, synthetic Aβ1-42 protofibrils, synthetic Aβ1-40 type-1 fibrils, synthetic Aβ1-40 type-2 fibrils, synthetic Aβ1-42 type-1 fibrils or synthetic Aβ1-42 type-2 fibrils. Compounds which bind strongly to any or all of the above can be used as imaging ligands or amyloid aggregation inhibiting agents.

Stock solutions of the test compounds are prepared in aqueous buffer solutions and the concentrations are determined by calculation from the maximum absorbance in the UV-VIS spectra. Protofibrils are isolated as described in Example 32. Type-1 and type-2 fibrils are isolated as a mixture by filtration through a semipermeable filter which retains the fibrils. Neuritic plaque is isolated as described in Roher et al., J. Biol. Chem. 268:3072–3083 (1993), and diffuse amyloid is isolated as described in Gowing et al., J. Biol. Chem. 269:10987–10994 (1994). The isolated β-amyloid is resuspended in buffer containing the test compound, incubated for 30 min. at 25° C. and centrifuged through a 0.2 μm cutoff membrane. The concentration of free ligand for use in Scatchard calculations is determined by calculation from the maximum absorbance in UV-VIS spectra taken of the filtrate. When using a radioactive compound, the amount of free ligand is determined by measuring the radioactivity of the filtrate. In this way, an effective binding constant is determined.

A similar protocol can be used to screen test compounds which bind to other amyloid proteins, e.g., Islet amyloid polypeptide, Ig light chain, transthyretin, lysozyme or $\beta_2$-microglobulin.

Example 34

Screening for Compounds Which Bind Specifically to β-Amyloid Protofibrils But Not to Other β-Amyloid Fibrils This example illustrates treatment of various types of β-amyloid fibrils with test compounds to screen for compounds which are able to bind specifically to β-amyloid protofibrils but not to other types of β-amyloid fibrils. Compounds which bind strongly to the protofibrils can be used as imaging ligands or amyloid aggregation inhibiting agents.

The test compounds are individual compounds or libraries of compounds. Stock solutions of the test compounds are prepared in aqueous buffer solutions and the concentrations are determined by calculation from the maximum absorbance in the UV-VIS spectra. Protofibrils are isolated as described in Examples 32. Type-1 and type-2 fibrils are isolated as a mixture by filtration through a semipermeable filter which retains the fibrils. Neuritic plaque is isolated as described in Roher et al., J. Biol. Chem. 268:3072–3083 (1993), and diffuse amyloid is isolated as described in Gowing et al., J. Biol. Chem. 269:10987–10994 (1994). The isolated β-amyloid is resuspended in buffer containing the test compound, incubated for 30 min. at 25° C. and centrifuged through a 0.2 μm cutoff membrane. The concentration of free ligand for use in Scatchard calculations is determined by calculation from the maximum absorbance in UV-VIS spectra taken of the filtrate. When using a radioactive compound, the amount of free ligand is determined by measuring the radioactivity of the filtrate. For a library of compounds, tested at equal concentrations, strong binders are defined as those for which the amount of free ligand is lowest.

Each screen involves the incubation of the solution of the test compound(s) with the insoluble aggregate of one of the above described types of β-amyloid. The mixture is then filtered through a filter which has been previously determined to retain the β-amyloid aggregate. The desired test compound(s) are retained by the β-amyloid aggregate. By running two or more screens sequentially, compound(s) are identified which bind selectively to one form of β-amyloid aggregate.

For example, a library of compounds obtained as described in Example-31, is incubated with type-1 or type-2 fibrils, and then filtered. Library synthesis affords one compound each in every well of a 96-well plate. Each well has a 0.2 μm filter at the bottom. Fibrils are added to each well and, after a 30 minute incubation, the mixtures are filtered and the amount of compound in the filtrate is measured. Those members of the original group of compounds which are not retained by the filter, are subjected to a second screen with protofibrils. Compounds which are retained by the protofibrils on the filter are specific binders for protofibrils. These compounds are identified by their position in the 96-well plate: the position encodes the subunits added during the synthesis. (See Example 31).

Example 35

Identification of Amyloid-Binding Compounds in Combinatorial Libraries Using a Competitive Binding Assay This example illustrates the screening of the combinatorial libraries constructed in Example 31, for amyloid binding compounds, e.g., to protofibrils, type-1 fibrils, type-2 fibrils, neuritic plaque and/or diffuse amyloid, comprised of, e.g., Aβ1-40 or Aβ1-42. In each case, the amyloid aggregate is added to one of, e.g., 96 wells containing an aqueous solution (pH 7.4, 10 mM phosphate buffer) of a pure compound or a defined mixture of compounds from the combinatorial synthetic library. After a thirty minute incubation period, the mixture is filtered into a filtrate well through a filter which retains amyloid aggregate and bound compound(s). The UV/vis spectrum and/or the HPLC profile of the filtrate from each well is compared to the profile before exposure to the amyloid aggregates and subsequent filtration. Filtrate wells in which the composition, either in relative or absolute terms, is significantly different from that of the original well is further deconvoluted. Deconvolution consists of the separate synthesis and evaluation for amyloid binding (see Example 33) of each compound contained in the original mixture. In this way, those compounds in a synthetic combinatorial library with a relatively high affinity for a given amyloid aggregate are rapidly identified.

By placing two or more filtration steps in sequence, compounds which are selective in their binding properties can be identified. For example, addition of type-1 fibrils to the original wells, followed by filtration, will produce a filtrate library which contains no compounds with high affinity for type-1 fibrils. This library is treated with amyloid protofibrils and subjected to a second filtration step. By comparison of the filtrates from the first step to those from the second, compounds which bind the protofibrils are identified as described above. These compounds do not have high affinity for the type-1 fibrils.

Those skilled in the art will be able to ascertain, using no more than routine experimentation, many equivalents of the specific embodiments of the invention described herein. These and all other equivalents are intended to be encompassed by the following claims.

What is claimed is:

1. An amyloid binding compound of the formula:

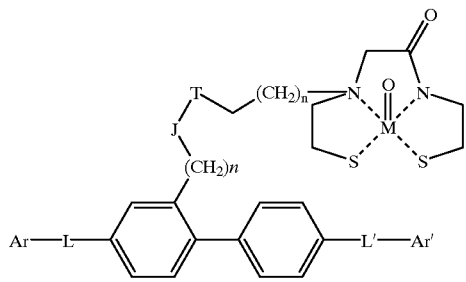

and pharmaceutically acceptable salts thereof;
wherein.
  J is selected from the group consisting of NH, O and S;
  T is selected from the group consisting of CO and $CH_2$;
  n is a number selected from the group of 1, 2, 3, 4, 5 and 6;
  M is selected from the group consisting of $^{99m}Tc$, $^{111}In$, $^{90}Y$, $^{99}Tc$ and $^{186}Re$;
  L and L' are independently selected from the group consisting of —N=N—, —CONH—, —NHCO—, —HN—NH—, and —C=C—;
and
  Ar and Ar' are independently selected from the group consisting of:

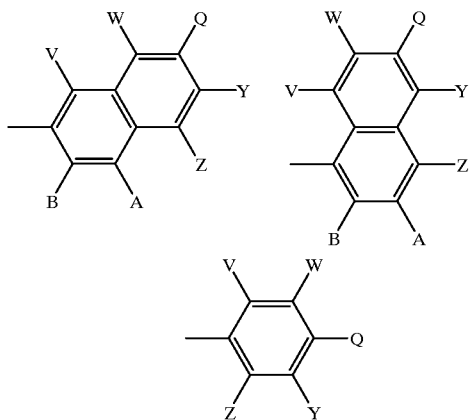

wherein each of the groups designated V, W, Q, Y, Z, A and B is independenti selected from the group consisting of:
  OH, COOH, H, $R^5$ (wherein $R^5$ is a $C_{1-6}$ hydrocarbon), $CO_2R^6$ (wherein $R^6$ is a $C_{1-6}$ hydrocarbon), $CONH_2$, CN, $NH_2$, $CH_2NH_2$ and $SO_3$.

2. An amyloid binding compound selected from the group consisting of:

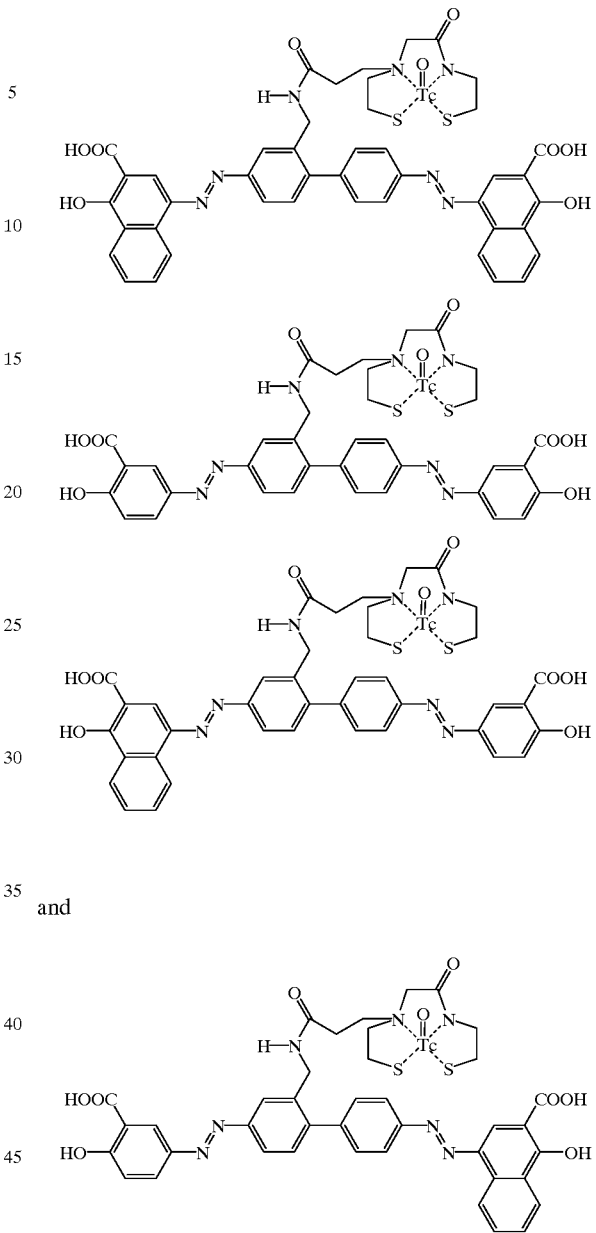

and pharmaceutically acceptable salts thereof.

* * * * *